US008586339B2

(12) United States Patent
Dicosimo et al.

(10) Patent No.: US 8,586,339 B2
(45) Date of Patent: Nov. 19, 2013

(54) FACILITATED PROCESS FOR PURIFICATION OF PROTEINS

(75) Inventors: Robert Dicosimo, Chadds Ford, PA (US); Arie Ben-Bassat, Wilmington, DE (US); Raymond Richard Zolandz, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 222 days.

(21) Appl. No.: 13/070,118

(22) Filed: Mar. 23, 2011

(65) Prior Publication Data
US 2011/0250673 A1 Oct. 13, 2011

Related U.S. Application Data

(60) Provisional application No. 61/341,109, filed on Mar. 26, 2010.

(51) Int. Cl.
| C12P 7/24 | (2006.01) |
| C12N 9/00 | (2006.01) |
| C12N 9/10 | (2006.01) |
| C12N 9/16 | (2006.01) |
| C12N 1/20 | (2006.01) |
| C12N 15/00 | (2006.01) |
| C07H 21/04 | (2006.01) |

(52) U.S. Cl.
USPC ........ 435/196; 435/147; 435/183; 435/252.3; 435/320.1; 536/23.2

(58) Field of Classification Search
None
See application file for complete search history.

(56) References Cited

U.S. PATENT DOCUMENTS

| 3,974,082 A | 8/1976 | Weyn |
| 4,444,886 A | 4/1984 | Esders et al. |
| 4,585,150 A | 4/1986 | Beacham et al. |
| 5,108,457 A | 4/1992 | Poulose et al. |
| 5,116,575 A | 5/1992 | Badertscher et al. |
| 5,281,525 A | 1/1994 | Mitsushima et al. |
| 5,296,161 A | 3/1994 | Wiersema et al. |
| 5,338,676 A | 8/1994 | Mitsushima et al. |
| 5,364,554 A | 11/1994 | Stanislowski et al. |
| 5,398,846 A | 3/1995 | Corba et al. |
| 5,528,152 A | 6/1996 | Hinoshita et al. |
| 5,552,018 A | 9/1996 | Devenyns |
| 5,624,634 A | 4/1997 | Brougham et al. |
| 5,683,724 A | 11/1997 | Hei et al. |
| 5,932,532 A | 8/1999 | Ghosh et al. |
| 6,183,807 B1 | 2/2001 | Gutzmann et al. |
| 6,210,639 B1 | 4/2001 | Vlass et al. |
| 6,319,888 B2 | 11/2001 | Wei et al. |
| 6,391,840 B1 | 5/2002 | Thompson et al. |
| 6,465,233 B1 | 10/2002 | Knauseder et al. |
| 6,518,307 B2 | 2/2003 | McKenzie et al. |
| 6,545,047 B2 | 4/2003 | Gutzmann et al. |
| 6,645,233 B1 | 11/2003 | Ayers et al. |
| 6,995,125 B2 | 2/2006 | Dasque et al. |
| 7,384,787 B2 | 6/2008 | Kazlauskas et al. |
| 7,550,420 B2 | 6/2009 | DiCosimo et al. |
| 7,723,083 B2 | 5/2010 | DiCosimo et al. |
| 7,807,425 B2 | 10/2010 | DiCosimo et al. |
| 7,829,315 B2 | 11/2010 | DiCosimo et al. |
| 7,910,347 B1 | 3/2011 | DiCosimo et al. |
| 7,923,233 B1 | 4/2011 | DiCosimo et al. |
| 7,927,854 B1 | 4/2011 | DiCosimo et al. |
| 7,932,072 B1 | 4/2011 | DiCosimo et al. |
| 7,951,566 B2 | 5/2011 | DiCosimo et al. |
| 7,951,567 B2 | 5/2011 | DiCosimo et al. |
| 7,960,151 B1 | 6/2011 | DiCosimo et al. |
| 7,960,528 B1 | 6/2011 | DiCosimo et al. |
| 7,964,378 B2 | 6/2011 | DiCosimo et al. |
| 7,964,383 B1 | 6/2011 | DiCosimo et al. |
| 7,981,643 B2 | 7/2011 | DiCosimo et al. |
| 7,981,644 B2 | 7/2011 | DiCosimo et al. |
| 2003/0026846 A1 | 2/2003 | Hei et al. |
| 2005/0008526 A1 | 1/2005 | Bianchetti et al. |
| 2005/0139608 A1 | 6/2005 | Muehlhausen et al. |
| 2008/0176299 A1 | 7/2008 | DiCosimo et al. |
| 2008/0176783 A1 | 7/2008 | DiCosimo et al. |
| 2009/0005590 A1 | 1/2009 | DiCosimo et al. |
| 2009/0311763 A1 | 12/2009 | DiCosimo et al. |
| 2009/0312420 A1 | 12/2009 | DiCosimo et al. |
| 2009/0325266 A1 | 12/2009 | DiCosimo et al. |
| 2010/0041752 A1 | 2/2010 | DiCosimo et al. |
| 2010/0086510 A1 | 4/2010 | DiCosimo et al. |

(Continued)

FOREIGN PATENT DOCUMENTS

| EP | 0807156 B1 | 11/1997 |
| EP | 1040222 B1 | 10/2000 |

(Continued)

OTHER PUBLICATIONS

Accession Q9WXT2. Oct. 31, 2012.*
Degrassi et al. Microbiology (2000), 146, 1585-1591.*
Drzewiecki et al. Microb Biotechnol. Jan. 2010;3(1):84-92. Epub Sep. 18, 2009.*
Abbott et al., "Physical Properties and Kinetic Behavior of a Cephalosporin Acetylesterase Produced by Bacillus . . . ", Appl. Microbiol., vol. 30, pp. 413-419 (1975).

(Continued)

Primary Examiner — Christian Fronda

(57) ABSTRACT

A two-stage heat treatment process is provided to improve the processability of recombinant microbial biomass comprising an enzyme having perhydrolytic activity. More specifically, a process is provided to treat the recombinant microbial biomass comprising a *Thermotoga* sp. acetyl xylan esterase having perhydrolytic activity such that microfiltration may be used to partially-purify and/or concentrate protein preparations. The acetyl xylan esterase may be used to produce peroxycarboxylic acids suitable for use in a variety of applications such as cleaning, disinfecting, sanitizing, bleaching, wood pulp processing, and paper pulp processing applications.

18 Claims, 23 Drawing Sheets

(56) References Cited

U.S. PATENT DOCUMENTS

| | | |
|---|---|---|
| 2010/0086621 A1 | 4/2010 | DiCosimo et al. |
| 2010/0087529 A1 | 4/2010 | DiCosimo et al. |
| 2010/0168234 A1 | 7/2010 | DiCosimo et al. |
| 2010/0168235 A1 | 7/2010 | DiCosimo et al. |
| 2010/0168236 A1 | 7/2010 | DiCosimo et al. |
| 2010/0168237 A1 | 7/2010 | DiCosimo et al. |
| 2011/0150857 A1 | 6/2011 | DiCosimo et al. |
| 2011/0152368 A1 | 6/2011 | DiCosimo et al. |

FOREIGN PATENT DOCUMENTS

| | | |
|---|---|---|
| WO | WO 97/30160 A1 | 8/1997 |
| WO | WO 00/11713 A1 | 2/2000 |
| WO | WO 00/61713 A1 | 10/2000 |
| WO | WO 2004/058961 A1 | 7/2004 |
| WO | WO 2007/070609 A1 | 6/2007 |
| WO | WO 2008/073139 A1 | 6/2008 |
| WO | WO 2010/019544 A1 | 2/2010 |
| WO | WO 2010/039953 A1 | 4/2010 |
| WO | WO 2010/039958 A1 | 4/2010 |
| WO | WO 2010/039960 A1 | 4/2010 |

OTHER PUBLICATIONS

Altschul et al., "Basic Local Alignment Search Tool", J. Mol. Biol., vol. 215, pp. 403-410 (1990).
Bernhardt et al., "Molecular basis of perhydrolase activity in Serine hydrolases", Enzyme Catalysis, vol. 44, pp. 2742-2746 (2005).
Chica et al., "Semi-rational approaches to engineering enzyme activity . . . ", Curr. Opin. Biotechnol., vol. 16, pp. 378-384 (2005).
Cardoza et al., "A Cephalosporin C Acetylhydrolase is Present in the Culture of Nocardia Lactamdurans", Appl. Microbiol. Biotechnol., vol. 54, pp. 406-412 (2000).
Copeland et al., "Thermatogal lettingae acetyl xylan transferase", A8F440_THELT, XP002501372, Nov. 13, 2007.
Degrassi et al., "The Acetyl Xylan Esterase of *Bacillus pumilus* Belongs to a Family of Esterases with Broad Substrate Specificity", Microbiology, vol. 146, pp. 1585-1591 (2000).
Deshpande et al., "Ethanol Production from Cellulose by Coupled Saccharification/ Fermentation . . . ", Appl. Biochem. Biotechnol., vol. 36, pp. 227-234 (1992).
Gabrielson et al., "Evaluation of Redox Indicators and the Use of Digital Scanners and . . . Growth in Microplates", J. Microbiol. Methods, vol. 50, pp. 63-73 (2002).
Genbank Accession No. NP_227893.1. (1999).
Guo et al., "Protein tolerance to random amino acid change" PNAS, vol. 101, pp. 9205-9210 (2004).
Higgins et al., "Fast and Sensitive Multiple Sequence Alignments on a Microcomputer", CABIOS, vol. 5, pp. 151-153 (1989).
Pinkernell et al., "Simultaneous HPLC Determination of Peroxyacetic Acid and Hydrogen Peroxide" Anal. Chem., 69(17):3623-3627 (1997).
Kirk et al. Enzyme Catalyzed Degradation and Formation of Peroxycarboxylic Acids, Biocatalysis, vol. 11, pp. 65-77 (1994).
Lennon et al., "The I.M.A.G.E. Consortium: An Integrated Molecular Analysis of Genomes and Their Expression", Genomics, vol. 33, pp. 151-152 (1996).
Lorenz et. al., "Isolation, Analysis and Expression of two Genes from *Thermoanaerobacterium* Sp. Strain . . . ", Bacteriol, vol. 179, pp. 5436-5441 (1997).
Minning et al., "Determination of Peracid and Putative Enzymatic Peracid Formation by an Easy Calorimetric Assay", Analytica Chimica Acta, vol. 378, pp. 293-298 (1999).
Mitsushima et al., "Gene cloning,, nucleotide sequence, and expression of a cephalosporin-C deacetylase . . . " Appl. Environ. Microbiol., vol. 61, pp. 2224-2229 (1995).

Mitsushima et al, NCBI Gen. Id. No. 550075, Gene Cloning, Nucleotide Sequence & Expression Accession No. BAA01729.1, pp. 1-2 (1999).
Payne et al., "Use of Alkaline Phosphatase Fusions to Studt Protein Secretion in *Bacillus subtilis*", J. Bacteriol., vol. 173, pp. 2278-2282 (1991).
Pearson, "Searching Protein Sequence Databases is Optimal Best?" Comput. Methods Genome Res., [Proc. Int. Symp.] (1994), Meeting Date 1992, pp. 111-120.
Politino et al., "Purification and Characterization of a Cephalosporin Esterase from Rhodosporidium Toruloides", Appl. Environ. Microbiol., vol. 63, 4807-4811 (1997).
Rey et al., "Complete Genome Sequence of the Industrial Bacterium *Bacillus licheniformis* and Comparisons with . . . ", Genome Biol., vol. 5, pp. 1-13 (2004).
Sakai, et al., "Purification and Properties of Cephalosporin-C Deacetylase from the Yeast . . . ", J. Ferment Bioeng., vol. 85, pp. 53-57 (1998).
Seffernick et al., "Melamine deaminase and atrozine chlorohydrolase . . . ", J. Bacteriol., vol. 183, pp. 2405-2410 (2001).
Sulter et al., "Proliferation and Metabolic Significance of Peroxisomes in Canadian . . . ", Arch. Microbiol., vol. 153, pp. 485-489 (1990).
Takami et al., "Complete Genome Sequence of the . . . Bacterium *Bacillus halodurans* & Genomic Sequence Comparison with . . . ", NAR, vol. 28, pp. 4317-4331 (2000).
Vincent et al., "Multifunctional xylooligosaccharide/cephalosporin C deacetylase revealed", J. Mol. Biol., vol. 330, pp. 593-606 (2003).
Witkowski et al., "Conversion of a beta-ketoacyl synthase to a malonyl decarboxylase . . . ", Biochemistry, vol. 38, pp. 11643-11650 (1999).
DiCosimo et al., "Thermophilic perhydrolases for peracetic acid production",Internet Citation, XP0002557717, Jul. 30, 3009.
International Search Report in PCT/US2006/047632, mailed Jul. 16, 2007.
International Search Report in PCT/US2007/010644, mailed Jan. 18, 2008.
International Search Report in PCT/US2008/067712, mailed Jan. 16, 2009.
U.S. Appl. No. 12/538,525, filed Aug. 10, 2009, Robert DiCosimo et al.
U.S. Appl. No. 13/070,123, filed Mar. 23, 2011, Robert DiCosimo et al.
U.S. Appl. No. 13/070,130, filed Mar. 23, 2011, Robert DiCosimo et al.
U.S. Appl. No. 13/070,135, filed Mar. 23, 2011, Robert DiCosimo et al.
U.S. Appl. No. 13/070,144, filed Mar. 23, 2011, Robert DiCosimo et al.
U.S. Appl. No. 13/070,149, filed Mar. 23, 2011, Robert DiCosimo et al.
U.S. Appl. No. 13/087,800, filed Apr. 15, 2011, Robert DiCosimo et al.
Deshpande, "Ethanol production from cellulose by coupled saccharification/fermentation using Saccharomyces . . . ", Appl. Biochem. Biotechnol., vol. 36, pp. 227-34 (1992).
Gabrielson et al., "Evaluation of redox indicators and the use of digital scanners and spectrophotometer . . . ", J. Microbiol. Methods, vol. 50, pp. 63-73 (2002).
Minning et al., "Determination of Peracid and Putative Enzymatic Peracid Formation by an Easy Colorimetric Assay", Analytica Chimica Acta, vol. 378, pp. 293-298 (1999).
Mitsushima et al., "Gene cloning, nucleotide sequence, and expression of a cephalosporin-C deacetylase from . . . " Appl. Environ. Microbiol., vol. 61, pp. 2224-2229 (1995).
GENBANK Accession No. NP_227893.1, (1999).

* cited by examiner

FACILITATED PROCESS FOR PURIFICATION OF PROTEINS

CROSS-REFERENCE TO RELATED APPLICATION

This application claims benefit of U.S. Provisional Patent Application No. 61/341,109, filed Mar. 26, 2010, which is incorporated by reference herein in its entirety.

TECHNICAL FIELD

The invention relates to the field of recombinant microbial biomass processing and enzyme purification. More specifically, a process is provided to improve the ability to partially-purify and/or concentrate a *Thermotoga* sp. acetyl xylan esterase having perhydrolytic activity using microfiltration.

BACKGROUND

Peroxycarboxylic acid compositions can be effective antimicrobial agents. Methods of using peroxycarboxylic acids to clean, disinfect, and/or sanitize hard surfaces, textiles, meat products, living plant tissues, and medical devices against undesirable microbial growth have been described (U.S. Pat. No. 6,545,047; U.S. Pat. No. 6,183,807; U.S. Pat. No. 6,518,307; U.S. Patent Application Publication No. 2003-0026846; and U.S. Pat. No. 5,683,724). Peroxycarboxylic acids have also been used in a various bleaching applications including, but not limited to, wood pulp bleaching/delignification and laundry care applications (European Patent 1040222B1; U.S. Pat. Nos. 5,552,018; 3,974,082; 5,296,161; and 5,364,554). The desired efficacious concentration of peroxycarboxylic acid may vary according to the product application (for example, ca. 500 ppm to 1000 ppm for medical instrument disinfection at neutral pH, ca. 30 ppm to 80 ppm for laundry bleaching or disinfection applications) in 1 min to 5 min reaction time at neutral to alkaline pH.

Enzymes structurally classified as members of family 7 of the carbohydrate esterases (CE-7) have been employed as perhydrolases to catalyze the reaction of hydrogen peroxide (or alternative peroxide reagent) with alkyl esters of carboxylic acids in water at a basic to acidic pH range (from ca. pH 10 to ca. pH 5) to produce an efficacious concentration of a peroxycarboxylic acid for such applications as disinfection (such as medical instruments, hard surfaces, textiles), bleaching (such as wood pulp or paper pulp processing/delignification, textile bleaching and laundry care applications), and other laundry care applications such as destaining, deodorizing, and sanitization (Published U.S. Patent Application Nos. 2008-0176783, 2008-0176299, 2009-0005590, and 2010-0041752 to DiCosimo et al.). The CE-7 enzymes have been found to have high specific activity for perhydrolysis of esters, particularly acetyl esters of alcohols, diols and glycerols. Published U.S. Patent Application No. 2010-0087529 to DiCosimo et al. describes several variant CE-7 perhydrolases derived from several *Thermotoga* sp. having higher perhydrolytic specific activity and/or improved selectivity for perhydrolysis when used to prepare peroxycarboxylic acid from carboxylic acid esters. One of the variants described in Published U.S. Patent Application No. 2010-0087529, *Thermotoga maritima* C277S, exhibited a significant improvement in specific activity relative to the *T. maritima* wild-type enzyme.

Recombinant microbial production of an enzyme often includes one or more downstream biomass processing steps used to partially or completely purify and/or concentrate the recombinant enzyme from other components of the biomass. However, considerable difficulty has been encountered when filtering or concentrating protein preparations on microfiltration membranes. The purpose of the filtration is to pass a solution containing the perhydrolase through the membranes while retaining particles greater than 0.2 microns or 0.45 microns in the retentate. The protein is often retained, at least in part, by the membrane, rather than passing through it, where the porosity of the membrane is such that the protein should freely pass through it.

One of the biomass components that may be adversely impacting the ability to recovery and/or concentrate the desired enzyme catalyst is the presence of DNA in the cell homogenate. However, the addition of an exogenous deoxyribonuclease (DNAse) may not be cost effective, especially for industrial scale fermentations, and the use of mammalian sources of DNAse may be undesirable in toll fermentation.

The problem to be solved is to provide a facile and cost-effective process to obtain a concentrate comprising a recombinant enzyme having perhydrolytic activity, preferably a process that does not include the use of an exogenous deoxyribonuclease.

SUMMARY

The problem has been solved by providing a two-stage heat treatment process suitable for treating microbial cell homogenate comprising at least one thermophilic enzyme having perhydrolytic activity. The insoluble components in the heat-treated microbial cell homogenate are removed and resulting solution containing the perhydrolytic enzyme is subsequently concentrated to produce a concentrate comprising the perhydrolytic enzyme.

In one embodiment, a process is provided comprising:

a) providing a microbial cell homogenate comprising soluble and insoluble components, wherein said microbial cell homogenate comprises a recombinantly-produced thermophilic enzyme having perhydrolytic activity;

b) subjecting the microbial cell homogenate to a first heat treatment ranging from at least 4 hours but no more than 24 hours at a temperature ranging from 40° C. to 65° C.;

c) subjecting the heat-treated microbial cell homogenate from step b) to a second heat treatment ranging from 5 minutes to 4 hours at a temperature ranging from 75° C. to 85° C.;

d) removing the insoluble components from the microbial cell homogenate obtained after performing step (b) and step (c) by centrifugation or filtration to obtain a solution comprising the recombinantly-produced thermophilic enzyme having perhydrolytic activity; and e) concentrating the solution comprising the thermophilic enzyme of step (d) by filtration, evaporation or a combination of protein precipitation and redissolution whereby a concentrate is obtained comprising the recombinant thermophilic enzyme having perhydrolytic activity.

In another embodiment, the microbial cell homogenate of step (a) is an *Escherichia coli* cell homogenate.

In another embodiment, an exogenous nuclease is not present in steps (a) through (d).

In another embodiment, the removal of the solid components from the microbial cell homogenate obtained after performing step (b) and step (c) is performed in step (d) using filtration.

In another embodiment, the removal of the solid components from the microbial cell homogenate obtained after performing step (b) and step (c) is performed in step (d) using a membrane having size exclusion cutoffs ranging from 0.45 microns to 0.20 microns.

In another embodiment, the membrane used in step (d) retains insoluble particles with an average diameter greater than 0.2 microns.

In another embodiment, the removal of the insoluble components from the microbial cell homogenate obtained after performing step (b) and step (c) is performed in step (d) using centrifugation.

In another embodiment, the concentration of the solution produced in step (d) is performed in step (e) using filtration.

In another embodiment, the concentration of the solution produced in step (d) is performed in step (e) using a membrane having size exclusion cutoffs ranging from 100 kDa to 30 kDa.

In another embodiment, the concentration of the solution produced in step (d) is performed in step (e) using evaporation.

In another embodiment, the concentration of the solution produced in step (d) is performed in step (e) using a combination of protein precipitation and redissolution.

In another embodiment, the recombinantly-produced thermophilic enzyme comprises a CE-7 signature motif comprising:

an RGQ motif corresponding to amino acid positions 118-120 of SEQ ID NO: 8;

a GXSQG motif corresponding to amino acid positions 186-190 of SEQ ID NO: 8; and an HE motif corresponding to amino acid positions 303-304 of SEQ ID NO: 8.

In another embodiment, the thermophilic enzyme having perhydrolytic activity is an acetyl xylan esterase derived from a *Thermotoga* sp. In another embodiment, the thermophilic enzyme comprises an amino acid sequence selected from the group consisting of SEQ ID NOs 2, 3, 4, 5, 6, 8, 9, 10, 11, 12, 13, 14, 15, 16, 17, 18, 19, 20, 21, 22, 24, 25, 26, 27, 28, 30, 31, 32, 33, 34, 36, 37, 38, 39, 40, 42, 43, 44, 45, and 46.

BRIEF DESCRIPTION OF THE FIGURES

(FIG. 1A) crude lysate, (FIG. 1B) lysate after incubation at 50° C., (FIG. 1C) lysate after incubation at 50° C. and heat-treatment at 75° C., and (FIG. 1D) lysate after heat-treatment at 75° C. (no 50° C. incubation). All chromatograms have same vertical scale, from −100 to +4500 mAU. (FIG. 2A) homogenization and incubation at 50° C., (FIG. 2B) incubation at 50° C. and homogenization, and (FIG. 2C) incubation at 50° C. followed by homogenization and subsequent heat treatment at 75° C. All chromatograms have same vertical scale, from −100 to +4500 mAU.

BRIEF DESCRIPTION OF THE BIOLOGICAL SEQUENCES

Figure 1A:
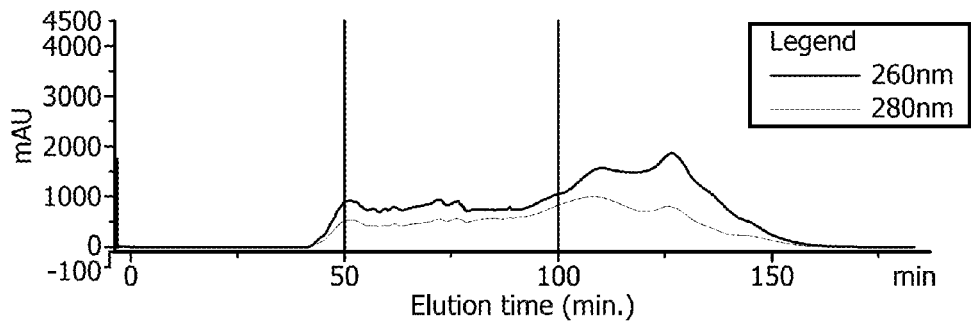
FIGS. 1A through 1D. Chromatograms of lysate supernatants after different processing steps.
Figure 1B:
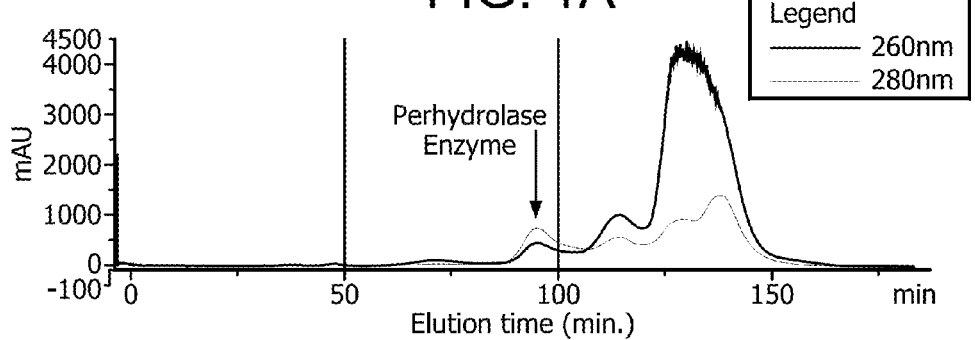
Figure 1C:
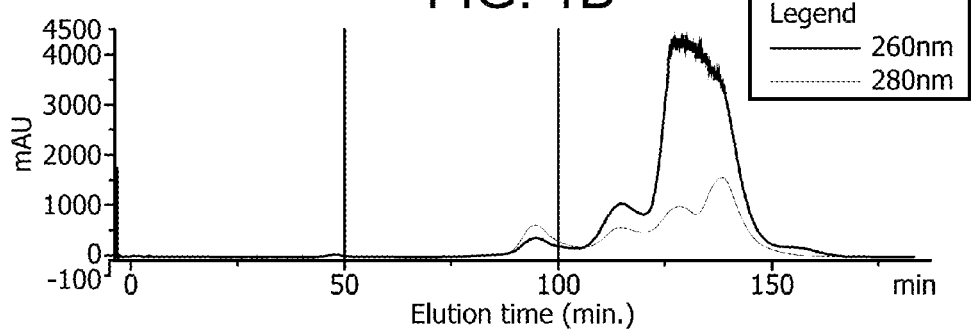
Figure 1D:
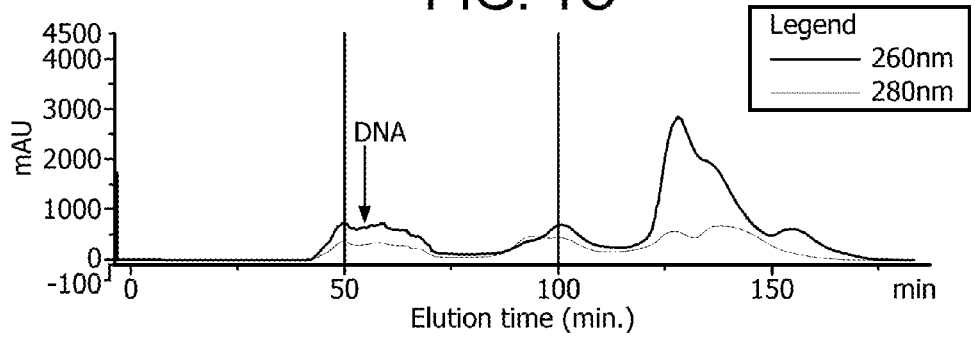

The following sequences comply with 37 C.F.R. §§1.821-1.825 ("Requirements for Patent Applications Containing Nucleotide Sequences and/or Amino Acid Sequence Disclosures—the Sequence Rules") and are consistent with World Intellectual Property Organization (WIPO) Standard ST. 25 (1998) and the sequence listing requirements of the European Patent Convention (EPC) and the Patent Cooperation Treaty (PCT) Rules 5.2 and 49.5 (a-bis), and Section 208 and Annex C of the Administrative Instructions. The symbols and format used for nucleotide and amino acid sequence data comply with the rules set forth in 37 C.F.R. §1.822.

TABLE 1

A non-comprehensive list of CE-7 carbohydrate esterases having perhydrolytic activity and their associated sequence identification numbers. The members in the list are derived from thermophilic microorganisms (e.g., *Thermotoga* sp.).

| Enzyme ID | Nucleic acid[1] sequence (SEQ ID NO:) | Amino acid sequence (SEQ ID NO:) | Reference |
|---|---|---|---|
| *Thermotoga neapolitana* WT | 1 | 2 | US 2008-0176783 |
| *T. neapolitana* C277A | — | 3 | US 2010-0087529 |
| *T. neapolitana* C277V | — | 4 | US 2010-0087529 |
| *T. neapolitana* C277S | — | 5 | US 2010-0087529 |
| *T. neapolitana* C277T | — | 6 | US 2010-0087529 |
| *Thermotoga maritima* WT | 7 | 8 | US 2008-0176783 |
| *T. maritima* C277A | — | 9 | US 2010-0087529 |
| *T. maritima* C277V | — | 10 | US 2010-0087529 |
| *T. maritima* C277S | — | 11 | US 2010-0087529 |
| *T. maritima* C277T | — | 12 | US 2010-0087529 |
| *T. maritima* F24I/S35T/Q179L/N275D/C277S/S308G/F317S | — | 13 | US 12/632,438 |
| *T. maritima* N275D/C277S | — | 14 | US 12/632,438 |
| *T. maritima* C277S/F317S | — | 15 | US 12/632,438 |
| *T. maritima* S35T/C277S | — | 16 | US 12/632,438 |
| *T. maritima* Q179L/C277S | — | 17 | US 12/632,438 |
| *T. maritima* L8R/L125Q/Q176L/V183D/F247I/C277S/P292L | — | 18 | Co-pending US provisional attorney docket number CL5035 |
| *T. maritima* K77E/A266E/C277S | — | 19 | Co-pending US provisional attorney docket number CL5035 |
| *T. maritima* F27Y/I149V/A266V/C277S/I295T/N302S | — | 20 | Co-pending US provisional attorney docket number CL5035 |
| *T. maritima* L195Q/C277S | — | 21 | Co-pending US provisional attorney docket number CL5035 |
| *T. maritima* Y110F/C277S | — | 22 | Co-pending US provisional attorney docket number CL5035 |

TABLE 1-continued

A non-comprehensive list of CE-7 carbohydrate esterases having perhydrolytic activity and their associated sequence identification numbers. The members in the list are derived from thermophilic microorganisms (e.g., *Thermotoga* sp.).

| Enzyme ID | Nucleic acid[1] sequence (SEQ ID NO:) | Amino acid sequence (SEQ ID NO:) | Reference |
|---|---|---|---|
| *Thermotoga lettingae* WT | 23 | 24 | US 2009-0005590 |
| *T. lettingae* C277A | — | 25 | US 2010-0087529 |
| *T. lettingae* C277V | — | 26 | US 2010-0087529 |
| *T. lettingae* C277S | — | 27 | US 2010-0087529 |
| *T. lettingae* C277T | — | 28 | US 2010-0087529 |
| *Thermotoga petrophila* WT | 29 | 30 | US 2009-0005590 |
| *T. petrophila* C277A | — | 31 | US 2010-0087529 |
| *T. petrophila* C277V | — | 32 | US 2010-0087529 |
| *T. petrophila* C277S | — | 33 | US 2010-0087529 |
| *T. petrophila* C277T | — | 34 | US 2010-0087529 |
| *Thermotoga* sp. RQ2(a) WT | 35 | 36 | US 2009-0005590 |
| *Thermotoga* sp. RQ2(a) C277A | — | 37 | US 2010-0087529 |
| *Thermotoga* sp. RQ2(a) C277V | — | 38 | US 2010-0087529 |
| *Thermotoga* sp. RQ2(a) C277S | — | 39 | US 2010-0087529 |
| *Thermotoga* sp. RQ2(a) C277T | — | 40 | US 2010-0087529 |
| *Thermotoga* sp. RQ2 (b) WT | 41 | 42 | US 2009-0005590 |
| *Thermotoga* sp. RQ2 (b) C278A | — | 43 | US 2010-0087529 |
| *Thermotoga* sp. RQ2 (b) C278V | — | 44 | US 2010-0087529 |
| *Thermotoga* sp. RQ2 (b) C278S | — | 45 | US 2010-0087529 |
| *Thermotoga* sp. RQ2 (b) C278T | — | 46 | US 2010-0087529 |

[1] = codon optimized for recombinant expression in *E. coli*.
Polynucleotide sequences encoding wild type polypeptide sequences are provided. WT = wild-type CE-7 carbohydrate esterase.

SEQ ID NOs: 47, 48, 50, and 51 are the nucleic acid sequences primers used in Example 1.

SEQ ID NO: 49 is the nucleic acid sequence of the polynucleotide prepared using PCR primers SEQ ID NO: 47 and SEQ ID NO: 48.

SEQ ID NO: 52 is the nucleic acid sequence of the polynucleotide prepared using PCR primers SEQ ID NO: 50 and SEQ ID NO: 51.

SEQ ID NOs: 53-60 are the sequences of oligonucleotides used to prepare *T. maritime* variants C277V, C277A, C277S, and C277T.

DETAILED DESCRIPTION

The present process comprising two heat-treatment steps is used to aid in purifying and/or concentrating a thermophilic enzyme having perhydrolytic activity such that the ease of filterability of the enzyme through a membrane is enabled or enhanced.

In this disclosure, a number of terms and abbreviations are used. The following definitions apply unless specifically stated otherwise.

As used herein, the articles "a", "an", and "the" preceding an element or component of the invention are intended to be nonrestrictive regarding the number of instances (i.e., occurrences) of the element or component. Therefore "a", "an" and "the" should be read to include one or at least one, and the singular word form of the element or component also includes the plural unless the number is obviously meant to be singular.

The term "comprising" means the presence of the stated features, integers, steps, or components as referred to in the claims, but does not preclude the presence or addition of one or more other features, integers, steps, components or groups thereof. The term "comprising" is intended to include embodiments encompassed by the terms "consisting essentially of" and "consisting of". Similarly, the term "consisting essentially of" is intended to include embodiments encompassed by the term "consisting of".

As used herein, the term "about" modifying the quantity of an ingredient or reactant employed refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; and the like. The term "about" also encompasses amounts that differ due to different equilibrium conditions for a composition resulting from a particular initial mixture. Whether or not modified by the term "about", the claims include equivalents to the quantities.

Where present, all ranges are inclusive and combinable. For example, when a range of "1 to 5" is recited, the recited range should be construed as including ranges "1 to 4", "1 to 3", "1-2", "1-2 & 4-5", "1-3 & 5", and the like.

As used herein, the term "peroxycarboxylic acid" is synonymous with peracid, peroxyacid, peroxy acid, percarboxylic acid and peroxoic acid.

As used herein, the term "peracetic acid" is abbreviated as "PAA" and is synonymous with peroxyacetic acid, ethaneperoxoic acid and all other synonyms of CAS Registry Number 79-21-0.

As used herein, the terms "enzyme catalyst" and "perhydrolase catalyst" refer to a catalyst comprising an enzyme (i.e., a polypeptide) having perhydrolysis activity.

As used herein, the term "perhydrolysis" or "perhydrolytic reaction" is defined as the reaction of a selected substrate with a source of hydrogen peroxide to form a peroxycarboxylic acid. Typically, inorganic peroxide is reacted with the selected substrate in the presence of a catalyst having perhydrolytic activity to produce the peroxycarboxylic acid. As used herein, the term "chemical perhydrolysis" includes perhydrolysis reactions in which a substrate (such as a peroxycarboxylic acid precursor) is combined with a source of hydrogen peroxide wherein peroxycarboxylic acid is formed in the absence of an enzyme catalyst. As used herein, the term "enzymatic perhydrolysis" refers a reaction of a selected substrate with a source of hydrogen peroxide to form a peroxycarboxylic acid, wherein the reaction is catalyzed by an enzyme catalyst having perhydrolysis activity.

As used herein, the term "perhydrolase activity" refers to the enzyme catalyst activity per unit mass (for example, milligram) of protein, dry cell weight, or immobilized catalyst weight.

As used herein, "one unit of enzyme activity" or "one unit of activity" or "U" is defined as the amount of perhydrolytic activity required for the production of 1 μmol of peroxycarboxylic acid product (such as peracetic acid) per minute at a specified temperature. "One unit of enzyme activity" may also be used herein to refer to the amount of peroxycarboxylic acid hydrolysis activity required for the hydrolysis of 1 μmol of peroxycarboxylic acid (e.g., peracetic acid) per minute at a specified temperature.

As used herein, the term "exogenous nuclease" refers to the addition and/or presence of a non-endogenous enzyme that catalyzes the hydrolytic cleavage of phosphodiester linkages in the DNA backbone. Fermentation biomass processing often includes the exogenous addition of a commercially-available deoxyribonuclease, such as deoxyribonuclease I from bovine pancreas (DN25; Sigma Aldrich, St. Louis, Mo.), to the biomass to aid in the degradation of DNA. However, the addition of an exogenous nuclease may increases the cost of biomass process, and the use of mammalian sources of DNAse may be undesirable in toll fermentation. In one embodiment, an exogenous deoxyribonuclease is not used in the present process.

Preparation of Microbial Cell Homogenate

The present process comprises subjecting a microbial cell homogenate (comprising the recombinantly produced perhydrolytic enzyme) to two distinct heat treatment steps. As use herein, the term "microbial cell homogenate" comprises soluble and insoluble components obtained after lysing the host cell used to recombinantly produce the enzyme having perhydrolytic activity. Typically the homogenate comprises a substantially aqueous matrix where the relative concentration of the homogenate may be adjusted to a desired concentration prior to initiating the first heat treatment step. The microbial host cell may be lysed using any number of methods know in the art, such as chemical, enzymatic, mechanical lysis (e.g., French press or dairy homogenizer) or any combination thereof. The microbial cells and/or microbial cell homogenate may be pH adjusted and/or may include the addition of a buffer prior to the first heat treatment step. In a preferred aspect, the pH of the microbial cell homogenate may be adjusted to a pH of about 6.5 to about 7.5 prior to the first heat treatment. In a further aspect, a phosphate or bicarbonate buffer may be included. In a further embodiment, magnesium sulfate may also be present in the microbial cell homogenate, preferably at a concentration ranging from 0.1 to 10 mM, more preferably 2 mM.

Two-Stage Heat Treatment

The present process comprises two distinct heat treatment steps.

As used herein, the terms "heat treatment", "heat treatment period", "heat-treated", and "heating" are used to describe the process steps of subjecting a microbial cell homogenate to a specified temperature or temperature range for a specified period of time. The present process comprises a first heat treatment and a second heat treatment.

As used herein, the term "first heat treatment", "first heat-treatment period" or "incubation step" refers to a process step wherein the microbial cell homogenate comprising a recombinantly-produced thermophilic enzyme is subjected to a temperature range from about 40° C. to about 65° C. for a period of time ranging from 4 hours to 24 hours, preferably using a temperature range of about 45° C. to about 55° C. for about 4 hours to about 16 hours. Although not bound by theory, the conditions of the first heat-treatment step are selected such that the endogenous nucleases present in the homogenate are active for at least a portion or all of the first heat-treatment period. In one embodiment, an exogenous deoxyribonuclease (DNAse) is not present in the first and/or second heat treatment step.

As used herein, the term "second heat treatment" or "second heat-treatment period" refers to a process step wherein the resulting "heat-treated" microbial cell homogenate from the first heat treatment is subsequently subjected to a second heat treatment comprising a temperature range from about 75° C. to about 85° C. for a period of time ranging from about 5 minutes to about 24 hours, preferably using a temperature range of about 75° C. to about 85° C. for about 30 minutes to about 4 hours.

Removal of Insoluble Components after the Second Heat Treatment

The insoluble components in the heat-treated microbial cell homogenate may be separated from the soluble components using centrifugation or filtration. The resulting solution comprises the recombinantly produced thermophilic enzyme having perhydrolytic activity.

In one embodiment, the removal of the insoluble (solid) components from the microbial cell biomass obtained after the second heat treatment comprises filtration using a membrane having size exclusion cut-offs ranging from 0.45 microns to 0.20 microns. In a preferred aspect, the membrane retains particles greater than 0.2 microns in average diameter.

The perhydrolytic enzyme in the resulting solution is then concentrated by filtration, evaporation or a combination of protein precipitation and redissolution whereby a concentrate is obtained comprising the recombinant thermophilic enzyme having perhydrolytic activity.

In one embodiment, filtration is used to concentrate the solution after the insoluble components are removed. In another embodiment, the filtration step used to concentrate the solution uses a membrane having a size exclusion cut-off range from 100 kDa to 30 kDa.

In another embodiment, evaporation is used to concentrate the solution after the insoluble components are removed in step (d).

In another embodiment, a combination of protein precipitation and redissolution is used to produce a concentrate from the solution obtained from step (d).

In one embodiment, the weight percent (wt %) of the recombinant thermophilic enzyme having perhydrolytic activity in the concentrate is at least 2.5 wt %. In a preferred embodiment, the weight percent (wt %) of the recombinant thermophilic enzyme having perhydrolytic activity in the concentrate is at least 5.0 wt %.

Carbohydrate Esterases (Family 7) Having Perhydrolytic Activity

Members of the CE-7 family include cephalosporin C deacetylases (CAHs; E.C. 3.1.1.41) and acetyl xylan esterases (AXEs; E.C. 3.1.1.72). Members of the CE-7 esterase family share a conserved signature motif (Vincent et al., *J. Mol. Biol.*, 330:593-606 (2003)). As used herein, the terms "signature motif" and "CE-7 signature motif", refer to conserved structures shared among a family of enzymes having a perhydrolytic activity.

As used herein, "structurally classified as a CE-7 enzyme", "structurally classified as a carbohydrate esterase family 7 enzyme", "structurally classified as a CE-7 carbohydrate esterase", and "CE-7 perhydrolase" will be used to refer to enzymes having perhydrolysis activity that are structurally classified as a CE-7 carbohydrate esterase based on the presence of the CE-7 signature motif (Vincent et al., supra). As used herein, the "signature motif" for CE-7 esterases comprises three conserved motifs (residue position numbering relative to reference sequence SEQ ID NO: 2; the wild-type *Thermotoga maritime* acetyl xylan esterase):

a) Arg118-Gly119-Gln120;
b) Gly186-Xaa187-Ser188-Gln189-Gly190; and
c) His303-Glu304.

Typically, the Xaa at amino acid residue position 187 is glycine, alanine, proline, tryptophan, or threonine. Two of the three amino acid residues belonging to the catalytic triad are in bold. In one embodiment, the Xaa at amino acid residue position 187 is selected from the group consisting of glycine, alanine, proline, tryptophan, and threonine.

Further analysis of the conserved motifs within the CE-7 carbohydrate esterase family indicates the presence of an additional conserved motif (LXD at amino acid positions 272-274 of SEQ ID NO: 2) that may be used to further define a member of the CE-7 carbohydrate esterase family. In a further embodiment, the signature motif defined above includes a fourth conserved motif defined as:

Leu272-Xaa273-Asp274.

The Xaa at amino acid residue position 273 is typically isoleucine, valine, or methionine. The fourth motif includes the aspartic acid residue (bold) belonging to the catalytic triad (Ser188-Asp274-His303).

Perhydrolases comprising the CE-7 signature motif and/or a substantially similar structure are suitable for use in the present process as long as they enzyme is not permanently or substantially inactivated (i.e., loss of perhydrolytic activity) by the second temperature treatment conditions of present process. Means to identify substantially similar biological molecules are well known in the art (e.g. sequence alignment protocols, nucleic acid hybridizations, presence of a conserved signature motif, etc.). In one aspect, the enzyme catalyst may comprise a substantially similar enzyme having at least 40%, preferably at least 50%, more preferably at least 60%, even more preferable at least 70%, even more preferably at least 80%, yet even more preferable at least 90% identity, and most preferably at least 95% amino acid identity to the sequences provided herein.

As used herein, the terms "cephalosporin C deacetylase" and "cephalosporin C acetyl hydrolase" refer to an enzyme (E.C. 3.1.1.41) that catalyzes the deacetylation of cephalosporins such as cephalosporin C and 7-aminocephalosporanic acid (Mitsushima, Kenji, et al., Appl. Environ. Microbiol. (1995) 61(6):2224-2229). As described herein, several cephalosporin C deacetylases are provided having significant perhydrolysis activity.

As used herein, "acetyl xylan esterase" refers to an enzyme (E.C. 3.1.1.72; AXEs) that catalyzes the deacetylation of acetylated xylans and other acetylated saccharides. As illustrated herein, several enzymes classified as acetyl xylan esterases are provided having significant perhydrolase activity.

Members of the CE-7 carbohydrate esterase family comprising a CE-7 signature motif having excellent perhydrolytic activity for producing peroxycarboxylic acids for carboxylic acid ester substrates and a source of peroxygen, such as hydrogen peroxide (Published U.S. Patent Application Publication No. 2008-0176783 to DiCosimo et al). A host of variant enzymes derived from naturally occurring acetyl xylan esterases obtained from thermophilic microorganisms, such as members of the genus Thermotoga, have also been produced. A non-limiting list of perhydrolytic enzymes derived from a Thermotoga sp. acetyl xylan esterase are provided in Table 1.

Thermophilic Enzymes Having Perhydrolytic Activity

As used herein, the term "thermophilic enzyme having perhydrolytic activity" or "thermophilic perhydrolase" will refer to a carbohydrate esterase family 7 enzyme (cephalosporin deacetylases and acetyl xylan esterases) having perhydrolytic activity wherein the present heat-treatment process does not significantly impact the perhydrolytic activity of the enzyme. In one embodiment, the enzyme catalyst will be considered temperature stable (i.e., "a thermophilic enzyme") if subjecting the enzyme to the conditions of the second heat treatment step (i.e., exposure to an elevated temperature for a defined period of time) do not adversely impact the perhydrolytic activity of the enzyme. In another embodiment, the enzyme catalyst may be considered "temperature stable" (i.e., thermophilic) if exposure of the enzyme to a heat treatment period of 5 minutes to 4 hours at a temperature ranging from 75° C. to 85° C. does not significantly decrease the perhydrolytic activity of the enzyme.

In one embodiment, the thermophilic enzyme having perhydrolytic activity is an acetyl xylan esterase derived from a thermophilic microorganism, such as a species within the bacterial genus Thermotoga. In a further preferred embodiment, the thermophilic enzyme may be a variant of an acetyl xylan esterase from a thermophilic microorganism so long as the variant retains perhydrolytic activity after exposure to the conditions used in the second heat treatment. In a further preferred aspect, the thermophilic enzyme having perhydrolytic activity is an acetyl xylan esterase or variant thereof from Thermotoga maritima, Thermotoga neapolitana, Thermotoga lettingae, Thermotoga petrophila, and Thermotoga sp. RQ2. A non-limiting list of enzymes is provided in Table 1.

In yet another embodiment, the thermophilic enzyme having perhydrolytic activity comprises an amino acid sequence selected from the group consisting of SEQ ID NOs: 2, 3, 4, 5, 6, 8, 9, 10, 11, 12, 13, 14, 15, 16, 17, 18, 19, 20, 21, 22, 24, 25, 26, 27, 28, 30, 31, 32, 33, 34, 36, 37, 38, 39, 40, 42, 43, 44, 45, and 46.

In a preferred embodiment, the thermophilic enzyme is recombinantly expressed in a microbial host cell. Examples of host strains include, but are not limited to, bacterial, fungal or yeast species such as *Aspergillus, Trichoderma, Saccharomyces, Pichia, Phaffia, Kluyveromyces, Candida, Hansenula, Yarrowia, Salmonella, Bacillus, Acinetobacter, Zymomonas, Agrobacterium, Erythrobacter, Chlorobium, Chromatium, Flavobacterium, Cytophaga, Rhodobacter, Rhodococcus, Streptomyces, Brevibacterium, Corynebacteria, Mycobacterium, Deinococcus, Escherichia, Erwinia, Pantoea, Pseudomonas, Sphingomonas, Methylomonas, Methylobacter, Methylococcus, Methylosinus, Methylomicrobium, Methylocystis, Alcaligenes, Synechocystis, Synechococcus, Anabaena, Thiobacillus, Methanobacterium, Klebsiella*, and *Myxococcus*. In a preferred embodiment, bacterial host strains include *Escherichia, Bacillus*, and *Pseudomonas*. In a further preferred aspect, the bacterial host cell is *Escherichia coli*.

Carboxylic Acid Ester Substrates

The CE-7 enzymes having perhydrolytic activity can use a variety of carboxylic acid ester substrates (in the presence of a suitable source of peroxygen) to produce one or more peracids, such as peracetic acid.

Examples of carboxylic acid ester substrates may include, but are not limited to:

one or more esters provided by the following formula:

wherein X=an ester group of the formula $R_6C(O)O$ $R_6$=C1 to C7 linear, branched or cyclic hydrocarbyl moiety, optionally substituted with hydroxyl groups or C1 to C4 alkoxy groups, wherein $R_6$ optionally comprises one or more ether linkages for R6=C2 to C7;

$R_5$=a C1 to C6 linear, branched, or cyclic hydrocarbyl moiety optionally substituted with hydroxyl groups; wherein each carbon atom in $R_5$ individually comprises no more than one hydroxyl group or no more than one ester group; wherein $R_5$ optionally comprises one or more ether linkages;

m is an integer ranging from 1 to the number of carbon atoms in $R_5$; and wherein said esters have solubility in water of at least 5 ppm at 25° C.

In another embodiment, $R_6$ is C1 to C7 linear hydrocarbyl moiety, optionally substituted with hydroxyl groups or C1 to C4 alkoxy groups, optionally comprising one or more ether linkages. In a further preferred embodiment, $R_6$ is C2 to C7 linear hydrocarbyl moiety, optionally substituted with hydroxyl groups, and/or optionally comprising one or more ether linkages.

As used herein, the terms "hydrocarbyl", "hydrocarbyl group", and "hydrocarbyl moiety" mean a straight chain, branched or cyclic arrangement of carbon atoms connected by single, double, or triple carbon to carbon bonds and/or by ether linkages, and substituted accordingly with hydrogen atoms. Such hydrocarbyl groups may be aliphatic and/or aromatic. Examples of hydrocarbyl groups include methyl, ethyl, propyl, isopropyl, butyl, isobutyl, t-butyl, cyclopropyl, cyclobutyl, pentyl, cyclopentyl, methylcyclopentyl, hexyl, cyclohexyl, benzyl, and phenyl. In one embodiment, the hydrocarbyl moiety is a straight chain, branched or cyclic arrangement of carbon atoms connected by single carbon to carbon bonds and/or by ether linkages, and substituted accordingly with hydrogen atoms.

In another embodiment, suitable substrates also include one or more glycerides of the formula:

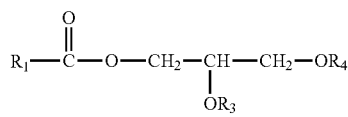

wherein $R_1$=C1 to C21 straight chain or branched chain alkyl optionally substituted with an hydroxyl or a C1 to C4 alkoxy group and $R_3$ and $R_4$ are individually H or $R_1C(O)$.

In another aspect, suitable substrates may also include one or more esters of the formula:

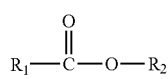

wherein $R_1$ is a C1 to C7 straight chain or branched chain alkyl optionally substituted with an hydroxyl or a C1 to C4 alkoxy group and $R_2$ is a C1 to C10 straight chain or branched chain alkyl, alkenyl, alkynyl, aryl, alkylaryl, alkylheteroaryl, heteroaryl, $(CH_2CH_2O)_n$, or $(CH_2CH(CH_3)—O)_nH$ and n is 1 to 10.

Suitable substrates may also include one or more acylated saccharides selected from the group consisting of acylated mono-, di-, and polysaccharides. In another embodiment, the acylated saccharides are selected from the group consisting of acetylated xylan, fragments of acetylated xylan, acetylated xylose (such as xylose tetraacetate), acetylated glucose (such as glucose pentaacetate), β-D-ribofuranose-1,2,3,5-tetraacetate, tri-O-acetyl-D-galactal, tri-O-acetyl-D-glucal, and acetylated cellulose. In a preferred embodiment, the acetylated saccharide is selected from the group consisting of β-D-ribofuranose-1,2,3,5-tetraacetate, tri-O-acetyl-D-galactal, tri-O-acetyl-D-glucal, and acetylated cellulose.

In another embodiment, suitable substrates are selected from the group consisting of: monoacetin; diacetin; triacetin; monopropionin; dipropionin; tripropionin; monobutyrin; dibutyrin; tributyrin; glucose pentaacetate; xylose tetraacetate; acetylated xylan; acetylated xylan fragments; β-D-ribofuranose-1,2,3,5-tetraacetate; tri-O-acetyl-D-galactal; tri-O-acetyl-D-glucal; monoesters or diesters of 1,2-ethanediol, 1,2-propanediol, 1,3-propanediol, 1,2-butanediol, 1,3-butanediol, 2,3-butanediol, 1,4-butanediol, 1,2-pentanediol, 2,5-pentanediol, 1,6-pentanediol, 1,2-hexanediol, 2,5-hexanediol, 1,6-hexanediol; and mixtures thereof.

In another embodiment, the carboxylic acid ester is selected from the group consisting of monoacetin, diacetin, triacetin, and combinations thereof. In another embodiment, the substrate is a C1 to C6 polyol comprising one or more ester groups. In a preferred embodiment, one or more of the hydroxyl groups on the C1 to C6 polyol are substituted with one or more acetoxy groups (such as 1,3-propanediol diacetate, 1,4-butanediol diacetate, etc.). In a further embodiment, the substrate is propylene glycol diacetate (PGDA), ethylene glycol diacetate (EGDA), or a mixture thereof.

In another embodiment, suitable substrates are selected from the group consisting of ethyl acetate; methyl lactate; ethyl lactate; methyl glycolate; ethyl glycolate; methyl methoxyacetate; ethyl methoxyacetate; methyl 3-hydroxybutyrate; ethyl 3-hydroxybutyrate; triethyl 2-acetyl citrate; glucose pentaacetate; gluconolactone; glycerides (mono-, di-, and triglycerides) such as monoacetin, diacetin, triacetin, monopropionin, dipropionin (glyceryl dipropionate), tripropionin (1,2,3-tripropionylglycerol), monobutyrin, dibutyrin (glyceryl dibutyrate), tributyrin (1,2,3-tributyrylglycerol); acetylated saccharides; and mixtures thereof.

In a further embodiment, suitable substrates are selected from the group consisting of monoacetin, diacetin, triacetin, monopropionin, dipropionin, tripropionin, monobutyrin, dibutyrin, tributyrin, ethyl acetate, and ethyl lactate. In yet another aspect, the substrate is selected from the group consisting of diacetin, triacetin, ethyl acetate, and ethyl lactate. In a most preferred embodiment, the suitable substrate comprises triacetin.

Method for Determining the Concentration of Peroxycarboxylic Acid and Hydrogen Peroxide.

A variety of analytical methods can be used in the present method to analyze the reactants and products including, but not limited to, titration, high performance liquid chromatography (HPLC), gas chromatography (GC), mass spectroscopy (MS), capillary electrophoresis (CE), the analytical procedure described by U. Karst et al. (*Anal. Chem.*, 69(17): 3623-3627 (1997)), and the 2,2'-azino-bis(3-ethylbenzothazoline)-6-sulfonate (ABTS) assay (S. Minning, et al., *Analytica Chimica Acta* 378:293-298 (1999) and WO 20041058961 A1) as described in U.S. Patent Application Publication No. 2008-0176783.

Recombinant Expression of a Perhydrolytic Enzyme

A variety of culture methodologies may be applied to produce the perhydrolase catalyst. Large-scale production of a specific gene product over expressed from a recombinant microbial host may be produced by batch, fed-batch or continuous culture methodologies. Batch and fed-batch culturing methods are common and well known in the art and examples may be found in Thomas D. Brock in *Biotechnology: A Textbook of Industrial Microbiology*, Second Edition, Sinauer Associates, Inc., Sunderland, Mass. (1989) and Deshpande, Mukund V., *Appl. Biochem. Biotechnol.*, 36:227 (1992).

In one embodiment, commercial production of the desired perhydrolase catalyst is accomplished with a continuous culture. Continuous cultures are an open system where a defined culture media is added continuously to a bioreactor and an equal amount of conditioned media is removed simultaneously for processing. Continuous cultures generally maintain the cells at a constant high liquid phase density where cells are primarily in log phase growth. Alternatively, continuous culture may be practiced with immobilized cells where carbon and nutrients are continuously added and valuable products, by-products or waste products are continuously removed from the cell mass. Cell immobilization may be performed using a wide range of solid supports composed of natural and/or synthetic materials.

Recovery of the desired perhydrolase catalyst from a batch or fed-batch fermentation, or continuous culture may be accomplished by any of the methods that are known to those skilled in the art. For example, when the enzyme catalyst is produced intracellularly, the cell paste is separated from the culture medium by centrifugation or membrane filtration, optionally washed with water or an aqueous buffer at a desired pH, then a suspension of the cell paste in an aqueous buffer at a desired pH is lysed or homogenized to produce a cell extract containing the desired enzyme catalyst.

When an amount, concentration, or other value or parameter is given either as a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope be limited to the specific values recited when defining a range.

General Methods

The following examples are provided to demonstrate preferred embodiments. It should be appreciated by those of skill in the art that the techniques disclosed in the examples which follow represent techniques discovered by the inventor to function well in the practice of the methods disclosed herein, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the presently disclosed methods.

All reagents and materials were obtained from DIFCO Laboratories (Detroit, Mich.), GIBCO/BRL (Gaithersburg, Md.), TCI America (Portland, Oreg.), Roche Diagnostics Corporation (Indianapolis, Ind.) or Sigma-Aldrich Chemical Company (St. Louis, Mo.), unless otherwise specified.

The following abbreviations in the specification correspond to units of measure, techniques, properties, or compounds as follows: "sec" or "s" means second(s), "min" means minute(s), "h" or "hr" means hour(s), "µL" means microliter(s), "mL" means milliliter(s), "L" means liter(s), "mM" means millimolar, "M" means molar, "mmol" means millimole(s), "ppm" means part(s) per million, "wt" means weight, "wt %" means weight percent, "g" means gram(s), "mg" means microgram(s), "ng" means nanogram(s), "g" means gravity, "HPLC" means high performance liquid chromatography, "dd $H_2O$" means distilled and deionized water, "dcw" means dry cell weight, "ATCC" or "ATCC®" means the American Type Culture Collection (Manassas, Va.), "U" means unit(s) of perhydrolase activity, "rpm" means revolution(s) per minute, "EDTA" means ethylenediaminetetraacetic acid, "slpm" means standard liters per minute, "IPTG" means isopropyl β-D-1-thiogalactopyranoside, "DTT" means dithiothreitol, "BCA" means bicinchoninic acid.

EXAMPLE 1

Cloning and Expression of Acetyl Xylan Esterase from *Thermotoga maritima*

A gene encoding acetyl xylan esterase from *T. maritima* (amino acid sequence SEQ ID NO: 8) as reported in GENBANK® (accession no. NP_227893.1) was synthesized (DNA 2.0, Menlo Park Calif.). The gene was subsequently amplified by PCR (0.5 min at 94° C., 0.5 min at 55° C., 1 min at 70° C., 30 cycles) using primers identified as SEQ ID NO: 47 and SEQ ID NO: 48. The resulting nucleic acid product (SEQ ID NO: 49) was cut with restriction enzymes PstI and XbaI and subcloned between the PstI and XbaI sites in pUC19 to generate the plasmid identified as pSW207. A gene encoding an acetyl xylan esterase from *T. maritima* as reported in GENBANK® (accession no. NP_227893.1; amino acid sequence SEQ ID NO: 8) was synthesized using codons optimized for expression in *E. coli* (DNA 2.0, Menlo Park Calif.). The gene was subsequently amplified by PCR (0.5 min at 94° C., 0.5 min at 55° C., 1 min at 70° C., 30 cycles) using primers identified as SEQ ID NO:50 and SEQ ID NO:51. The resulting nucleic acid product (SEQ ID NO: 52) was cut with restriction enzymes EcoRI and PstI and subcloned between the EcoRI and PstI sites in pTrc99A (GENBANK® accession no. M22744) to generate the plasmid identified as pSW228 (containing the codon-optimized *T. maritima* coding sequence SEQ ID NO: 7). The plasmids pSW207 and pSW228 were used to transform *E. coli* KLP18 (U.S. Patent Application Pub. No. 2008-0176299) to generate the strains identified as KLP18/pSW207 and KLP18/pSW228, respectively. KLP18/pSW207 and KLP18/pSW228 were grown in LB media at 37° C. with shaking up to $OD_{600nm}$=0.4-0.5, at which time IPTG was added to a final concentration of 1 mM, and incubation continued for 2-3 h. Cells were harvested by centrifugation and SDS-PAGE was performed to confirm expression of the perhydrolase at 20-40% of total soluble protein.

EXAMPLE 2

Construction of *Thermotoga maritima* Acetyl Xylan Esterase Variants at Residue C277

The C277 (Cys277) position of *T. maritima* acetyl xylan esterase was changed to each of Val, Ala, Ser and Thr using oligonucleotide primer pairs (Table 2) that were designed based on the codon optimized sequence of *T. maritima* acetyl xylan esterase (SEQ ID NO: 7) in the plasmid pSW228. The mutations were made using QUIKCHANGE® (Stratagene) according to the manufacturer's instructions. Amplified plasmids were treated with 1 U of DpnI at 37° C. for 1 hour. Treated plasmids were used to transform chemically competent *E. coli* XL1-Blue (Stratagene). Transformants were plated on LB-agar supplemented with 0.1 mg ampicillin/mL and grown overnight at 37° C. Up to five individual colonies were picked and the plasmid DNA sequenced to confirm the expected mutations.

TABLE 2

Oligonucleotides used to change residue 277 in T. maritima.

| | forward 5' to 3' | | reverse 5' to 3' |
|---|---|---|---|
| Tma_C277Vf (SEQ ID NO: 53) | ggacaacatcGTG cctccttcta | Tma_C277Vr (SEQ ID NO: 54) | TAGAAGGAGGCACGA TGTTGTCC |
| Tma_C277Af (SEQ ID NO: 55) | ggacaacatcGC Gcctccttcta | Tma_C277Ar (SEQ ID NO: 56) | TAGAAGGAGGCGCGA TGTTGTCC |
| Tma_C277Sf (SEQ ID NO: 57) | ggacaacatcTCA cctccttcta | Tma_C277Sr (SEQ ID NO: 58) | TAGAAGGAGGTGAGA TGTTGTCC |
| Tma_C277Tf (SEQ ID NO: 59) | ggacaacatcACC cctccttcta | Tma_C277Tr (SEQ ID NO: 60) | TAGAAGGAGGGGTGA TGTTGTCC |

EXAMPLE 3

Expression of *Thermotoga maritime* Acetyl Xylan Esterase Variants in *E. coli* KLP18

Plasmids with confirmed acetyl xylan esterase mutations were used to transform *E. coli* KLP18 (Example 1). Transformants were grown in LB media at 37° C. with shaking up to $OD_{600nm}$=0.4-0.5, at which time IPTG was added to a final concentration of 1 mM, and incubation continued for 2-3 h. Cells were harvested by centrifugation and SDS-PAGE was performed to confirm expression of the acetyl xylan esterase at 20-40% of total soluble protein.

EXAMPLE 4

Expression of *Thermotoga* Acetyl Xylan Esterase Variants in *E. coli* KLP18 Using 1-Liter Bioreactor Plasmids with confirmed acetyl xylan esterase mutations were used to transform *E. coli* KLP18 (Example 1). Transformants were plated onto LB-ampicillin (100 μg/mL) plates and incubated overnight at 37° C. Cells were harvested from a plate using 2.5 mL LB media supplemented with 20% (v/v) glycerol, and 1.0 mL aliquots of the resulting cell suspension frozen at −80° C. One mL of the thawed cell suspension was transferred to a 1-L APPLIKON® Bioreactor (APPLIKON® Biotechnology, Foster City, Calif.) with 0.7 L medium containing $KH_2PO_4$ (5.0 g/L), $FeSO_4$ heptahydrate (0.05 g/L), $MgSO_4$ heptahydrate (1.0 g/L), sodium citrate dihydrate (1.90 g/L), yeast extract (Amberex 695, 5.0 g/L), Biospumex 153K antifoam (0.25 mL, Cognis Corporation), NaCl (1.0 g/L), $CaCl_2$ dihydrate (0.1 g/L), and NIT trace elements solution (10 mL/L). The trace elements solution contained citric acid monohydrate (10 g/L), $MnSO_4$ hydrate (2 g/L), NaCl (2 g/L), $FeSO_4$ heptahydrate (0.5 g/L), $ZnSO_4$ heptahydrate (0.2 g/L), $CuSO_4$ pentahydrate (0.02 g/L) and $NaMoO_4$ dihydrate (0.02 g/L). Post sterilization additions included glucose solution (50% w/w, 6.5 g) and ampicillin (25 mg/mL) stock solution (2.8 mL). Glucose solution (50% w/w) was also used for fed batch. Glucose feed was initiated 40 min after glucose concentration decreased below 0.5 g/L, starting at 0.03 g feed/min and increasing progressively each hour to 0.04, 0.04, 0.05, 0.06, 0.07, 0.08, 0.09, 0.12, and 0.14 g/min respectively; the rate remaining constant afterwards. Glucose concentration in the medium was monitored, and if the concentration exceeded 0.1 g/L the feed rate was decreased or stopped temporarily. Induction was initiated at $OD_{550}$=50 with addition of 0.8 mL IPTG (0.05 M). The dissolved oxygen (DO) concentration was controlled at 25% of air saturation, first by agitation (400-1000 rpm), and following by aeration (0.5-2 slpm). The temperature was controlled at 37° C., and the pH was controlled at 6.8; $NH_4OH$ (29% w/w) and $H_2SO_4$ (20% w/v) were used for pH control. The cells were harvested by centrifugation (5,000×g for 15 minutes) at 20 h post IPTG addition.

EXAMPLE 5

Preparation of Cell Lysates Containing Semi-Purified *T. maritima* Acetyl Xylan Esterase Variants Cell cultures were grown using a fermentation protocol similar to that described in Example 4 at a 1-L scale (Applikon). Cells harvested by centrifugation at 5,000×g for 15 minutes were resuspended (20% w/v) in 50 mM phosphate buffer pH 7.0 supplemented with 1.0 mM DTT. Resuspended cells were passed through a French pressure cell twice to ensure >95% cell lysis.

EXAMPLE 6

Incubation of *E. coli* KLP18/psW228 Lysate Containing *T. maritima* Wild-type Perhydrolase for DNA Removal A cell suspension of *E. coli* KLP18/psW228 (Example 1) containing the wild-type *T. maritima* perhydrolase was prepared by suspending 1828 grams of frozen cell paste in 50 mM phosphate buffer (pH 7.2) at a wet cell weight loading of 250 grams per liter. Aliquots of this cell suspension were treated as indicated in Table 3. To each aliquot of cell suspension was added magnesium sulfate (2 mM) prior to incubation at 50° C. for approximately 18 hours. At the conclusion of all process steps for each treatment, two 40-mL samples were centrifuged and the supernatant frozen at −80° C. Size exclusion chromatography was subsequently performed on thawed samples using the following protocol: HILOAD™ 26/60 column (GE Healthcare), SUPERDEX™ 200 prep grade packing (GE Healthcare), isocratic elution with 2.5 mL/min of 50 mM phosphate buffer (pH 7.0) at 20° C. with monitoring of the column eluent at 260, 280 and 400 nm.

TABLE 3

Process steps to produce samples for size exclusion chromatography.

| Sample PAA961- | Step 1 | Step 2 | Step 3 |
|---|---|---|---|
| BHF | Homogenization | — | — |
| BH50F | Homogenization | 50° C. incubation | — |
| B75F | Homogenization | 50° C. incubation | 75° C. heat treatment |
| BHQF | Homogenization | 75° C. heat treatment | — |
| A50HF | 50° C. incubation | Homogenization | — |
| A75F | 50° C. incubation | Homogenization | 75° C. heat treatment |

Incubation was done for a period of approximately 18 hours, and heat treatment was for approximately 2 hours.

The *T. maritima* perhydrolase had a retention time of ca. 95 minutes, and components of the sample that eluted from the column at earlier retention times were largely composed of DNA, where the ratio of the 260 nm/280 nm absorbances was approximately 2, and where these collected fractions were analyzed by gel electrophoresis to confirm the presence of DNA.

FIGS. 1A through 1D present the chromatograms of lysate supernatants treated using four different processing steps: (FIG. 1A) crude lysate (no incubation or heat-treatment), (FIG. 1B) lysate after incubation at 50° C., (FIG. 1C) lysate after incubation at 50° C. followed by heat-treatment at 75° C., and (FIG. 1D) lysate after heat-treatment at 75° C. (no 50° C. incubation). All chromatograms have same vertical scale, from −100 to +4500 mAU. DNA components in crude lysate (FIG. 1A) (components with retention times less than 75-80 min) were removed by incubation at 50° C. (FIG. 1B), resulting in the increase in low-molecular-weight DNA fragments that had a retention time of approximately 130-140 min. There was some additional purification of the lysate by the combination of incubation at 50° C. followed by heat-treatment at 75° C. (FIG. 1C), whereas a significant amount of DNA remained in the lysate that was heat-treated at 75° C. without prior incubation at 50° C.

Figure 2A:
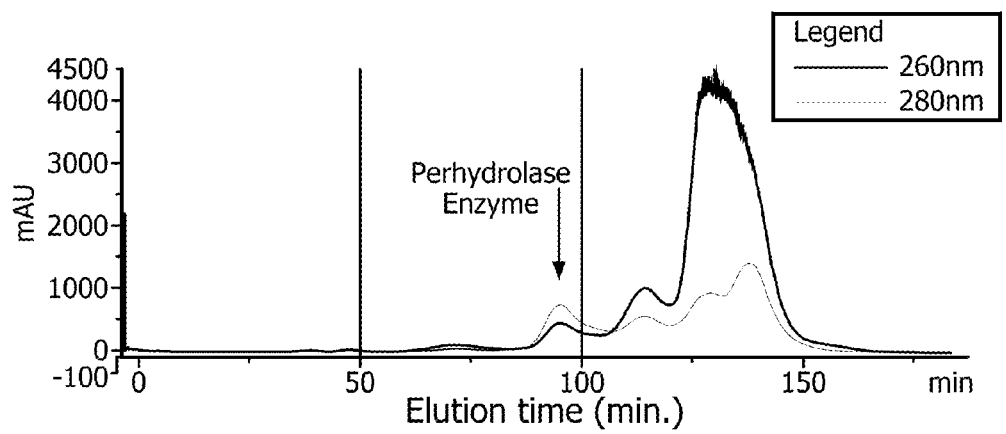
FIGS. 2A through 2C. Chromatograms of lysate supernatants after different processing steps.
Figure 2B:
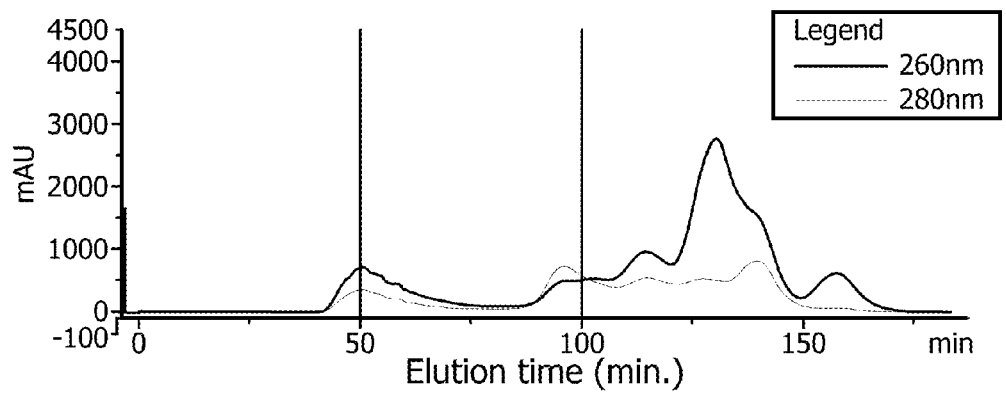
Figure 2C:
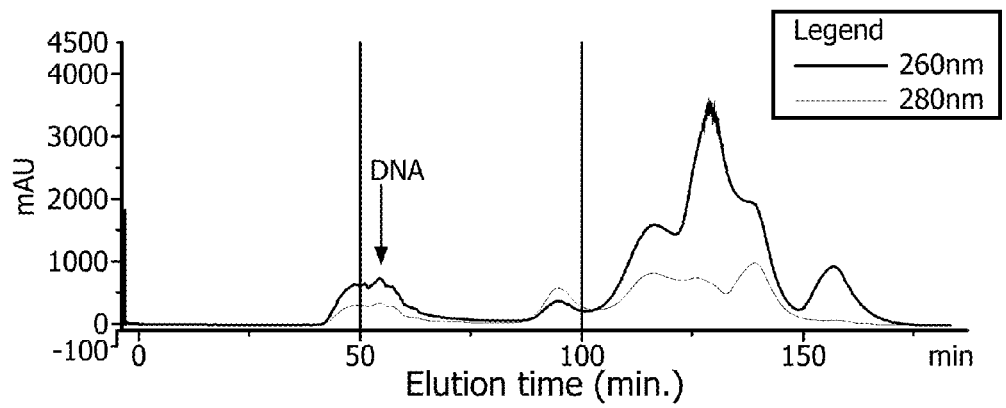

The incubation step was not effective in removing DNA when performed prior to homogenization of the *E. coli* cells containing the perhydrolase. FIGS. 2A through 2C present chromatograms for samples that were prepared according to the following procedures: (FIG. 2A) homogenization followed by incubation at 50° C., (FIG. 2B) incubation of a cell suspension at 50° C. followed by homogenization, and (FIG. 2C) incubation at 50° C. followed by homogenization and subsequent heat treatment at 75° C.; incubation prior to homogenization was not effective for DNA removal (see FIG. 2B and FIG. 2C).

EXAMPLE 6

Incubation of *E. coli* KLP18 lysate containing *T. maritima* C277S perhydrolase variant for DNA removal The procedure described in Example 5 was repeated using an incubation temperature of 45° C. and a lysate of *E. coli* KLP18 containing *T. maritima* C277S perhydrolase (See Examples 2 and 3; SEQ ID NO: 11). Chromatographic analysis of lysate supernatants after (1) no incubation, (2) incubation at 45° C. with no added magnesium sulfate, and (3) incubation at 45° C. with 2 mM magnesium sulfate was performed. DNA components in crude lysate (components with retention times less than 75-80 min) were removed by incubation at 45° C., resulting in the increase in low-molecular-weight DNA fragments that had a retention time of approximately 130-140 min. A sample component at 50 min that adsorbed at 400 nm was a not a DNA component.

EXAMPLE 7

Two-Stage Heat Treatment of Cell Lysates Containing *T. maritima* Acetyl Xylan Esterase Variants The effect of incubation time and temperature, as well as heat-treatment temperature on reduction of DNA concentration in *E. coli* cell homogenates containing perhydrolase was examined by performing the two-stage heat treatment study outlined in Table 4, below. A 50-mL aliquot of homogenate was placed in a 125-mL sterile disposable shake flask and placed in a shaking incubator for the Stage 1 heat treatment (incubation) for either 8 h or 16 h. At the conclusion of the first stage, the flask was transferred to a shaking water bath at the elevated Stage 2 temperature for 2 h. The resulting perhydrolase-containing mixtures were clarified by centrifugation prior to analysis.

TABLE 4

| Matrix ID | flsk # | Stage 1 Heat Treat. | | Stage 2 Heat Treat. | |
|---|---|---|---|---|---|
| | | Temp, ° C. | Time, hr | Temp, ° C. | Time, hr |
| 8-75 | 1 | 45 | 8 | 75 | 2 |
| | 2 | 50 | 8 | 75 | 2 |
| | 3 | 55 | 8 | 75 | 2 |
| 8-80 | 4 | 45 | 8 | 80 | 2 |
| | 5 | 50 | 8 | 80 | 2 |
| | 6 | 55 | 8 | 80 | 2 |
| 8-85 | 7 | 45 | 8 | 85 | 2 |
| | 8 | 50 | 8 | 85 | 2 |
| | 9 | 55 | 8 | 85 | 2 |
| 16-75 | 10 | 45 | 16 | 75 | 2 |
| | 11 | 50 | 16 | 75 | 2 |
| | 12 | 55 | 16 | 75 | 2 |
| 16-80 | 13 | 45 | 16 | 80 | 2 |
| | 14 | 50 | 16 | 80 | 2 |
| | 15 | 55 | 16 | 80 | 2 |
| 16-85 | 16 | 45 | 16 | 85 | 2 |
| | 17 | 50 | 16 | 85 | 2 |
| | 18 | 55 | 16 | 85 | 2 |

Protein concentration of the final heat treated supernatant was primarily a function of the Stage two heat-treatment temperature with more *E. coli* protein precipitated as Stage two temperature increased.

Total activity as pNPA units per g (mL) of clarified supernatant after two-stage heat-treatment is reported in Table 5.

TABLE 5

| Sample # | Temp 1 (° C.) | Time 1 (hr) | Temp 2 (° C.) | Time 2 (hr) | BCA (mg/g) | pNPA, U/mg protein | Calculated pNPA (U/g) |
|---|---|---|---|---|---|---|---|
| 1 | 45 | 8 | 75 | 2 | 8.76 | 121.3 | 1062.5 |
| 4 | 45 | 8 | 80 | 2 | 7.31 | 124.2 | 907.6 |
| 7 | 45 | 8 | 85 | 2 | 6.97 | 129.7 | 903.8 |
| 10 | 45 | 16 | 75 | 2 | 8.08 | 127.7 | 1032.2 |
| 13 | 45 | 16 | 80 | 2 | 7.34 | 136.2 | 999.7 |
| 16 | 45 | 16 | 85 | 2 | 6.94 | 137.0 | 951.0 |
| 2 | 50 | 8 | 75 | 2 | 9.16 | 104.6 | 958.2 |
| 5 | 50 | 8 | 80 | 2 | 7.65 | 122.3 | 935.3 |
| 8 | 50 | 8 | 85 | 2 | 6.95 | 137.9 | 958.6 |
| 11 | 50 | 16 | 75 | 2 | 8.88 | 122.7 | 1089.6 |

TABLE 5-continued

| Sample # | Temp 1 (° C.) | Time 1 (hr) | Temp 2 (° C.) | Time 2 (hr) | BCA (mg/g) | pNPA, U/mg protein | Calculated pNPA (U/g) |
|---|---|---|---|---|---|---|---|
| 14 | 50 | 16 | 80 | 2 | 8.48 | 111.9 | 948.9 |
| 17 | 50 | 16 | 85 | 2 | 7.15 | 129.8 | 928.3 |
| 3 | 55 | 8 | 75 | 2 | 8.47 | 113.4 | 960.5 |
| 6 | 55 | 8 | 80 | 2 | 7.58 | 124.0 | 939.8 |
| 9 | 55 | 8 | 85 | 2 | 7.09 | 126.7 | 898.1 |
| 12 | 55 | 16 | 75 | 2 | 8.78 | 105.7 | 927.8 |
| 15 | 55 | 16 | 80 | 2 | 8.31 | 109.2 | 907.5 |
| 18 | 55 | 16 | 85 | 2 | 7.17 | 119.5 | 856.5 |

Two-stage heat treatment conditions that resulted in the highest specific activity (U/mg protein) did not also produce the highest total activity per weight (volume) of treated supernatant; Stage 1 at 45° C. or 50° C. for 16 hours with a Stage 2 treatment of 2 hours at 75° C. produced the highest total pNPA activity, as did 45° C. for 8 hours followed by 75° C. for 2 hours.

Figure 3:
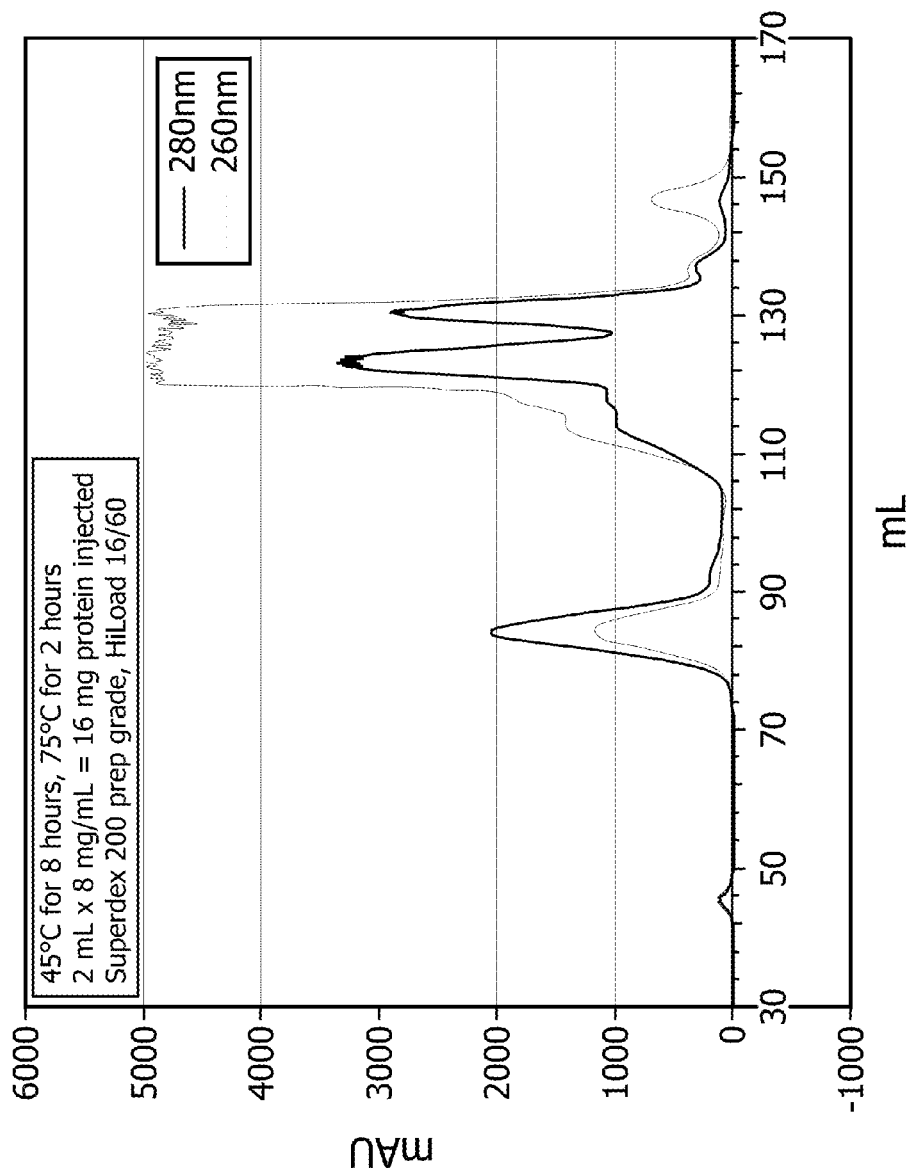
FIG. 3. $1^{st}$ stage temperature 45° C. for 8 h, $2^{nd}$ stage treatment 75° C. for 2 h.
Figure 4:
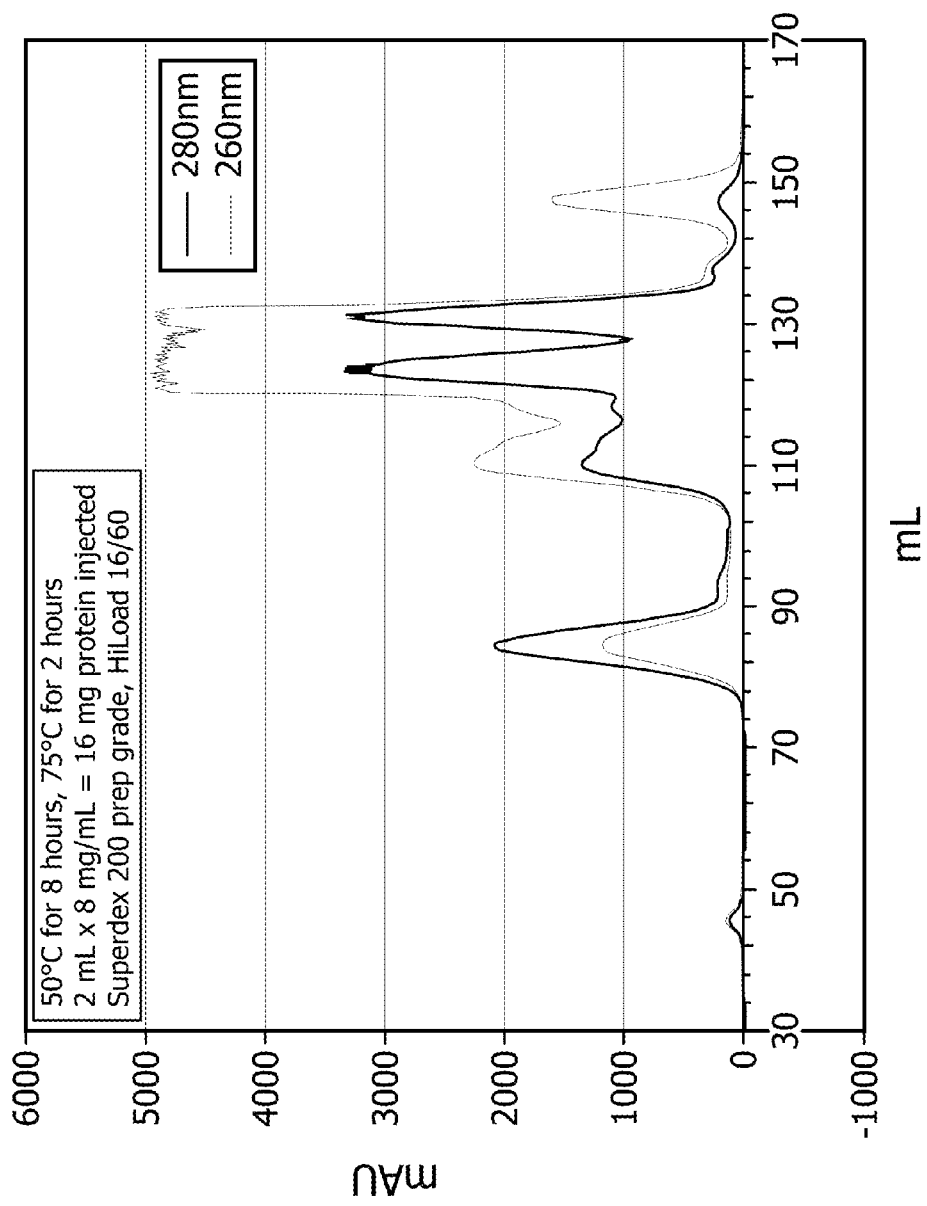
FIG. 4. $1^{st}$ stage temperature 50° C. for 8 h, $2^{nd}$ stage treatment 75° C. for 2 h.
Figure 5:
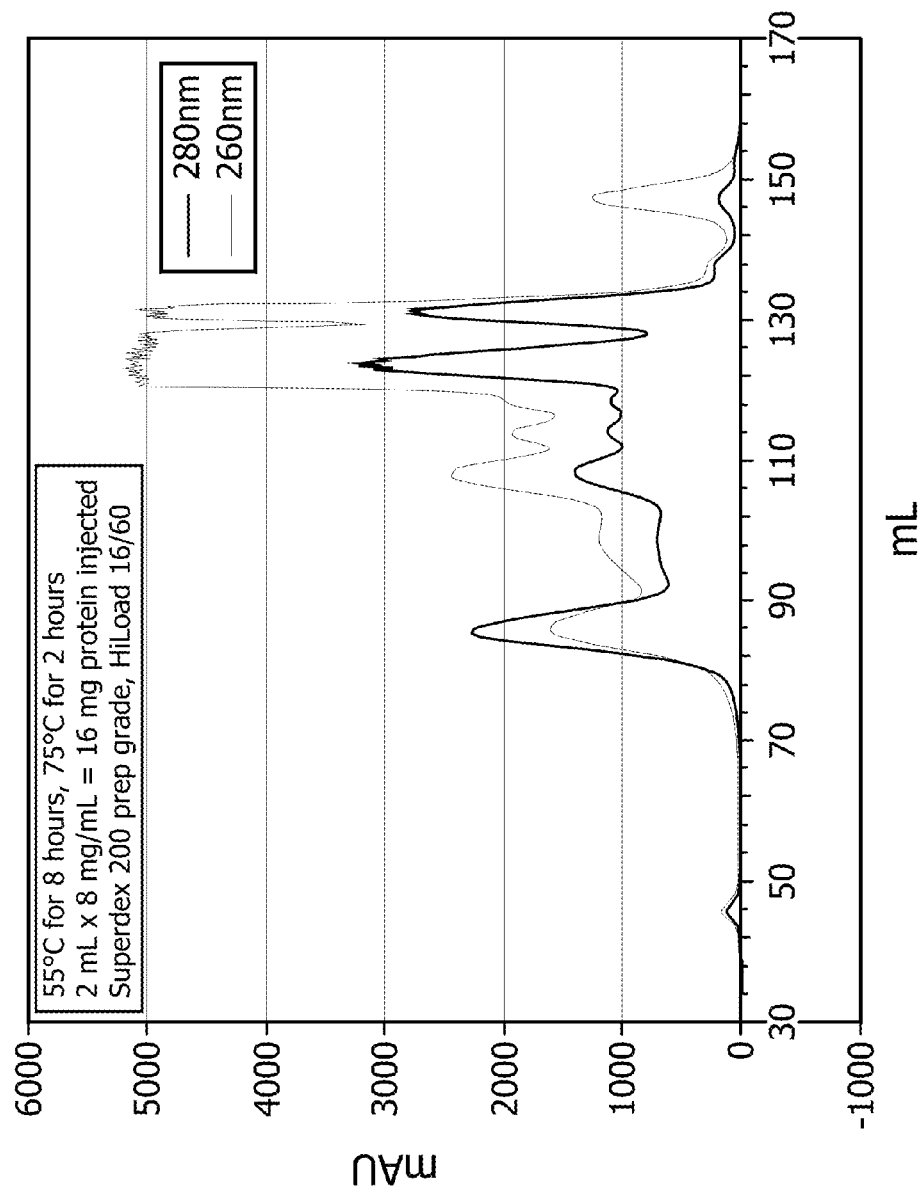
FIG. 5. $1^{st}$ stage temperature 55° C. for 8 h, $2^{nd}$ stage treatment 75° C. for 2 h.
Figure 6:
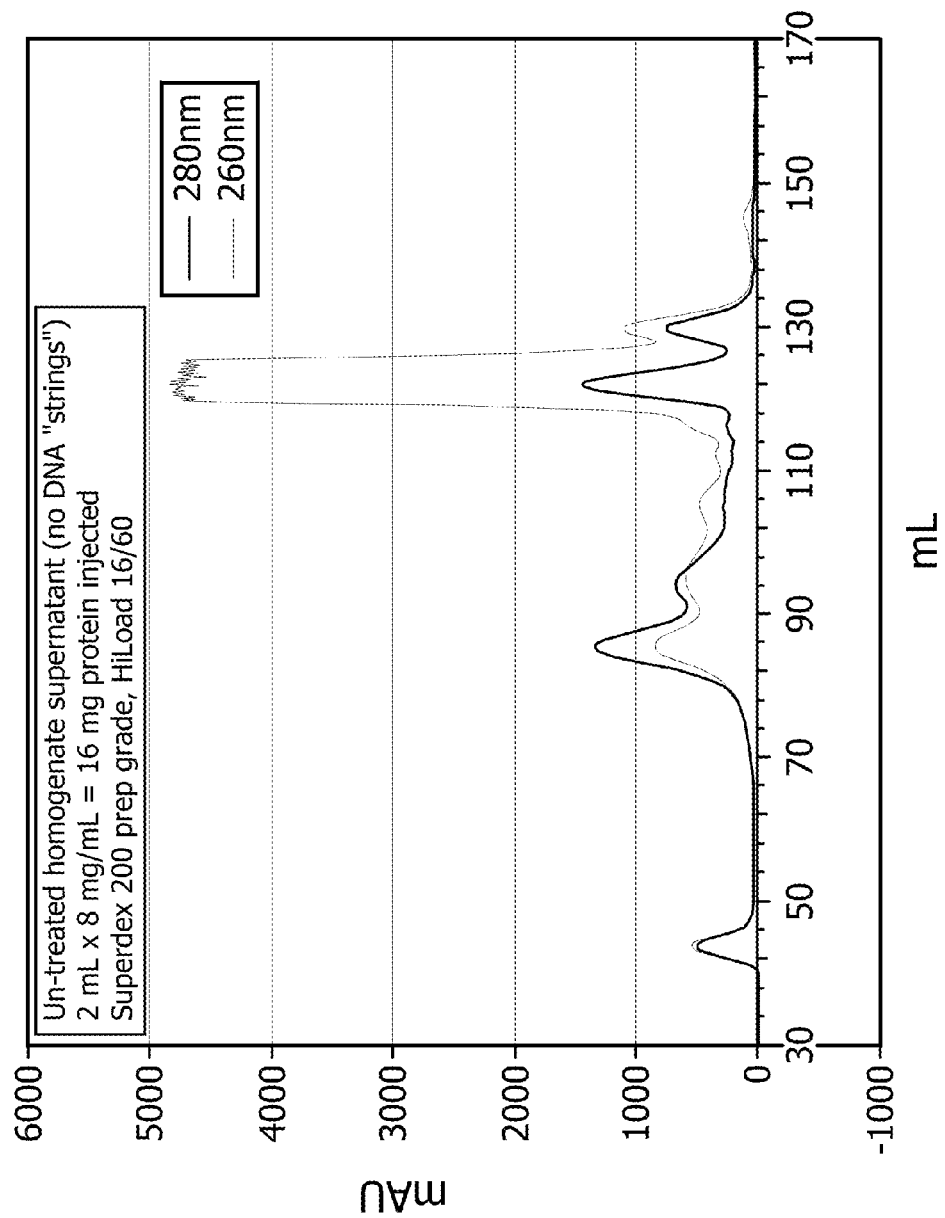
FIG. 6. No heat treatment of cell homogenate.
Figure 7:
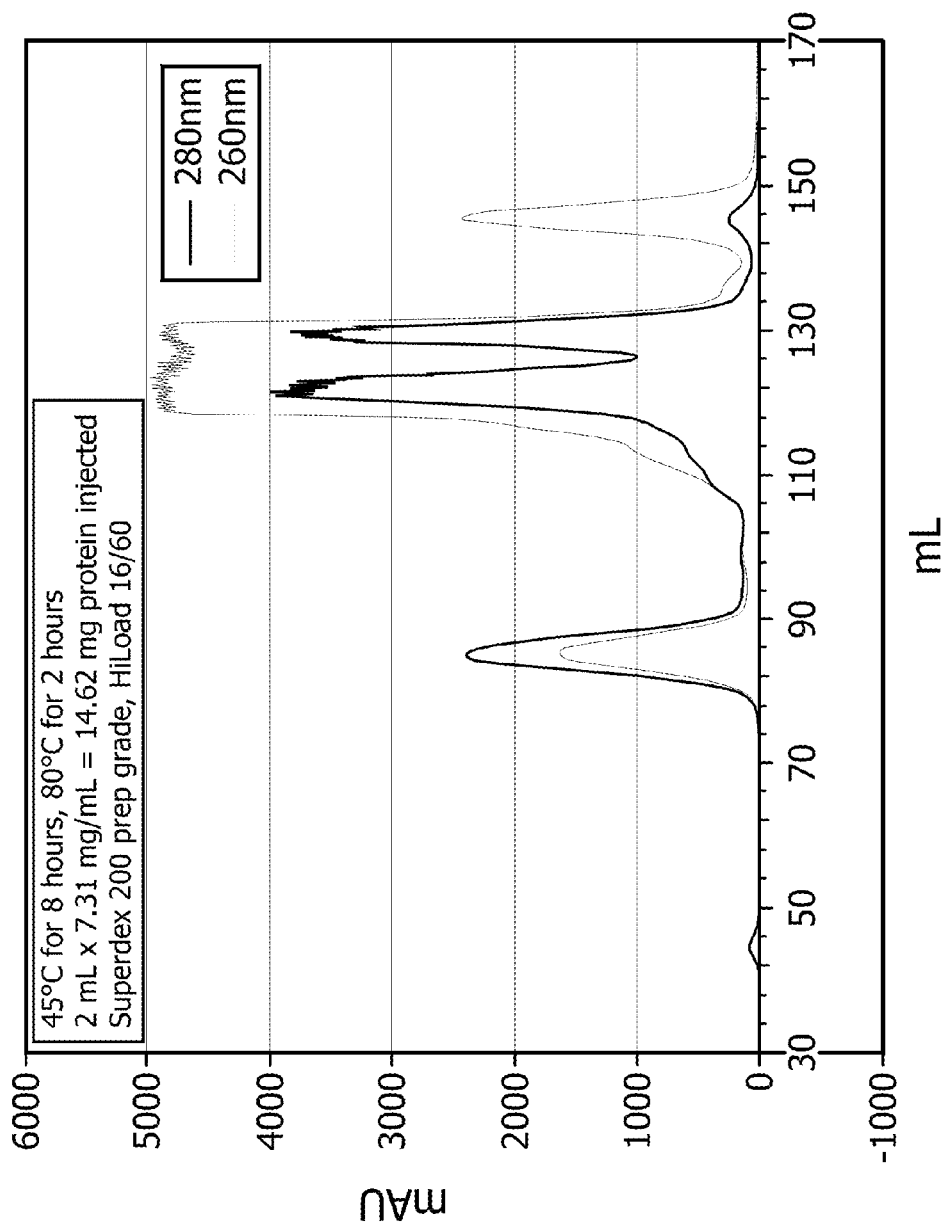
FIGS. 7 through 21. The SEC chromatograms for the remaining conditions for heat treatment outlined in Table 5, all demonstrating reduction in DNA at fractions 42-mL to 46-mL, and resolved perhydrolase at fractions 82-mL to 86-mL.
Figure 8:
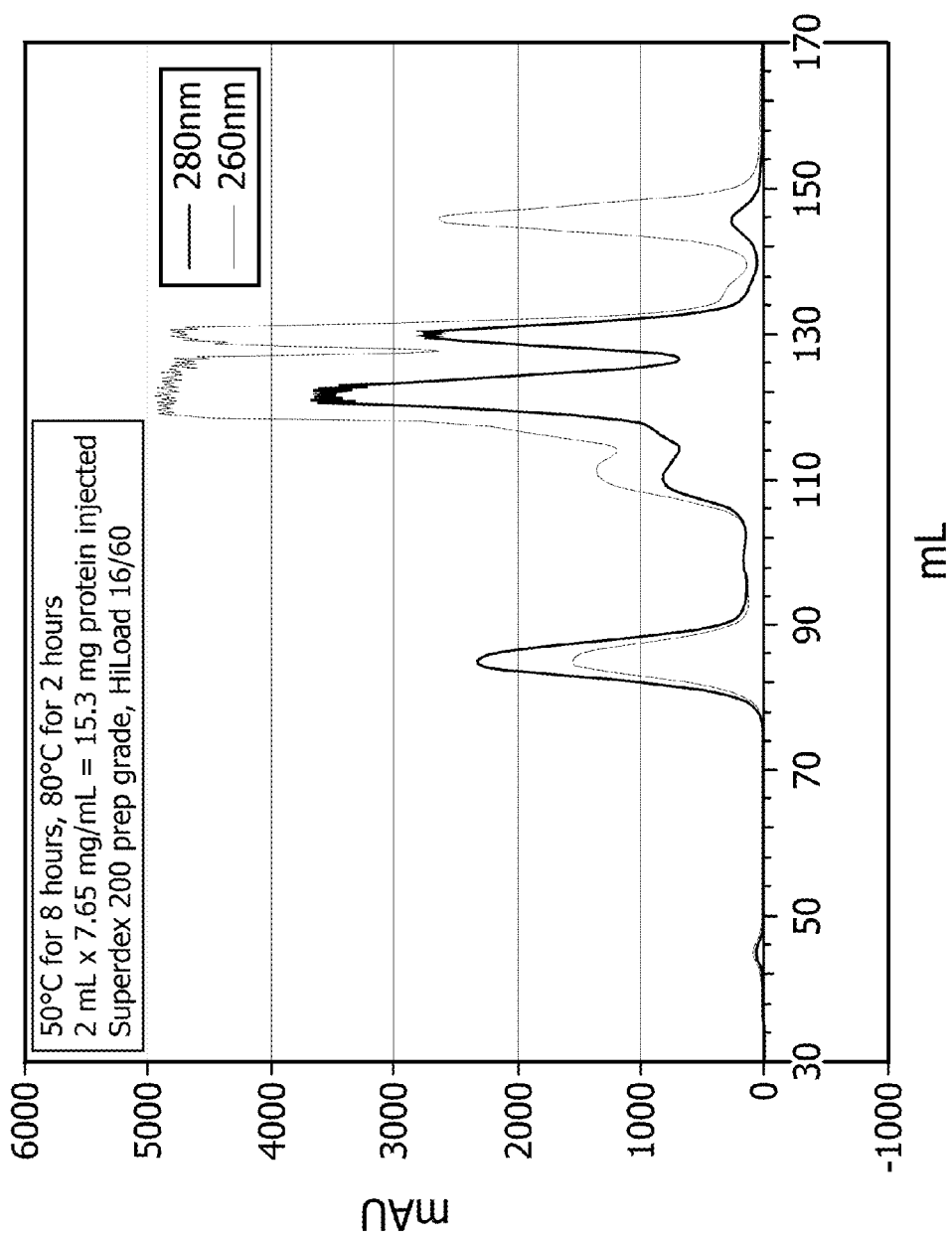
Figure 9:
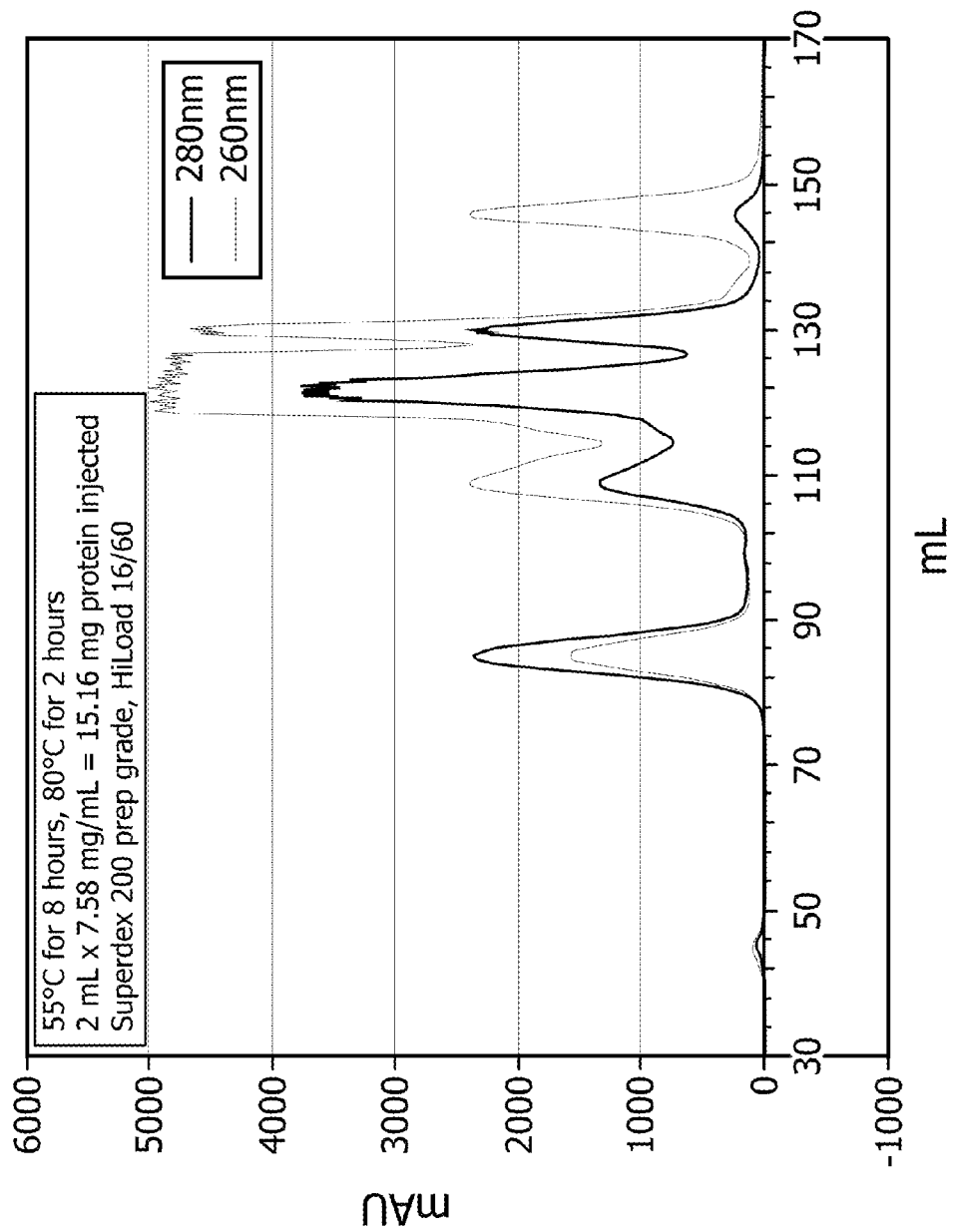
Figure 10:
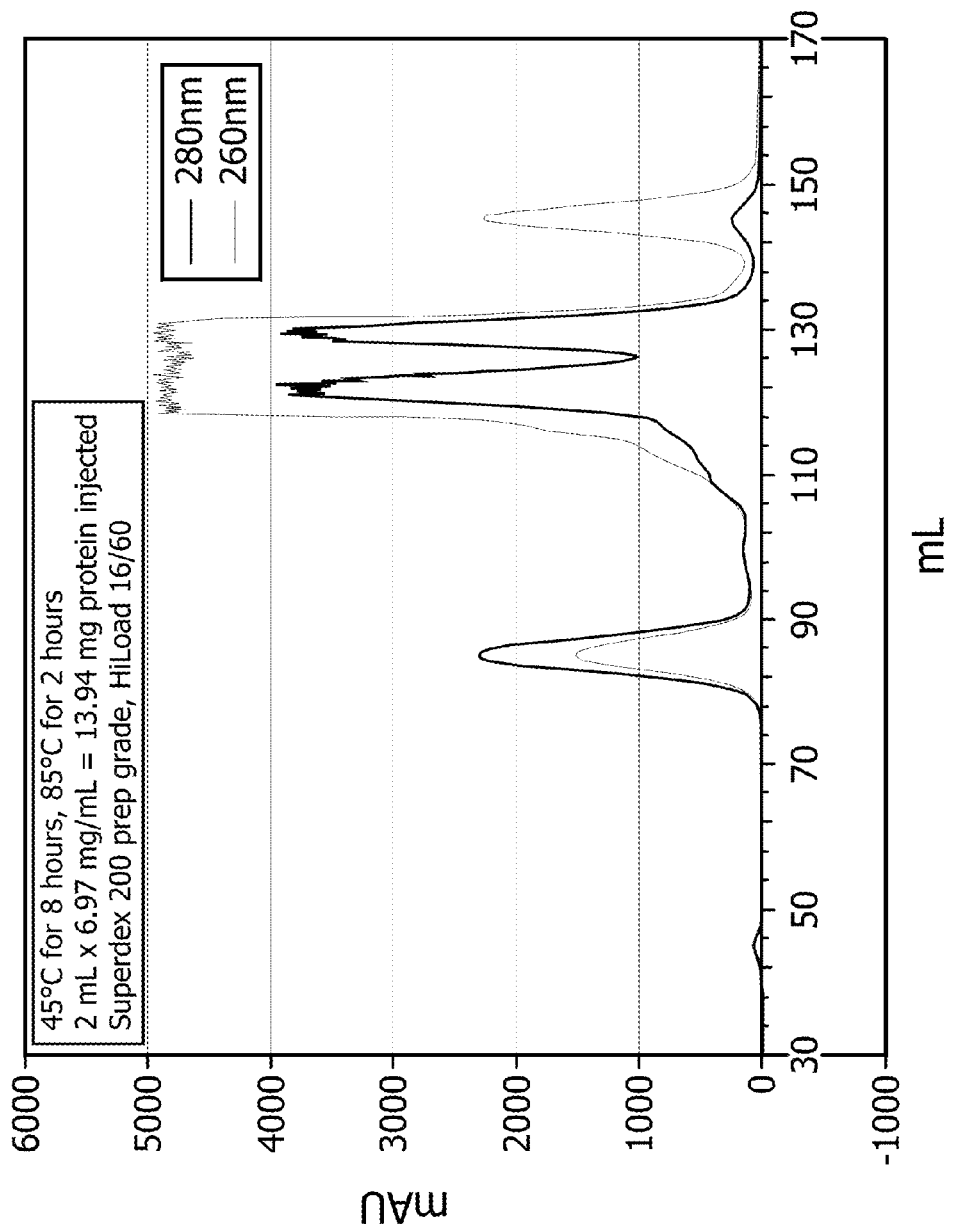
Figure 11:
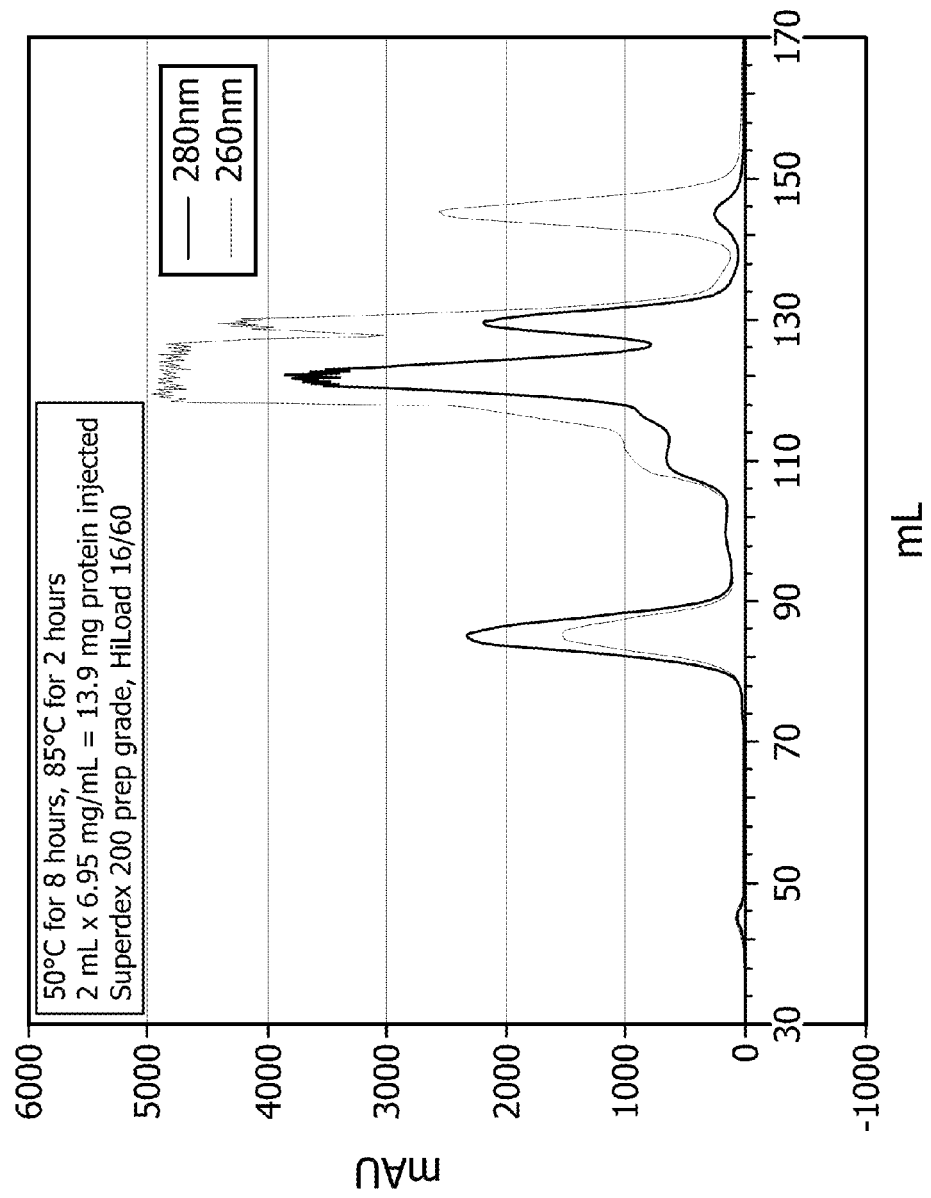
Figure 12:
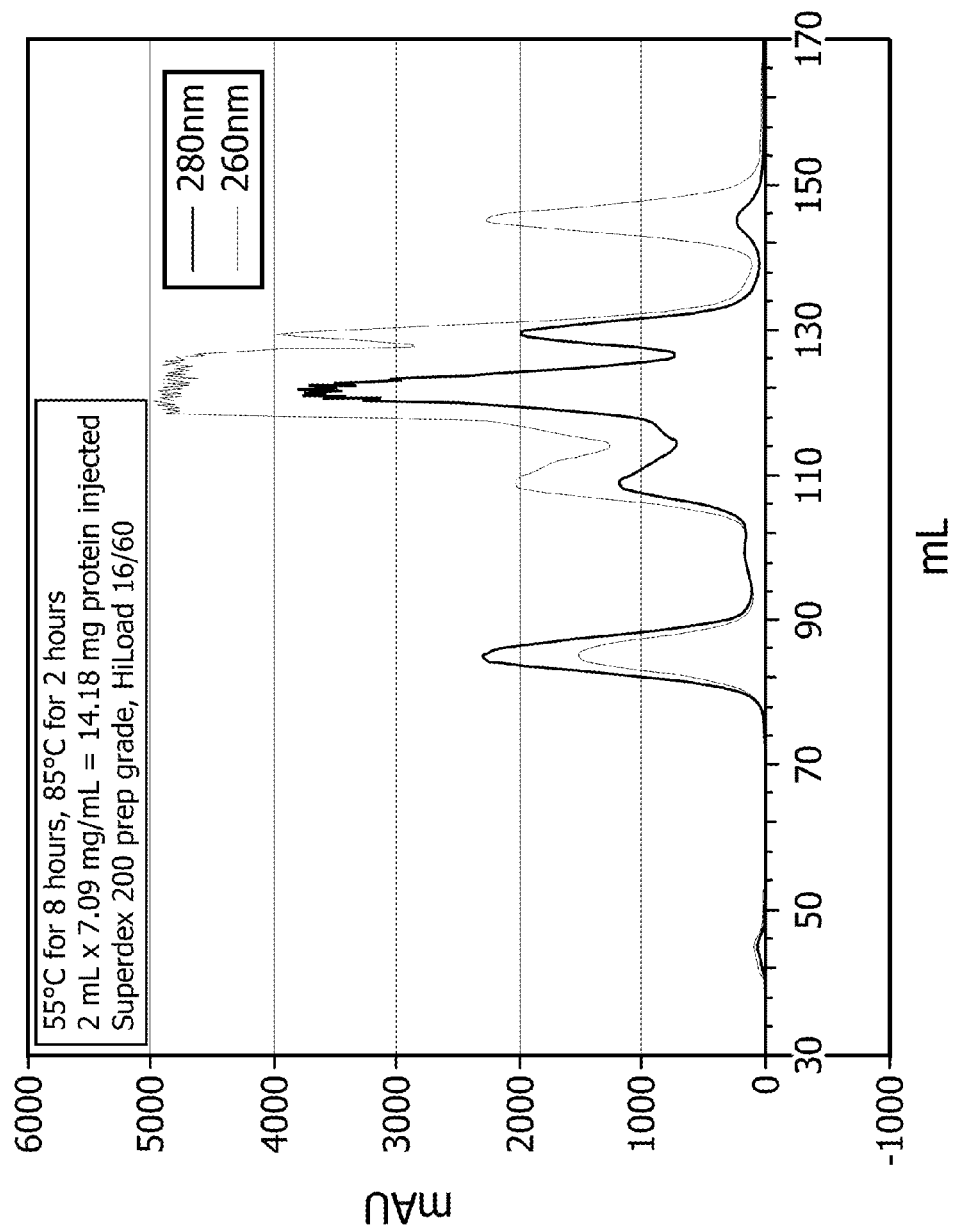
Figure 13:
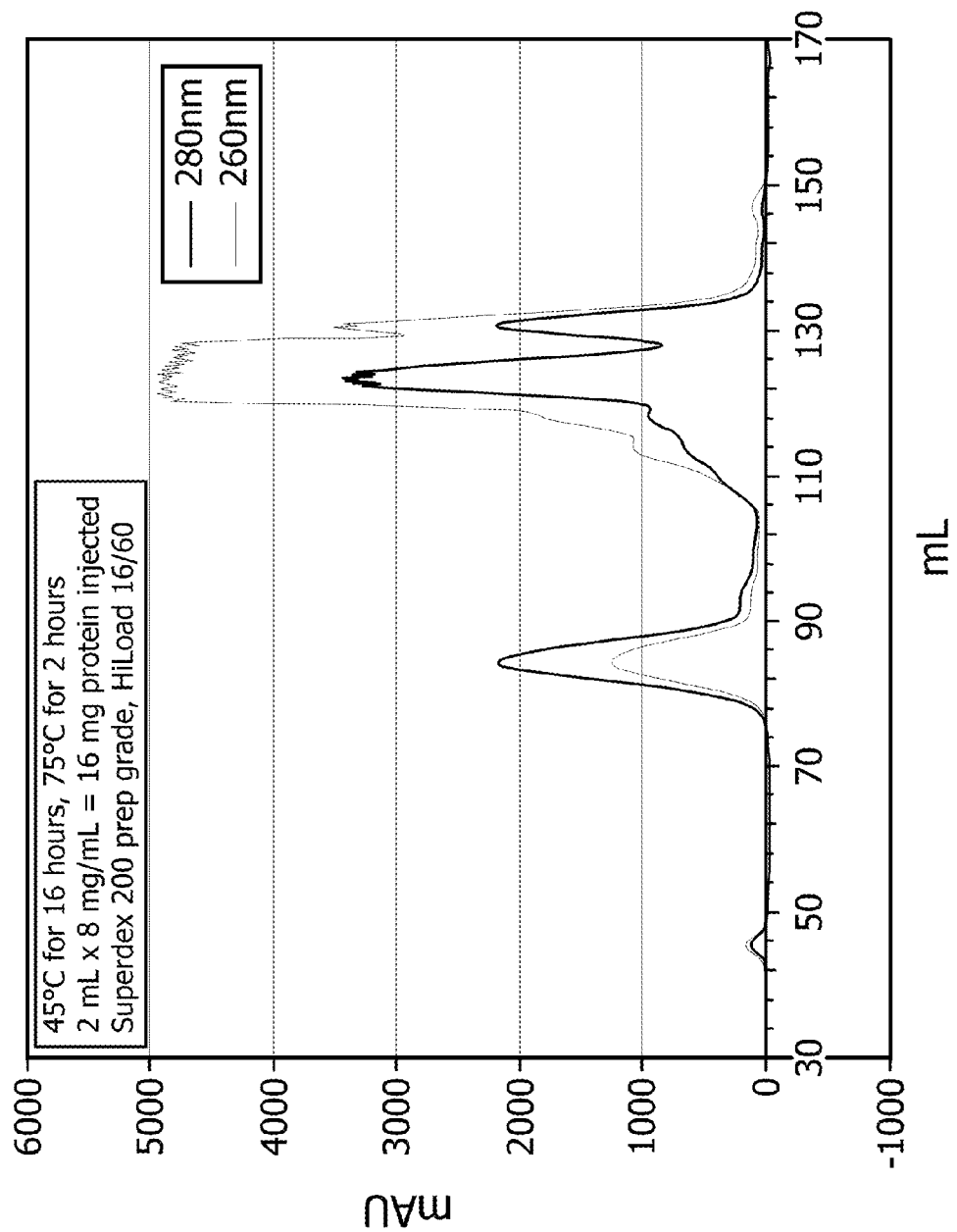
Figure 14:
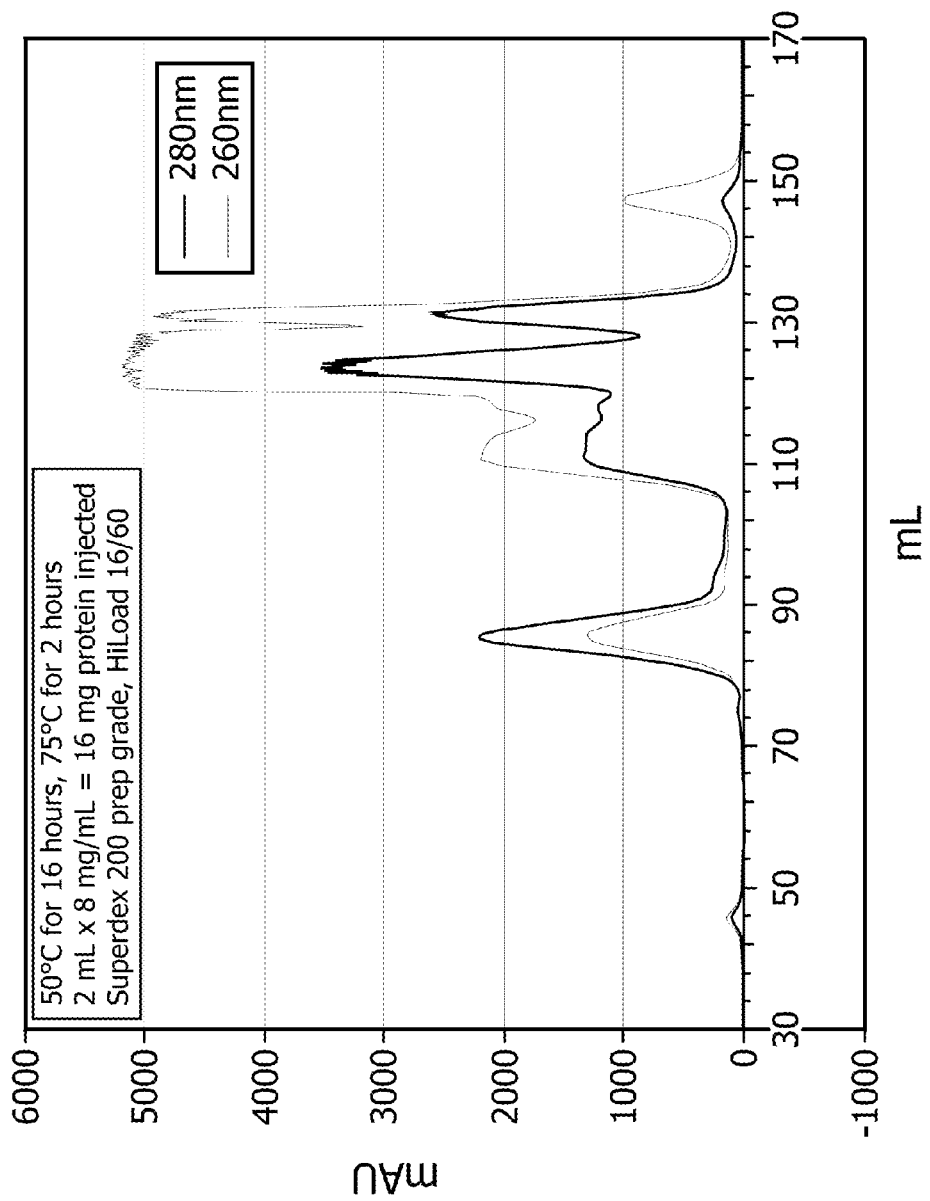
Figure 15:
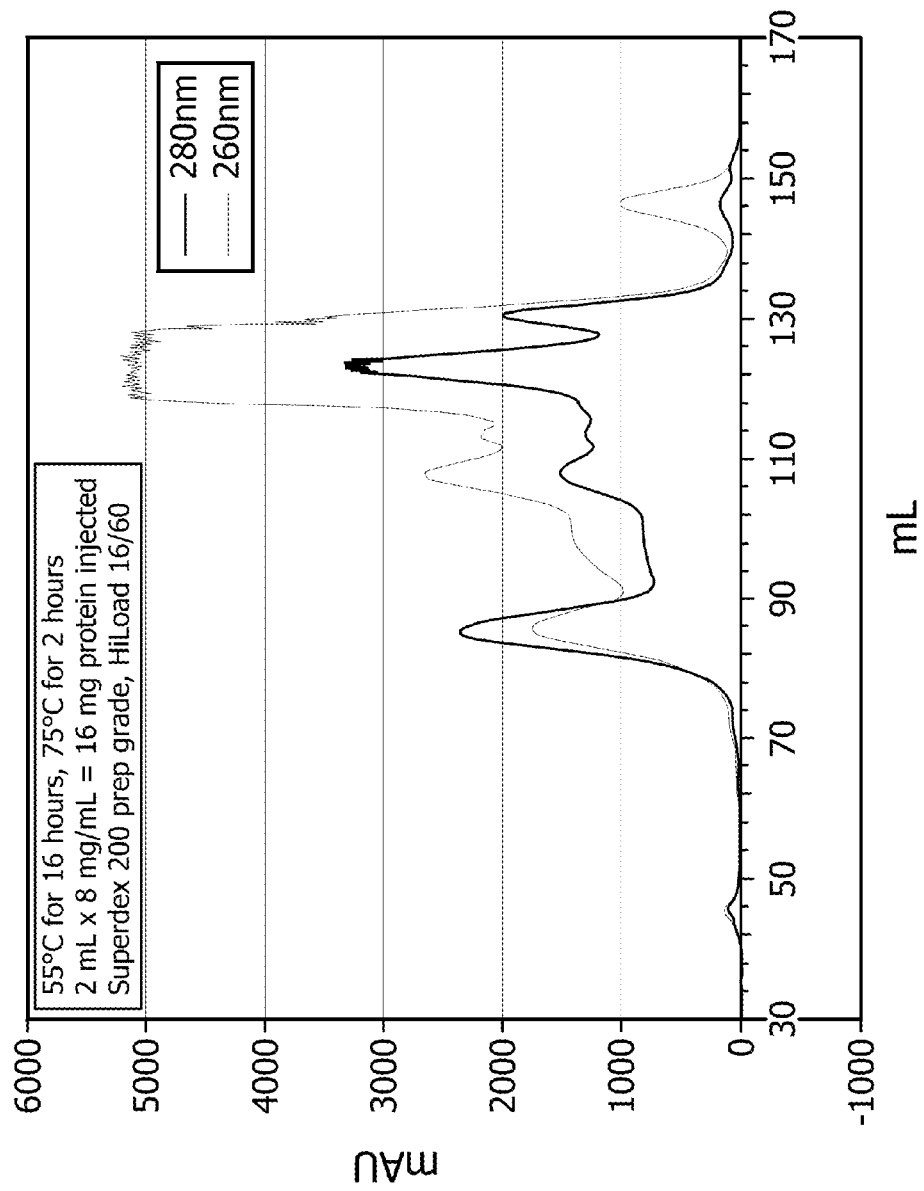
Figure 16:
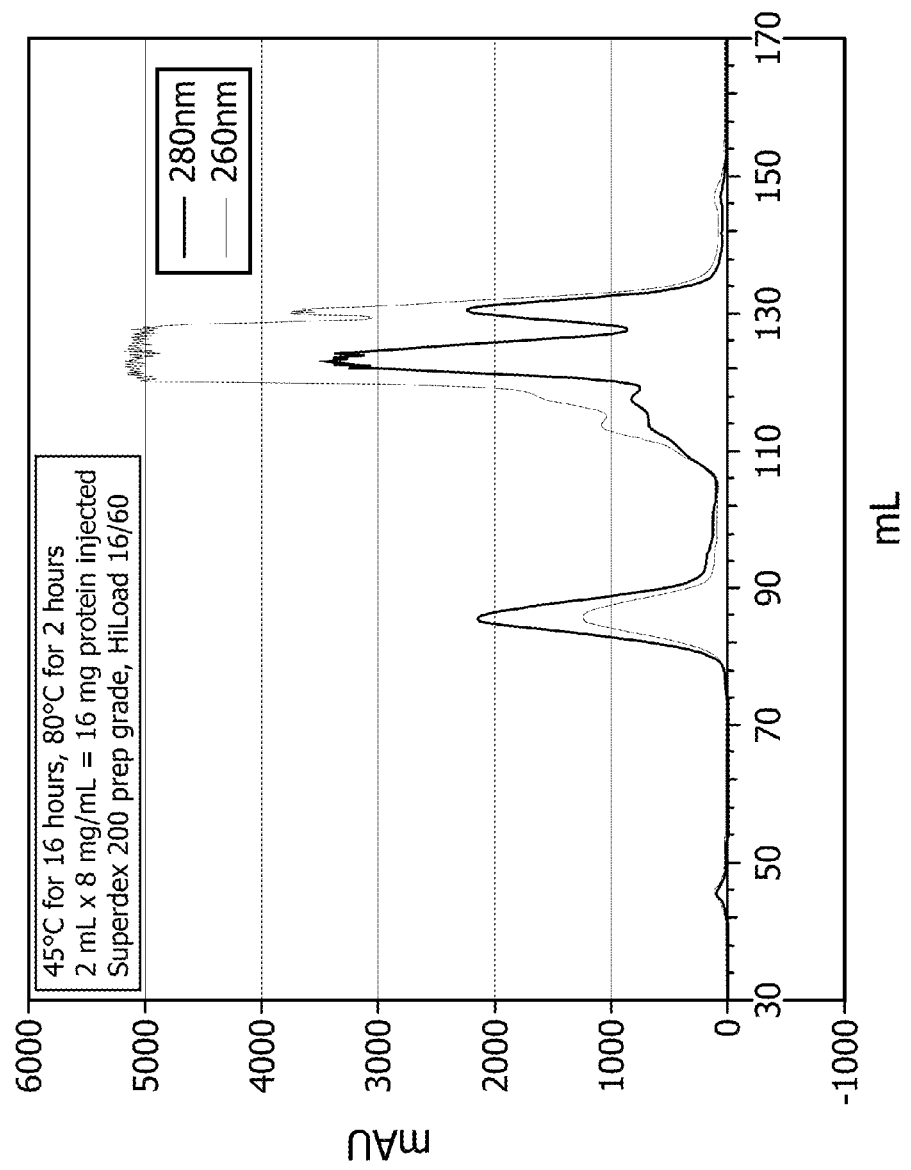
Figure 17:
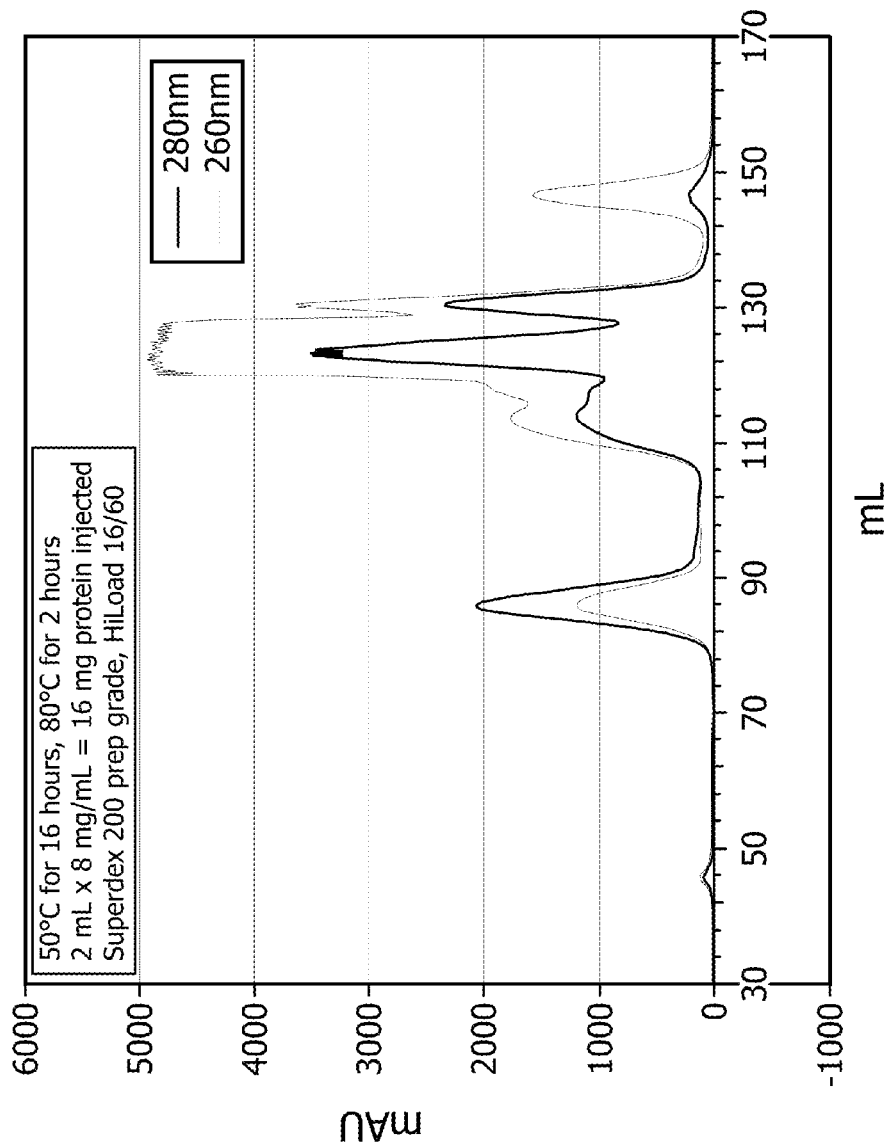
Figure 18:
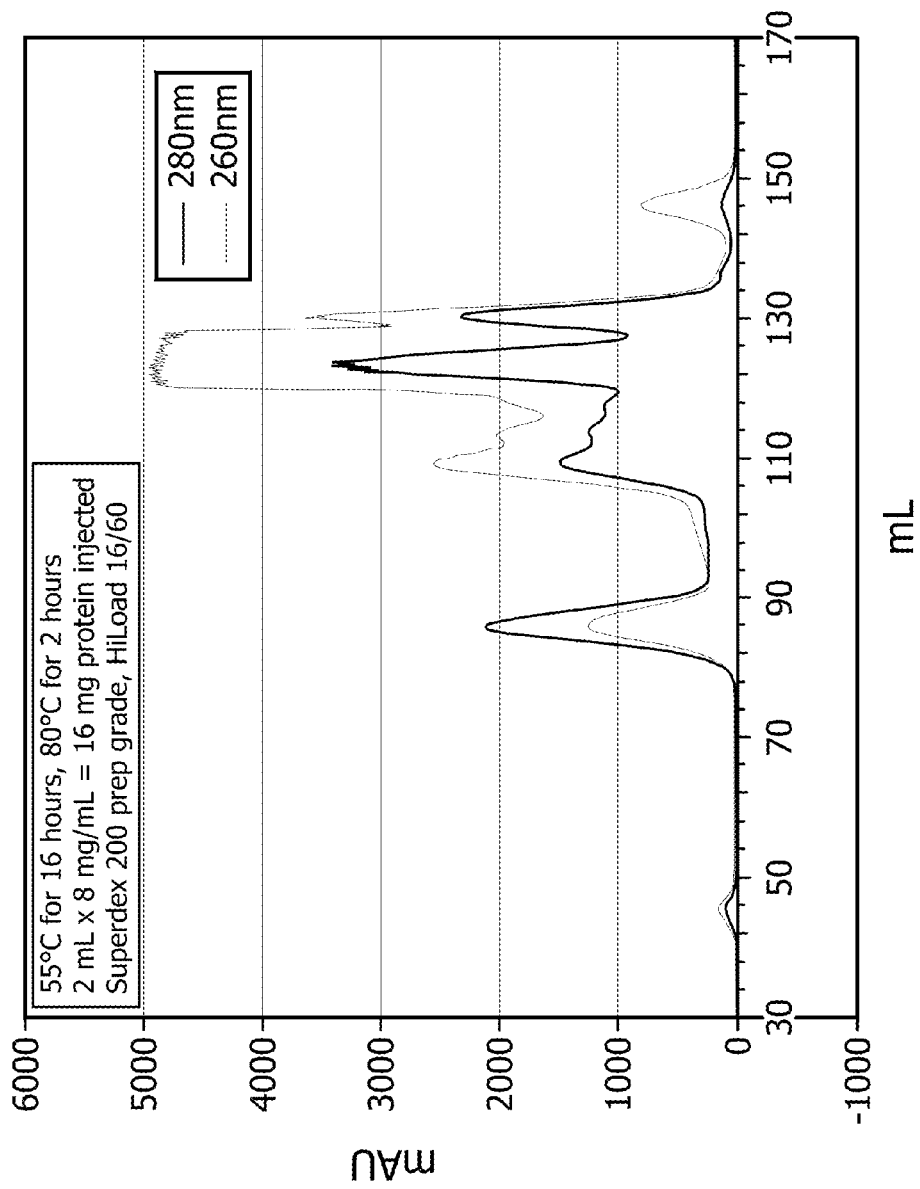
Figure 19:
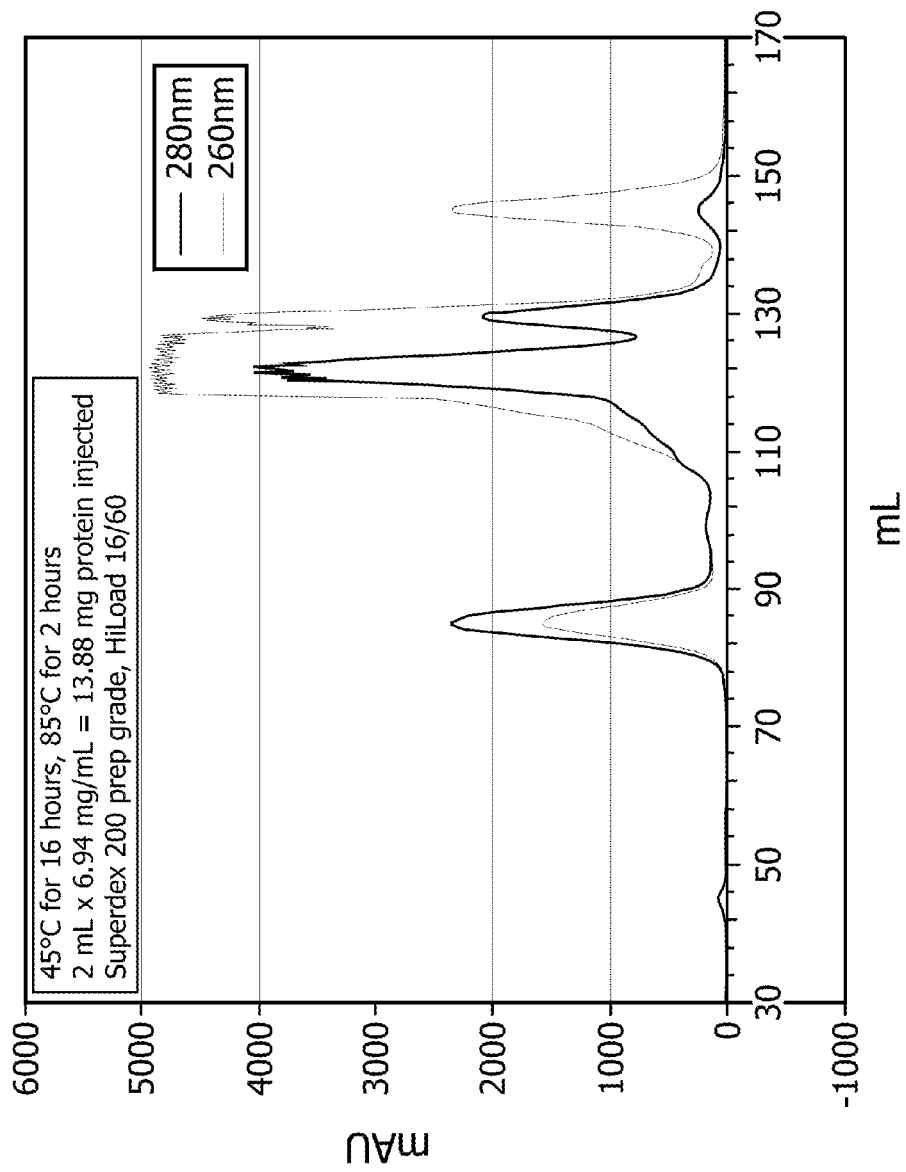
Figure 20:
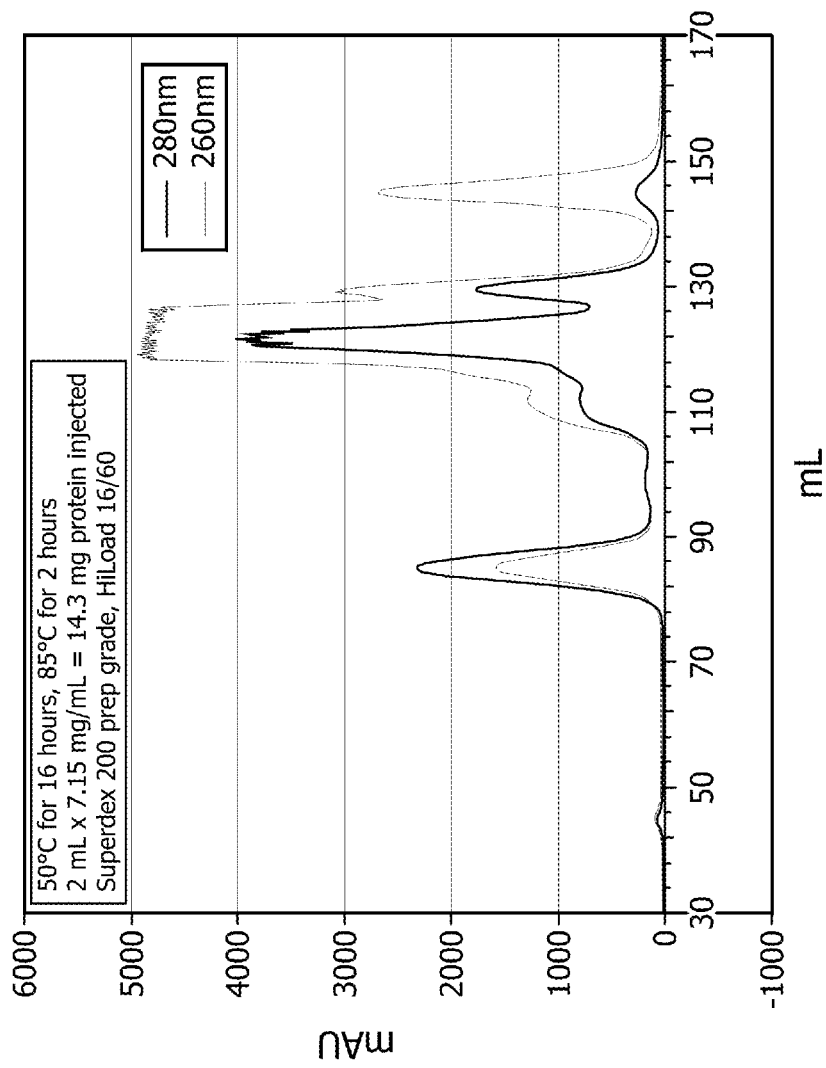
Figure 21:
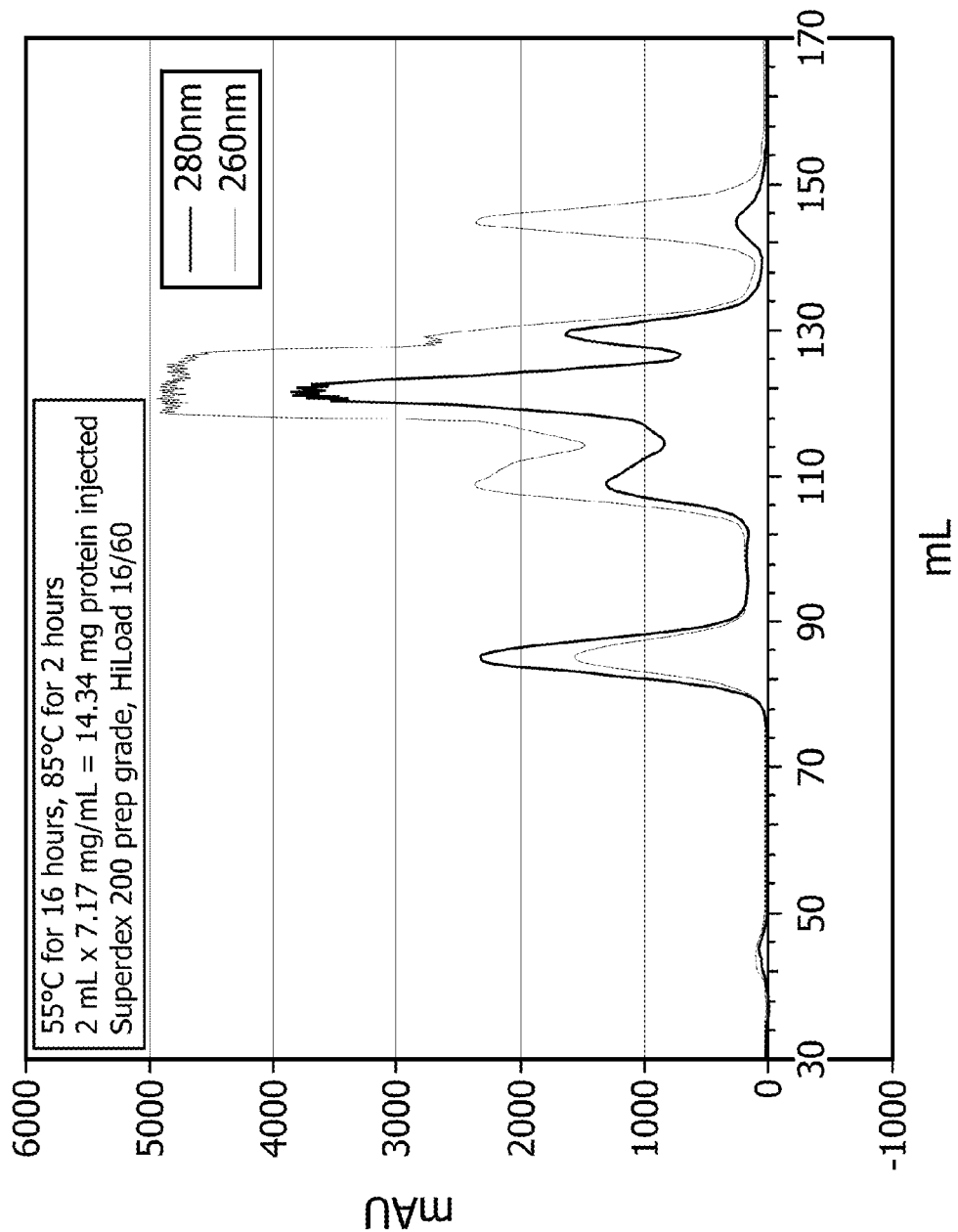

SEC chromatograms demonstrate the production of eluents that partially co-elute with the perhydrolase (the peak in the 82-mL to 86-mL fractions) when the 1$^{st}$ stage temperature was 55° C. and the 2$^{nd}$ stage treatment was 75° C. for 2 h. The best resolution was at a 1$^{st}$ stage temperature of 45° C.; there is still resolution is at 50° C., but the perhydrolase peak is unresolved at 55° C. (FIGS. 3, 4, and 5, respectively). For comparison, the SEC chromatogram of unheated cell homogenate is illustrated in FIG. 6, where DNA elutes in the 42-mL to 46-mL fractions.

The SEC chromatograms for the remaining conditions for heat treatment outlined in Table 5 appear in FIGS. 7 through 21, all demonstrating reduction in DNA at fractions 42-mL to 46-mL, and resolved perhydrolase at fractions 82-mL to 86-mL.

Figure 22:
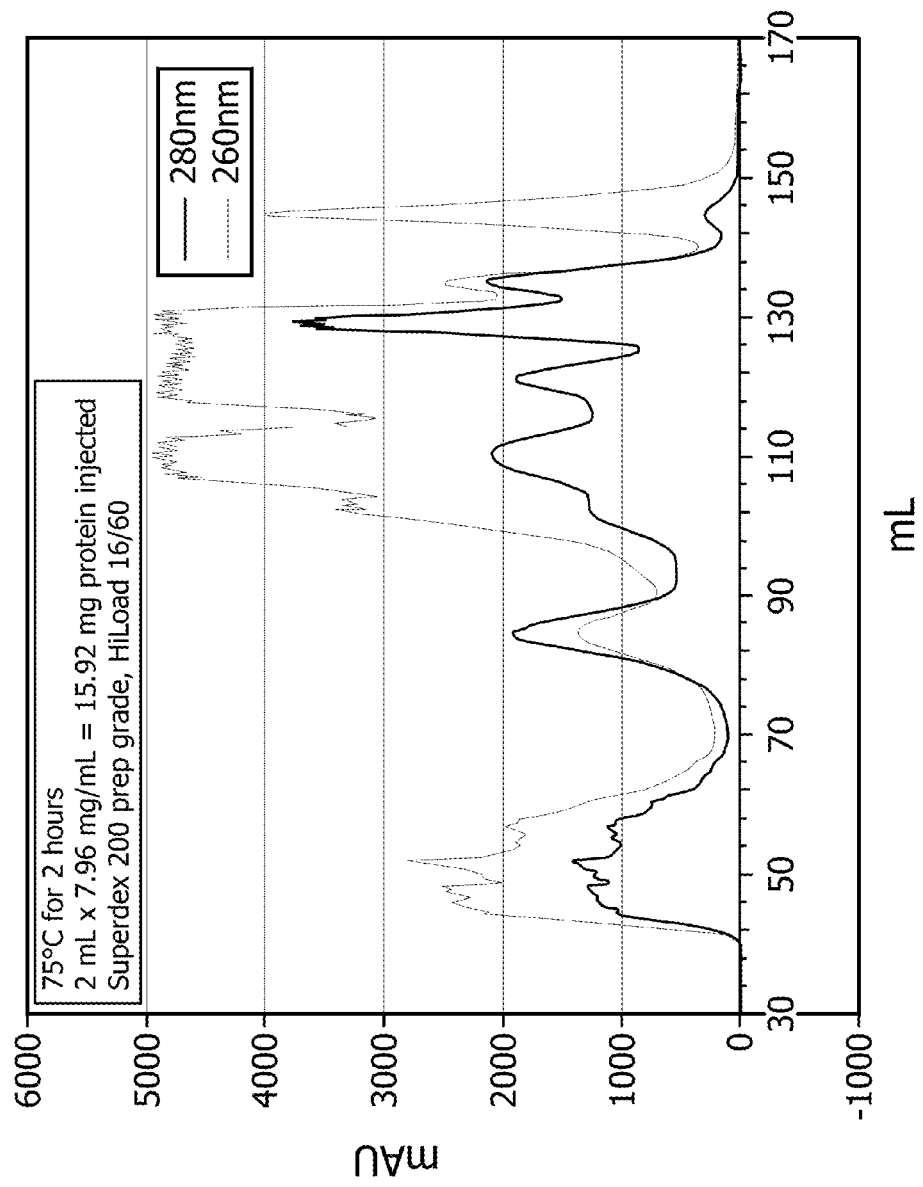
FIG. 22. SEC chromatogram (control) showing the effect of single stage heat treatment (75° C.).
Figure 23:
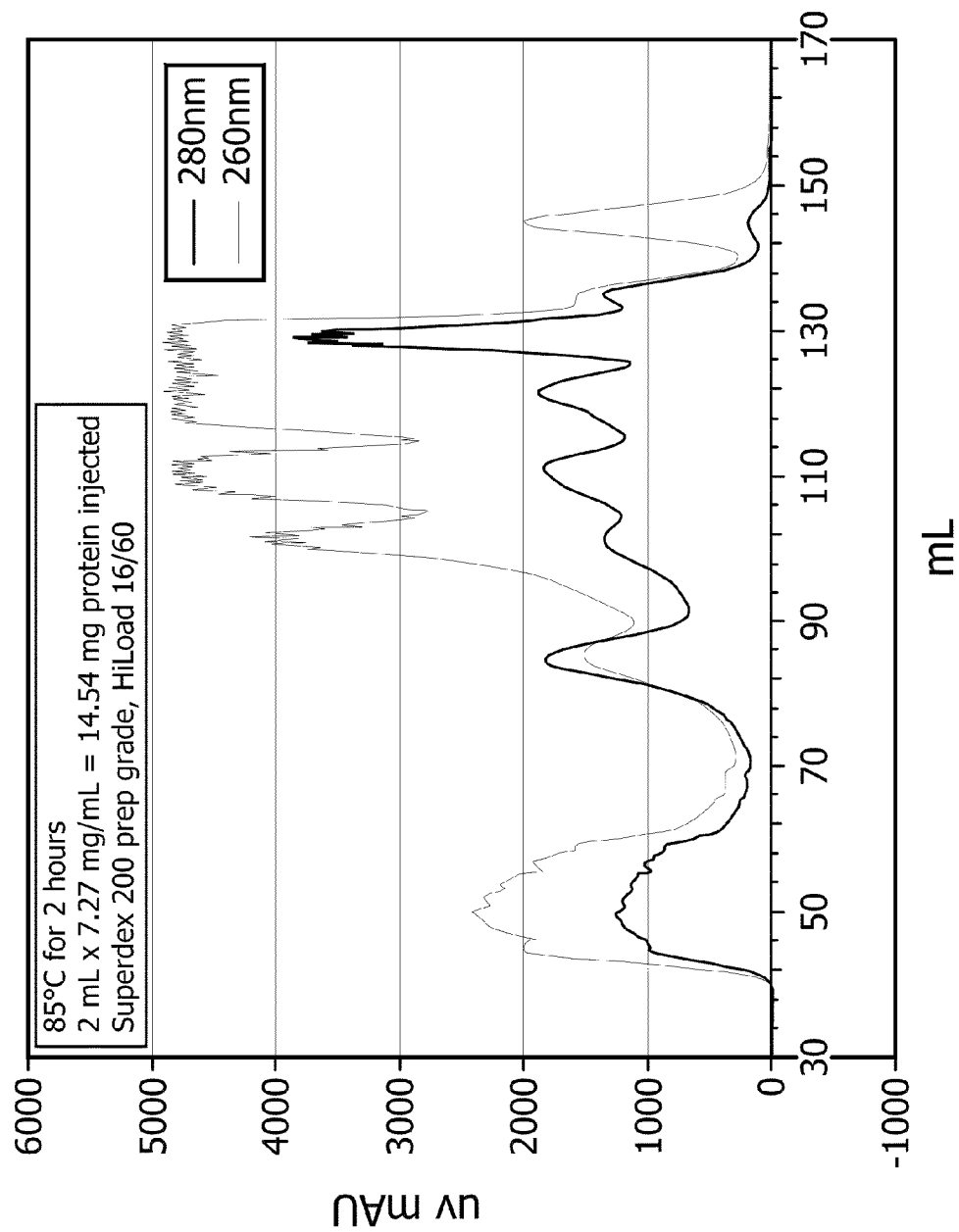
FIG. 23. SEC chromatogram (control) showing the effect of single stage heat treatment (85° C.).

The results of two additional control experiments illustrating the effect of a single-stage heat treatment for 2 hours at 75° C. or 85° C. are provided in the SEC chromatograms of FIGS. 22 and 23, respectively. A significant amount of DNA remained after single-stage heat treatment at 75° C. or 85° C. for 2 hrs.

EXAMPLE 8

Filtration of Heat-treated *E. coli* Cell Homogenates Containing *T. maritima* C277S Perhydrolase Variant A homogenate of *E. coli* KLP18/pSW228/C277S containing *T. maritima* C277S perhydrolase variant (9.9 mg/mL total protein by BCA protein assay) was prepared using a dairy homogenizer operating at 12,000 psig (approximately 82/4 MPa), the pH of the homogenate was adjusted to pH 7.3, and magnesium sulfate (2 mM) was added. The resulting homogenate was divided into to five aliquots (A-E; 250-mL aliquots) and treated as follows: (A) incubated at 50° C. for 16 h with slow mixing, (B) incubated 50° C. for 5 h with slow mixing, (C, control) added DNAse to 0.5 mg per liter and incubated 50° C. for 5 h with slow mixing, (C, control) added DNAse to 0.5 mg per liter and incubated 50° C. for 16 h with slow mixing, (E, control) no heat treatment of homogenate. For control reactions containing DNAse (DN25, Sigma/Aldrich), a DNAse solution was prepared as 1 mg/mL in KPB buffer (25 mM, pH 7.0) containing 5 mM MgSO$_4$: Samples of each homogenate were first clarified by centrifugation then filtered for 2 min using a Nanosep 0.2 micron spin filter (PALL), and the percentage of fitrate recovered compared to starting homogenate was determined. Incubation for 5 h at 50° C. produced a significant improvement in filterability of the homogenate when compared to no heat treatment at 50° C., and no significant improvement in filterability was obtained when 0.5 mg/L DNAse was added to the homogenate prior to heat treatment (Table 6).

TABLE 6

| aliquot | treatment | filtrate (wt %) |
|---|---|---|
| E | none | 33 |
| A | 16 h incubation at 50° C. | 84 |
| B | 5 h incubation at 50° C. | 77 |
| C | 5 h incubation at 50° C. with 0.5 mg/L DNAse | 82 |
| D | 16 h incubation at 50° C. with 0.5 mg/L DNAse | 82 |

EXAMPLE 9

Filtration of Heat-treated *E. coli* Cell Homogenates Containing *T. maritima* C277S Perhydrolase Variant The procedure described in Example 8 was repeated using temperatures and incubation times are described in Table 7; control reactions were run by adding 0.5 mg/L DNAse to the homogenate prior to incubation. Filtration results obtained using the protocols in Table 7 are reported in Tables 8 and 9. A control experiment was performed by first heat-treating an aliquot of the homogenate at 81° C. for 1 h, then cooling to 50° C. and incubating for 5 h or 21 h with or without added DNAse to demonstrate the significantly lower filterability of homogenate that is subjected to a single stage heat treatment at high temperature when compared to incubation at 50° C. (Table 10).

TABLE 7

Heat-treatment protocols.

| aliquot | temp (° C.) | DNAse | Time, hr |
|---|---|---|---|
| A | 30 | − | 5 or 21 |
| B | 30 | + | 5 or 21 |
| C | 40 | − | 5 or 21 |
| D | 40 | + | 5 or 21 |
| E | 50 | − | 5 or 21 |
| F | 50 | + | 5 or 21 |
| G | 60 | − | 5 or 21 |
| H | 60 | + | 5 or 21 |
| I | 70 | − | 5 or 21 |
| J | 70 | + | 5 or 21 |
| K | 50 | − | 5 or 21 |
| L | 50 | + | 5 or 21 |

TABLE 8

Filtration results of homogenate after incubation for 5 hr at various temperatures with and without added DNAse.

| Treatment | % filtrate | std dev |
|---|---|---|
| 0 hr | 4.9 | 1.36 |
| 30° C. | 9.1 | 0.51 |
| 30° C. with DNAse | 68.3 | 1.37 |
| 40° C. | 44.3 | 6.17 |
| 40° C. with DNAse | 32.9 | 6.76 |
| 50° C. | 80.6 | 13.66 |
| 50° C. with DNAse | 89.8 | 0.96 |

TABLE 8-continued

Filtration results of homogenate after incubation for 5
hr at various temperatures with and without added DNAse.

| Treatment | % filtrate | std dev |
|---|---|---|
| 60° C. | 18.7 | 0.57 |
| 60° C. with DNAse | 48.4 | 0.96 |
| 70° C. | 23.1 | 2.59 |
| 70° C. with DNAse | 61.2 | 17.54 |

TABLE 9

Filtration results of homogenate after incubation for 21
hr at various temperatures with and without added DNAse.

| aliquot | % filtrate | std dev |
|---|---|---|
| 0 hr | 4.9 | 1.36 |
| 30° C. | 34.5 | 5.56 |
| 30° C. with DNAse | 20.5 | 13.58 |
| 40° C. | 74.1 | 2.15 |
| 40° C. with DNAse | 83.8 | 0.78 |
| 50° C. | 73.3 | 1.23 |
| 50° C. with DNAse | 69.3 | 6.55 |

TABLE 9-continued

Filtration results of homogenate after incubation for 21
hr at various temperatures with and without added DNAse.

| aliquot | % filtrate | std dev |
|---|---|---|
| 60° C. | 58.4 | 48.62 |
| 60° C. with DNAse | 48.8 | 1.60 |
| 70° C. | 27.5 | 0.55 |
| 70° C. with DNAse | 53.1 | 0.48 |

TABLE 10

Filtration results of heat-treated homogenate (81°
C., 1 hr) with subsequent incubation for 5 hr or
21 hr at 50° C. with and without added DNAse.

| Treatment | % filtrate | std dev |
|---|---|---|
| 0 hr | 1.4 | 1.4 |
| 50° C., 5 hr | 13.7 | 13.7 |
| 50° C., 5 h with DNAse | 1.0 | 1.0 |
| 50° C., 21 hr | 1.5 | 1.5 |
| 50° C., 21 hr with DNAse | 0.7 | 0.7 |

What is claimed is:

1. A process comprising:
   (a) providing a microbial cell homogenate comprising soluble and insoluble components, wherein said microbial cell homogenate comprises a recombinantly-produced thermophilic enzyme having perhydrolytic activity;
   (b) subjecting the microbial cell homogenate to a first heat treatment period ranging from at least 4 hours but no more than 24 hours at a temperature ranging from 40° C. to 65° C.;
   (c) subjecting the heat-treated microbial cell homogenate from step (b) to a second heat treatment period ranging from 5 minutes to 4 hours at a temperature ranging from 75° C. to 85° C.;
   (d) removing the insoluble components from the microbial cell homogenate obtained after performing step (b) and step (c) by centrifugation or filtration to obtain a solution comprising the recombinantly produced thermophilic enzyme having perhydrolytic activity; and
   e) concentrating the solution comprising the thermophilic enzyme of step (d) by filtration, evaporation or a combination of protein precipitation and redissolution whereby a concentrate is obtained comprising the recombinant thermophilic enzyme having perhydrolytic activity.

2. The process of claim 1, wherein the recombinantly-produced thermophilic enzyme having perhydrolytic activity comprises a carbohydrate esterase family 7 (CE-7) signature motif, said CE-7 signature motif comprising:
   (a) an RGQ motif corresponding to amino acid positions 118-120 of SEQ ID NO: 8;
   (b) a GXSQG motif corresponding to amino acid positions 186-190 of SEQ ID NO: 8; and
   (c) an HE motif corresponding to amino acid positions 303-304 of SEQ ID NO: 8.

3. The process of claim 2, wherein the thermophilic enzyme having perhydrolytic activity is an acetyl xylan esterase derived from a *Thermotoga* sp.

4. The process of claim 1, wherein the microbial cell homogenate of step (a) is an *Escherichia coli* cell homogenate.

5. The process of claim 1, wherein an exogenous nuclease is not present in steps (a) through (d).

6. The process of claim 1, wherein the first heat treatment period ranges from 4 hours to no more than 16 hours at a temperature ranging from 45° C. to 55° C.

7. The process of claim 1 or claim 6, wherein the second heat treatment period ranges from 30 minutes to 4 hours at a temperature ranging from 75° C. to 85° C.

8. The process of claim 1, wherein magnesium sulfate is present in the microbial cell homogenate.

9. The process of claim 1, wherein the weight percent (wt %) of recombinant thermophilic enzyme having perhydrolytic activity in the concentrate is at least 2.5 wt %.

10. The process of claim 9, wherein the weight percent (wt %) of recombinant thermophilic enzyme having perhydrolytic activity in the concentrate is at least 5.0 wt %.

11. The process of claim 1, wherein the removal of the solid components from the microbial cell homogenate obtained after performing step (b) and step (c) is performed in step (d) using filtration.

12. The process of claim 11, wherein the removal of the solid components from the microbial cell homogenate obtained after performing step (b) and step (c) is performed in step (d) using a membrane having size exclusion cutoffs ranging from 0.45 microns to 0.20 microns.

13. The process of claim 12, wherein the membrane retains particles greater than 0.2 microns in average diameter.

14. The process of claim 1, wherein the removal of the solid components from the microbial cell homogenate obtained after performing step (b) and step (c) is performed in step (d) using centrifugation.

15. The process of claim 1, wherein the concentration of the solution produced in step (d) is performed in step (e) using filtration.

16. The process of claim 15, wherein the concentration of the solution produced in step (d) is performed in step (e) using a membrane having size exclusion cutoffs ranging from 100 kDa to 30 kDa.

17. The process of claim 1, wherein the concentration of the solution produced in step (d) is performed in step (e) using evaporation.

18. The process of claim 1, wherein the concentration of the solution produced in step (d) is performed in step (e) using a combination of protein precipitation and redissolution.

* * * * *

SEQUENCE LISTING

```
<160> NUMBER OF SEQ ID NOS: 60

<210> SEQ ID NO 1
<211> LENGTH: 978
<212> TYPE: DNA
<213> ORGANISM: Thermotoga neapolitana

<400> SEQUENCE: 1
atggctttct tgacatgcc gctggaagaa ctgaaaaagt accgtccgga acgttacgag      60
gaaaaagact ttgacgaatt ttggcgcgaa accctgaaag aatccgaggg tttcccactg     120
gacccggtat tgaaaaagt tgacttccac ctgaagaccg tcgaaactta cgacgtcacc     180
ttcagcggtt atcgtggcca gcgtatcaaa ggttggctgc tggtaccgaa actggcggaa     240
gagaaactgc cgtgtgttgt tcagtacatt ggttacaacg gtggccgtgg tttcccgcac     300
gactggctgt tctggccgtc tatgggttac atctgcttcg ttatggacac ccgtggtcag     360
ggtagcggtt ggatgaaggg tgatactccg gactacccgg aaggtccggt ggacccgcag     420
tacccgggct tcatgacgcg cggcatcctg gatcctggca cctattacta ccgtcgtgtg     480
tttgtcgatg ccgtgcgcgc cgttgaagcc gctatcagct cccacgcgt cgattctcgt     540 aaagtggtag ttgctggtgg ctctcaaggt ggcggcattg cactggcagt ttccgcgctg     600
tccaaccgtg ttaaagccct gctgtgcgat gttccgttcc tgtgccactt ccgtcgtgcg     660
gtacagctgg tggacaccca cccgtacgta gaaattacga acttcctgaa aacccatcgt     720
gataaagaag agatcgtatt ccgtaccctg tcttactttg atggcgttaa ttttgcggct     780
cgtgcaaaag taccggcgct gttcagcgta ggtctgatgg acactatttg tccgccgtct     840
accgtattcg cagcctacaa ccactacgct ggtccgaaag aaatccgcat ctacccgtac     900
aacaaccacg aaggtggtgg ttcttttccag gcaatcgaac aggttaaatt cctgaaacgc     960
ctgttcgaag aaggctaa                                                  978
```

<210> SEQ ID NO 2
<211> LENGTH: 325
<212> TYPE: PRT
<213> ORGANISM: Thermotoga neapolitana

<400> SEQUENCE: 2

```
Met Ala Phe Phe Asp Met Pro Leu Glu Glu Leu Lys Lys Tyr Arg Pro
1               5                   10                  15

Glu Arg Tyr Glu Glu Lys Asp Phe Asp Glu Phe Trp Arg Glu Thr Leu
            20                  25                  30

Lys Glu Ser Glu Gly Phe Pro Leu Asp Pro Val Phe Glu Lys Val Asp
        35                  40                  45

Phe His Leu Lys Thr Val Glu Thr Tyr Asp Val Thr Phe Ser Gly Tyr
    50                  55                  60

Arg Gly Gln Arg Ile Lys Gly Trp Leu Leu Val Pro Lys Leu Ala Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Met Lys Gly Asp
        115                 120                 125

Thr Pro Asp Tyr Pro Glu Gly Pro Val Asp Pro Gln Tyr Pro Gly Phe
    130                 135                 140

Met Thr Arg Gly Ile Leu Asp Pro Gly Thr Tyr Tyr Tyr Arg Arg Val
145                 150                 155                 160

Phe Val Asp Ala Val Arg Ala Val Glu Ala Ile Ser Phe Pro Arg
                165                 170                 175

Val Asp Ser Arg Lys Val Val Ala Gly Ser Gln Gly Gly Gly
            180                 185                 190

Ile Ala Leu Ala Val Ser Ala Leu Ser Asn Arg Val Lys Ala Leu Leu
            195                 200                 205

Cys Asp Val Pro Phe Leu Cys His Phe Arg Arg Ala Val Gln Leu Val
            210                 215                 220

Asp Thr His Pro Tyr Val Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Val Pro Ala Leu Phe Ser Val Gly Leu
            260                 265                 270

Met Asp Thr Ile Cys Pro Pro Ser Thr Val Phe Ala Ala Tyr Asn His
        275                 280                 285

Tyr Ala Gly Pro Lys Glu Ile Arg Ile Tyr Pro Tyr Asn Asn His Glu
    290                 295                 300

Gly Gly Gly Ser Phe Gln Ala Ile Glu Gln Val Lys Phe Leu Lys Arg
305                 310                 315                 320

Leu Phe Glu Glu Gly
            325
```

<210> SEQ ID NO 3
<211> LENGTH: 325
<212> TYPE: PRT
<213> ORGANISM: artificial sequence
<220> FEATURE:
<223> OTHER INFORMATION: synthetic construct

<400> SEQUENCE: 3

```
Met Ala Phe Phe Asp Met Pro Leu Glu Glu Leu Lys Lys Tyr Arg Pro
1               5                   10                  15

Glu Arg Tyr Glu Glu Lys Asp Phe Asp Glu Phe Trp Arg Glu Thr Leu
            20                  25                  30

Lys Glu Ser Glu Gly Phe Pro Leu Asp Pro Val Phe Glu Lys Val Asp
        35                  40                  45

Phe His Leu Lys Thr Val Glu Thr Tyr Asp Val Thr Phe Ser Gly Tyr
    50                  55                  60

Arg Gly Gln Arg Ile Lys Gly Trp Leu Leu Val Pro Lys Leu Ala Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Met Lys Gly Asp
        115                 120                 125

Thr Pro Asp Tyr Pro Glu Gly Pro Val Asp Pro Gln Tyr Pro Gly Phe
    130                 135                 140

Met Thr Arg Gly Ile Leu Asp Pro Gly Thr Tyr Tyr Tyr Arg Arg Val
145                 150                 155                 160

Phe Val Asp Ala Val Arg Ala Val Glu Ala Ala Ile Ser Phe Pro Arg
                165                 170                 175

Val Asp Ser Arg Lys Val Val Ala Gly Ser Gln Gly Gly Gly
            180                 185                 190

Ile Ala Leu Ala Val Ser Ala Leu Ser Asn Arg Val Lys Ala Leu Leu
        195                 200                 205

Cys Asp Val Pro Phe Leu Cys His Phe Arg Arg Ala Val Gln Leu Val
    210                 215                 220

Asp Thr His Pro Tyr Val Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Val Pro Ala Leu Phe Ser Val Gly Leu
            260                 265                 270

Met Asp Thr Ile Ala Pro Pro Ser Thr Val Phe Ala Ala Tyr Asn His
        275                 280                 285

Tyr Ala Gly Pro Lys Glu Ile Arg Ile Tyr Pro Tyr Asn Asn His Glu
    290                 295                 300

Gly Gly Gly Ser Phe Gln Ala Ile Glu Gln Val Lys Phe Leu Lys Arg
305                 310                 315                 320

Leu Phe Glu Glu Gly
            325

<210> SEQ ID NO 4
<211> LENGTH: 325
<212> TYPE: PRT
<213> ORGANISM: artificial sequence
<220> FEATURE:
<223> OTHER INFORMATION: synthetic construct

<400> SEQUENCE: 4

Met Ala Phe Phe Asp Met Pro Leu Glu Glu Leu Lys Lys Tyr Arg Pro
1               5                   10                  15

Glu Arg Tyr Glu Glu Lys Asp Phe Asp Glu Phe Trp Arg Glu Thr Leu
            20                  25                  30

Lys Glu Ser Glu Gly Phe Pro Leu Asp Pro Val Phe Glu Lys Val Asp
```

```
                 35                  40                  45
Phe His Leu Lys Thr Val Glu Thr Tyr Asp Val Thr Phe Ser Gly Tyr
 50                  55                  60

Arg Gly Gln Arg Ile Lys Gly Trp Leu Leu Val Pro Lys Leu Ala Glu
 65                  70                  75                  80

Glu Lys Leu Pro Cys Val Val Gln Tyr Ile Gly Tyr Asn Gly Gly Arg
                 85                  90                  95

Gly Phe Pro His Asp Trp Leu Phe Trp Pro Ser Met Gly Tyr Ile Cys
                100                 105                 110

Phe Val Met Asp Thr Arg Gly Gln Gly Ser Gly Trp Met Lys Gly Asp
                115                 120                 125

Thr Pro Asp Tyr Pro Glu Gly Pro Val Asp Pro Gln Tyr Pro Gly Phe
                130                 135                 140

Met Thr Arg Gly Ile Leu Asp Pro Gly Thr Tyr Tyr Arg Arg Val
145                 150                 155                 160

Phe Val Asp Ala Val Arg Ala Val Glu Ala Ala Ile Ser Phe Pro Arg
                165                 170                 175

Val Asp Ser Arg Lys Val Val Ala Gly Ser Gln Gly Gly
                180                 185                 190

Ile Ala Leu Ala Val Ser Ala Leu Ser Asn Arg Val Lys Ala Leu Leu
                195                 200                 205

Cys Asp Val Pro Phe Leu Cys His Phe Arg Arg Ala Val Gln Leu Val
                210                 215                 220

Asp Thr His Pro Tyr Val Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Val Pro Ala Leu Phe Ser Val Gly Leu
                260                 265                 270

Met Asp Thr Ile Val Pro Pro Ser Thr Val Phe Ala Ala Tyr Asn His
                275                 280                 285

Tyr Ala Gly Pro Lys Glu Ile Arg Ile Tyr Pro Tyr Asn Asn His Glu
                290                 295                 300

Gly Gly Gly Ser Phe Gln Ala Ile Glu Gln Val Lys Phe Leu Lys Arg
305                 310                 315                 320

Leu Phe Glu Glu Gly
                325

<210> SEQ ID NO 5
<211> LENGTH: 325
<212> TYPE: PRT
<213> ORGANISM: artificial sequence
<220> FEATURE:
<223> OTHER INFORMATION: synthetic construct

<400> SEQUENCE: 5

Met Ala Phe Phe Asp Met Pro Leu Glu Glu Leu Lys Lys Tyr Arg Pro
 1               5                  10                  15

Glu Arg Tyr Glu Glu Lys Asp Phe Asp Glu Phe Trp Arg Glu Thr Leu
                 20                  25                  30

Lys Glu Ser Glu Gly Phe Pro Leu Asp Pro Val Phe Glu Lys Val Asp
                 35                  40                  45

Phe His Leu Lys Thr Val Glu Thr Tyr Asp Val Thr Phe Ser Gly Tyr
 50                  55                  60

Arg Gly Gln Arg Ile Lys Gly Trp Leu Leu Val Pro Lys Leu Ala Glu
 65                  70                  75                  80
```

```
Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Met Lys Gly Asp
        115                 120                 125

Thr Pro Asp Tyr Pro Glu Gly Pro Val Asp Pro Gln Tyr Pro Gly Phe
    130                 135                 140

Met Thr Arg Gly Ile Leu Asp Pro Gly Thr Tyr Tyr Arg Arg Val
145                 150                 155                 160

Phe Val Asp Ala Val Arg Ala Val Glu Ala Ala Ile Ser Phe Pro Arg
                165                 170                 175

Val Asp Ser Arg Lys Val Val Ala Gly Gly Ser Gln Gly Gly Gly
            180                 185                 190

Ile Ala Leu Ala Val Ser Ala Leu Ser Asn Arg Val Lys Ala Leu Leu
        195                 200                 205

Cys Asp Val Pro Phe Leu Cys His Phe Arg Arg Ala Val Gln Leu Val
    210                 215                 220

Asp Thr His Pro Tyr Val Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Val Pro Ala Leu Phe Ser Val Gly Leu
            260                 265                 270

Met Asp Thr Ile Ser Pro Pro Ser Thr Val Phe Ala Ala Tyr Asn His
        275                 280                 285

Tyr Ala Gly Pro Lys Glu Ile Arg Ile Tyr Pro Tyr Asn Asn His Glu
    290                 295                 300

Gly Gly Gly Ser Phe Gln Ala Ile Glu Gln Val Lys Phe Leu Lys Arg
305                 310                 315                 320

Leu Phe Glu Glu Gly
                325

<210> SEQ ID NO 6
<211> LENGTH: 325
<212> TYPE: PRT
<213> ORGANISM: artificial sequence
<220> FEATURE:
<223> OTHER INFORMATION: synthetic construct

<400> SEQUENCE: 6

Met Ala Phe Phe Asp Met Pro Leu Glu Glu Leu Lys Lys Tyr Arg Pro
1               5                   10                  15

Glu Arg Tyr Glu Glu Lys Asp Phe Asp Glu Phe Trp Arg Glu Thr Leu
            20                  25                  30

Lys Glu Ser Glu Gly Phe Pro Leu Asp Pro Val Phe Glu Lys Val Asp
        35                  40                  45

Phe His Leu Lys Thr Val Glu Thr Tyr Asp Val Thr Phe Ser Gly Tyr
    50                  55                  60

Arg Gly Gln Arg Ile Lys Gly Trp Leu Leu Val Pro Lys Leu Ala Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110
```

```
Phe Val Met Asp Thr Arg Gly Gln Gly Ser Gly Trp Met Lys Gly Asp
        115                 120                 125

Thr Pro Asp Tyr Pro Glu Gly Pro Val Asp Pro Gln Tyr Pro Gly Phe
    130                 135                 140

Met Thr Arg Gly Ile Leu Asp Pro Gly Thr Tyr Tyr Arg Arg Val
145                 150                 155                 160

Phe Val Asp Ala Val Arg Ala Val Glu Ala Ala Ile Ser Phe Pro Arg
                165                 170                 175

Val Asp Ser Arg Lys Val Val Ala Gly Ser Gln Gly Gly
            180                 185                 190

Ile Ala Leu Ala Val Ser Ala Leu Ser Asn Arg Val Lys Ala Leu Leu
        195                 200                 205

Cys Asp Val Pro Phe Leu Cys His Phe Arg Arg Ala Val Gln Leu Val
    210                 215                 220

Asp Thr His Pro Tyr Val Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Val Pro Ala Leu Phe Ser Val Gly Leu
            260                 265                 270

Met Asp Thr Ile Thr Pro Pro Ser Thr Val Phe Ala Ala Tyr Asn His
        275                 280                 285

Tyr Ala Gly Pro Lys Glu Ile Arg Ile Tyr Pro Tyr Asn Asn His Glu
    290                 295                 300

Gly Gly Gly Ser Phe Gln Ala Ile Glu Gln Val Lys Phe Leu Lys Arg
305                 310                 315                 320

Leu Phe Glu Glu Gly
            325

<210> SEQ ID NO 7
<211> LENGTH: 975
<212> TYPE: DNA
<213> ORGANISM: Thermotoga maritima

<400> SEQUENCE: 7
atggcgttct tcgacctgcc tctggaagaa ctgaagaaat accgtccaga gcgttacgaa      60
gagaaggact cgacgagtt ctgggaggaa actctggcgg agagcgaaaa gtttccgctg     120
gacccagtgt tcgagcgtat ggaatctcac ctgaaaaccg tggaggcata tgacgttact     180
ttttctggtt accgtggcca gcgtatcaaa ggctggctgc tggttccgaa actggaggaa     240
gaaaaactgc cgtgcgtagt tcagtacatc ggttacaacg gtggccgtgg ctttccgcac     300
gattggctgt tctggccgtc tatgggctac atttgcttcg tcatggatac tcgtggtcag     360
ggttccggct ggctgaaagg cgatactccg gattatccgg agggcccggt agacccgcag     420
tacccctggct tcatgacgcg tggtattctg gatccgcgta cctattacta cgccgcgtt     480
tttaccgatg cagttcgtgc cgtagaggcc gcggcttctt ccctcaggt tgaccaggag     540
cgtattgtta tcgctggtgg ctcccagggt ggcggcatcg ccctggcggt atctgcgctg     600
agcaagaaag ctaaggcact gctgtgtgac gtcccgttcc tgtgtcactt ccgtcgcgct     660
gttcagctgg tagatacccca tccgtacgcg gagattacta cttcctgaa aactcaccgc     720
gacaaagaag aaatcgtttt ccgcaccctg tcctatttcg acggcgttaa cttcgcggct     780
cgtgcaaaaa ttccggcact gttctctgtt ggtctgatgg acaacatctg ccctccttct     840
accgttttcg cggcatataa ctattatgcg ggtccgaaag aaatccgtat ctatccgtac     900
```

```
aacaaccacg aaggcggtgg tagctttcag gctgttgaac aagtgaaatt cctgaagaaa    960
ctgtttgaga agggc                                                     975
```

<210> SEQ ID NO 8
<211> LENGTH: 325
<212> TYPE: PRT
<213> ORGANISM: Thermotoga maritima

<400> SEQUENCE: 8

```
Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Glu Thr Leu
            20                  25                  30

Ala Glu Ser Glu Lys Phe Pro Leu Asp Pro Val Phe Glu Arg Met Glu
        35                  40                  45

Ser His Leu Lys Thr Val Glu Ala Tyr Asp Val Thr Phe Ser Gly Tyr
    50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
        115                 120                 125

Thr Pro Asp Tyr Pro Glu Gly Pro Val Asp Pro Gln Tyr Pro Gly Phe
    130                 135                 140

Met Thr Arg Gly Ile Leu Asp Pro Arg Thr Tyr Tyr Tyr Arg Arg Val
145                 150                 155                 160

Phe Thr Asp Ala Val Arg Ala Val Glu Ala Ala Ser Phe Pro Gln
                165                 170                 175

Val Asp Gln Glu Arg Ile Val Ile Ala Gly Ser Gln Gly Gly Gly
            180                 185                 190

Ile Ala Leu Ala Val Ser Ala Leu Ser Lys Ala Lys Ala Leu Leu
        195                 200                 205

Cys Asp Val Pro Phe Leu Cys His Phe Arg Arg Ala Val Gln Leu Val
210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Ile Pro Ala Leu Phe Ser Val Gly Leu
            260                 265                 270

Met Asp Asn Ile Cys Pro Pro Ser Thr Val Phe Ala Ala Tyr Asn Tyr
        275                 280                 285

Tyr Ala Gly Pro Lys Glu Ile Arg Ile Tyr Pro Tyr Asn Asn His Glu
    290                 295                 300

Gly Gly Gly Ser Phe Gln Ala Val Glu Gln Val Lys Phe Leu Lys Lys
305                 310                 315                 320

Leu Phe Glu Lys Gly
                325
```

<210> SEQ ID NO 9
<211> LENGTH: 325
<212> TYPE: PRT
<213> ORGANISM: artificial sequence
<220> FEATURE:
<223> OTHER INFORMATION: synthetic construct

<400> SEQUENCE: 9

```
Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Glu Thr Leu
            20                  25                  30

Ala Glu Ser Glu Lys Phe Pro Leu Asp Pro Val Phe Glu Arg Met Glu
        35                  40                  45

Ser His Leu Lys Thr Val Glu Ala Tyr Asp Val Thr Phe Ser Gly Tyr
    50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
        115                 120                 125

Thr Pro Asp Tyr Pro Glu Gly Pro Val Asp Pro Gln Tyr Pro Gly Phe
    130                 135                 140

Met Thr Arg Gly Ile Leu Asp Pro Arg Thr Tyr Tyr Arg Arg Val
145                 150                 155                 160

Phe Thr Asp Ala Val Arg Ala Val Glu Ala Ala Ser Phe Pro Gln
                165                 170                 175

Val Asp Gln Glu Arg Ile Val Ile Ala Gly Gly Ser Gln Gly Gly
            180                 185                 190

Ile Ala Leu Ala Val Ser Ala Leu Ser Lys Lys Ala Lys Ala Leu Leu
        195                 200                 205

Cys Asp Val Pro Phe Leu Cys His Phe Arg Arg Ala Val Gln Leu Val
    210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Ile Pro Ala Leu Phe Ser Val Gly Leu
            260                 265                 270

Met Asp Asn Ile Ala Pro Pro Ser Thr Val Phe Ala Ala Tyr Asn Tyr
        275                 280                 285

Tyr Ala Gly Pro Lys Glu Ile Arg Ile Tyr Pro Tyr Asn Asn His Glu
    290                 295                 300

Gly Gly Gly Ser Phe Gln Ala Val Glu Gln Val Lys Phe Leu Lys Lys
305                 310                 315                 320

Leu Phe Glu Lys Gly
            325
```

<210> SEQ ID NO 10
<211> LENGTH: 325
<212> TYPE: PRT
<213> ORGANISM: artificial sequence
<220> FEATURE:
<223> OTHER INFORMATION: synthetic construct

<400> SEQUENCE: 10

```
Met Ala Phe Phe Asp Leu Pro Leu Glu Glu Leu Lys Lys Tyr Arg Pro
1               5                   10                  15
```

```
Glu Arg Tyr Glu Glu Lys Asp Phe Asp Glu Phe Trp Glu Glu Thr Leu
             20                  25                  30

Ala Glu Ser Glu Lys Phe Pro Leu Asp Pro Val Phe Glu Arg Met Glu
             35                  40                  45

Ser His Leu Lys Thr Val Glu Ala Tyr Asp Val Thr Phe Ser Gly Tyr
             50                  55                  60

Arg Gly Gln Arg Ile Lys Gly Trp Leu Leu Val Pro Lys Leu Glu Glu
 65                  70                  75                  80

Glu Lys Leu Pro Cys Val Val Gln Tyr Ile Gly Tyr Asn Gly Gly Arg
                 85                  90                  95

Gly Phe Pro His Asp Trp Leu Phe Trp Pro Ser Met Gly Tyr Ile Cys
                100                 105                 110

Phe Val Met Asp Thr Arg Gly Gln Gly Ser Gly Trp Leu Lys Gly Asp
            115                 120                 125

Thr Pro Asp Tyr Pro Glu Gly Pro Val Asp Pro Gln Tyr Pro Gly Phe
130                 135                 140

Met Thr Arg Gly Ile Leu Asp Pro Arg Thr Tyr Tyr Arg Arg Val
145                 150                 155                 160

Phe Thr Asp Ala Val Arg Ala Val Glu Ala Ala Ser Phe Pro Gln
                165                 170                 175

Val Asp Gln Glu Arg Ile Val Ile Ala Gly Ser Gly Gly Gly
            180                 185                 190

Ile Ala Leu Ala Val Ser Ala Leu Ser Lys Lys Ala Lys Ala Leu Leu
                195                 200                 205

Cys Asp Val Pro Phe Leu Cys His Phe Arg Arg Ala Val Gln Leu Val
210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Ile Pro Ala Leu Phe Ser Val Gly Leu
                260                 265                 270

Met Asp Asn Ile Val Pro Pro Ser Thr Val Phe Ala Ala Tyr Asn Tyr
                275                 280                 285

Tyr Ala Gly Pro Lys Glu Ile Arg Ile Tyr Pro Tyr Asn Asn His Glu
            290                 295                 300

Gly Gly Gly Ser Phe Gln Ala Val Glu Gln Val Lys Phe Leu Lys Lys
305                 310                 315                 320

Leu Phe Glu Lys Gly
            325

<210> SEQ ID NO 11
<211> LENGTH: 325
<212> TYPE: PRT
<213> ORGANISM: artificial sequence
<220> FEATURE:
<223> OTHER INFORMATION: synthetic construct

<400> SEQUENCE: 11

Met Ala Phe Phe Asp Leu Pro Leu Glu Glu Leu Lys Lys Tyr Arg Pro
  1               5                  10                  15

Glu Arg Tyr Glu Glu Lys Asp Phe Asp Glu Phe Trp Glu Glu Thr Leu
             20                  25                  30

Ala Glu Ser Glu Lys Phe Pro Leu Asp Pro Val Phe Glu Arg Met Glu
             35                  40                  45
```

```
Ser His Leu Lys Thr Val Glu Ala Tyr Asp Val Thr Phe Ser Gly Tyr
    50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
            115                 120                 125

Thr Pro Asp Tyr Pro Glu Gly Pro Val Asp Pro Gln Tyr Pro Gly Phe
        130                 135                 140

Met Thr Arg Gly Ile Leu Asp Pro Arg Thr Tyr Tyr Arg Arg Val
145                 150                 155                 160

Phe Thr Asp Ala Val Arg Ala Val Glu Ala Ala Ser Phe Pro Gln
                165                 170                 175

Val Asp Gln Glu Arg Ile Val Ile Ala Gly Gly Ser Gln Gly Gly
            180                 185                 190

Ile Ala Leu Ala Val Ser Ala Leu Ser Lys Ala Lys Ala Leu Leu
            195                 200                 205

Cys Asp Val Pro Phe Leu Cys His Phe Arg Arg Ala Val Gln Leu Val
        210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Ile Pro Ala Leu Phe Ser Val Gly Leu
            260                 265                 270

Met Asp Asn Ile Ser Pro Pro Ser Thr Val Phe Ala Ala Tyr Asn Tyr
            275                 280                 285

Tyr Ala Gly Pro Lys Glu Ile Arg Ile Tyr Pro Tyr Asn Asn His Glu
        290                 295                 300

Gly Gly Gly Ser Phe Gln Ala Val Glu Gln Val Lys Phe Leu Lys Lys
305                 310                 315                 320

Leu Phe Glu Lys Gly
            325

<210> SEQ ID NO 12
<211> LENGTH: 325
<212> TYPE: PRT
<213> ORGANISM: artificial sequence
<220> FEATURE:
<223> OTHER INFORMATION: synthetic construct

<400> SEQUENCE: 12

Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Glu Thr Leu
            20                  25                  30

Ala Glu Ser Glu Lys Phe Pro Leu Asp Pro Val Phe Glu Arg Met Glu
        35                  40                  45

Ser His Leu Lys Thr Val Glu Ala Tyr Asp Val Thr Phe Ser Gly Tyr
    50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
```

-continued

```
                85                  90                  95
Gly Phe Pro His Asp Trp Leu Phe Trp Pro Ser Met Gly Tyr Ile Cys
            100                 105                 110
Phe Val Met Asp Thr Arg Gly Gln Gly Ser Gly Trp Leu Lys Gly Asp
            115                 120                 125
Thr Pro Asp Tyr Pro Glu Gly Pro Val Asp Pro Gln Tyr Pro Gly Phe
            130                 135                 140
Met Thr Arg Gly Ile Leu Asp Pro Arg Thr Tyr Tyr Arg Arg Val
145                 150                 155                 160
Phe Thr Asp Ala Val Arg Ala Val Glu Ala Ala Ser Phe Pro Gln
                165                 170                 175
Val Asp Gln Glu Arg Ile Val Ile Ala Gly Gly Ser Gln Gly Gly
                180                 185                 190
Ile Ala Leu Ala Val Ser Ala Leu Ser Lys Ala Lys Ala Leu Leu
                195                 200                 205
Cys Asp Val Pro Phe Leu Cys His Phe Arg Arg Ala Val Gln Leu Val
210                 215                 220
Asp Thr His Pro Tyr Ala Glu Ile Thr Asn Phe Leu Lys Thr His Arg
225                 230                 235                 240
Asp Lys Glu Glu Ile Val Phe Arg Thr Leu Ser Tyr Phe Asp Gly Val
                245                 250                 255
Asn Phe Ala Ala Arg Ala Lys Ile Pro Ala Leu Phe Ser Val Gly Leu
                260                 265                 270
Met Asp Asn Ile Thr Pro Pro Ser Thr Val Phe Ala Ala Tyr Asn Tyr
                275                 280                 285
Tyr Ala Gly Pro Lys Glu Ile Arg Ile Tyr Pro Tyr Asn Asn His Glu
                290                 295                 300
Gly Gly Gly Ser Phe Gln Ala Val Glu Gln Val Lys Phe Leu Lys Lys
305                 310                 315                 320
Leu Phe Glu Lys Gly
                325

<210> SEQ ID NO 13
<211> LENGTH: 325
<212> TYPE: PRT
<213> ORGANISM: artificial sequence
<220> FEATURE:
<223> OTHER INFORMATION: synthetic construct

<400> SEQUENCE: 13

Met Ala Phe Phe Asp Leu Pro Leu Glu Glu Leu Lys Lys Tyr Arg Pro
1               5                   10                  15
Glu Arg Tyr Glu Glu Lys Asp Ile Asp Glu Phe Trp Glu Glu Thr Leu
                20                  25                  30
Ala Glu Thr Glu Lys Phe Pro Leu Asp Pro Val Phe Glu Arg Met Glu
                35                  40                  45
Ser His Leu Lys Thr Val Glu Ala Tyr Asp Val Thr Phe Ser Gly Tyr
                50                  55                  60
Arg Gly Gln Arg Ile Lys Gly Trp Leu Leu Val Pro Lys Leu Glu Glu
65                  70                  75                  80
Glu Lys Leu Pro Cys Val Val Gln Tyr Ile Gly Tyr Asn Gly Gly Arg
                85                  90                  95
Gly Phe Pro His Asp Trp Leu Phe Trp Pro Ser Met Gly Tyr Ile Cys
            100                 105                 110
Phe Val Met Asp Thr Arg Gly Gln Gly Ser Gly Trp Leu Lys Gly Asp
            115                 120                 125
```

```
Thr Pro Asp Tyr Pro Glu Gly Pro Val Asp Pro Gln Tyr Pro Gly Phe
        130                 135                 140

Met Thr Arg Gly Ile Leu Asp Pro Arg Thr Tyr Tyr Arg Arg Val
145                 150                 155                 160

Phe Thr Asp Ala Val Arg Ala Val Glu Ala Ala Ser Phe Pro Gln
                165                 170                 175

Val Asp Leu Glu Arg Ile Val Ile Ala Gly Gly Ser Gln Gly Gly Gly
            180                 185                 190

Ile Ala Leu Ala Val Ser Ala Leu Ser Lys Lys Ala Lys Ala Leu Leu
        195                 200                 205

Cys Asp Val Pro Phe Leu Cys His Phe Arg Arg Ala Val Gln Leu Val
        210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Ile Pro Ala Leu Phe Ser Val Gly Leu
            260                 265                 270

Met Asp Asp Ile Ser Pro Pro Ser Thr Val Phe Ala Ala Tyr Asn Tyr
        275                 280                 285

Tyr Ala Gly Pro Lys Glu Ile Arg Ile Tyr Pro Tyr Asn Asn His Glu
        290                 295                 300

Gly Gly Gly Gly Phe Gln Ala Val Glu Gln Val Lys Ser Leu Lys Lys
305                 310                 315                 320

Leu Phe Glu Lys Gly
            325

<210> SEQ ID NO 14
<211> LENGTH: 325
<212> TYPE: PRT
<213> ORGANISM: artificial sequence
<220> FEATURE:
<223> OTHER INFORMATION: synthetic construct

<400> SEQUENCE: 14

Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Glu Thr Leu
            20                  25                  30

Ala Glu Ser Glu Lys Phe Pro Leu Asp Pro Val Phe Glu Arg Met Glu
        35                  40                  45

Ser His Leu Lys Thr Val Glu Ala Tyr Asp Val Thr Phe Ser Gly Tyr
    50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
        115                 120                 125

Thr Pro Asp Tyr Pro Glu Gly Pro Val Asp Pro Gln Tyr Pro Gly Phe
    130                 135                 140

Met Thr Arg Gly Ile Leu Asp Pro Arg Thr Tyr Tyr Tyr Arg Arg Val
145                 150                 155                 160
```

```
Phe Thr Asp Ala Val Arg Ala Val Glu Ala Ala Ala Ser Phe Pro Gln
                165                 170                 175

Val Asp Gln Glu Arg Ile Val Ile Ala Gly Gly Ser Gln Gly Gly Gly
            180                 185                 190

Ile Ala Leu Ala Val Ser Ala Leu Ser Lys Lys Ala Lys Ala Leu Leu
        195                 200                 205

Cys Asp Val Pro Phe Leu Cys His Phe Arg Arg Ala Val Gln Leu Val
        210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Ile Pro Ala Leu Phe Ser Val Gly Leu
            260                 265                 270

Met Asp Asp Ile Ser Pro Pro Ser Thr Val Phe Ala Ala Tyr Asn Tyr
        275                 280                 285

Tyr Ala Gly Pro Lys Glu Ile Arg Ile Tyr Pro Tyr Asn Asn His Glu
            290                 295                 300

Gly Gly Gly Ser Phe Gln Ala Val Glu Gln Val Lys Phe Leu Lys Lys
305                 310                 315                 320

Leu Phe Glu Lys Gly
                325

<210> SEQ ID NO 15
<211> LENGTH: 325
<212> TYPE: PRT
<213> ORGANISM: artificial sequence
<220> FEATURE:
<223> OTHER INFORMATION: synthetic construct

<400> SEQUENCE: 15

Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Glu Thr Leu
                20                  25                  30

Ala Glu Ser Glu Lys Phe Pro Leu Asp Pro Val Phe Glu Arg Met Glu
            35                  40                  45

Ser His Leu Lys Thr Val Glu Ala Tyr Asp Val Thr Phe Ser Gly Tyr
        50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
        115                 120                 125

Thr Pro Asp Tyr Pro Glu Gly Pro Val Asp Pro Gln Tyr Pro Gly Phe
    130                 135                 140

Met Thr Arg Gly Ile Leu Asp Pro Arg Thr Tyr Tyr Tyr Arg Arg Val
145                 150                 155                 160

Phe Thr Asp Ala Val Arg Ala Val Glu Ala Ala Ala Ser Phe Pro Gln
                165                 170                 175

Val Asp Gln Glu Arg Ile Val Ile Ala Gly Gly Ser Gln Gly Gly Gly
            180                 185                 190

Ile Ala Leu Ala Val Ser Ala Leu Ser Lys Lys Ala Lys Ala Leu Leu
```

```
                195                 200                 205
Cys Asp Val Pro Phe Leu Cys His Phe Arg Arg Ala Val Gln Leu Val
210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Ile Pro Ala Leu Phe Ser Val Gly Leu
                260                 265                 270

Met Asp Asn Ile Ser Pro Pro Ser Thr Val Phe Ala Ala Tyr Asn Tyr
                275                 280                 285

Tyr Ala Gly Pro Lys Glu Ile Arg Ile Tyr Pro Tyr Asn Asn His Glu
                290                 295                 300

Gly Gly Gly Ser Phe Gln Ala Val Glu Gln Val Lys Ser Leu Lys Lys
305                 310                 315                 320

Leu Phe Glu Lys Gly
                325

<210> SEQ ID NO 16
<211> LENGTH: 325
<212> TYPE: PRT
<213> ORGANISM: artificial sequence
<220> FEATURE:
<223> OTHER INFORMATION: synthetic construct

<400> SEQUENCE: 16

Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Glu Thr Leu
                20                  25                  30

Ala Glu Thr Glu Lys Phe Pro Leu Asp Pro Val Phe Glu Arg Met Glu
                35                  40                  45

Ser His Leu Lys Thr Val Glu Ala Tyr Asp Val Thr Phe Ser Gly Tyr
                50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
                100                 105                 110

Phe Val Met Asp Thr Arg Gly Gln Gly Ser Gly Trp Leu Lys Gly Asp
                115                 120                 125

Thr Pro Asp Tyr Pro Glu Gly Pro Val Asp Pro Gln Tyr Pro Gly Phe
                130                 135                 140

Met Thr Arg Gly Ile Leu Asp Pro Arg Thr Tyr Tyr Tyr Arg Arg Val
145                 150                 155                 160

Phe Thr Asp Ala Val Arg Ala Val Glu Ala Ala Ser Phe Pro Gln
                165                 170                 175

Val Asp Gln Glu Arg Ile Val Ile Ala Gly Gly Ser Gln Gly Gly Gly
                180                 185                 190

Ile Ala Leu Ala Val Ser Ala Leu Ser Lys Lys Ala Lys Ala Leu Leu
                195                 200                 205

Cys Asp Val Pro Phe Leu Cys His Phe Arg Arg Ala Val Gln Leu Val
210                 215                 220

Asp Thr His Pro Tyr Ala Glu Ile Thr Asn Phe Leu Lys Thr His Arg
225                 230                 235                 240
```

```
Asp Lys Glu Glu Ile Val Phe Arg Thr Leu Ser Tyr Phe Asp Gly Val
            245                 250                 255

Asn Phe Ala Ala Arg Ala Lys Ile Pro Ala Leu Phe Ser Val Gly Leu
        260                 265                 270

Met Asp Asn Ile Ser Pro Pro Ser Thr Val Phe Ala Ala Tyr Asn Tyr
            275                 280                 285

Tyr Ala Gly Pro Lys Glu Ile Arg Ile Tyr Pro Tyr Asn Asn His Glu
        290                 295                 300

Gly Gly Gly Ser Phe Gln Ala Val Glu Gln Val Lys Phe Leu Lys Lys
305                 310                 315                 320

Leu Phe Glu Lys Gly
            325

<210> SEQ ID NO 17
<211> LENGTH: 325
<212> TYPE: PRT
<213> ORGANISM: artificial sequence
<220> FEATURE:
<223> OTHER INFORMATION: synthetic construct

<400> SEQUENCE: 17

Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Glu Thr Leu
            20                  25                  30

Ala Glu Ser Glu Lys Phe Pro Leu Asp Pro Val Phe Glu Arg Met Glu
        35                  40                  45

Ser His Leu Lys Thr Val Glu Ala Tyr Asp Val Thr Phe Ser Gly Tyr
    50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
        115                 120                 125

Thr Pro Asp Tyr Pro Glu Gly Pro Val Asp Pro Gln Tyr Pro Gly Phe
    130                 135                 140

Met Thr Arg Gly Ile Leu Asp Pro Arg Thr Tyr Tyr Tyr Arg Arg Val
145                 150                 155                 160

Phe Thr Asp Ala Val Arg Ala Val Glu Ala Ala Ala Ser Phe Pro Gln
                165                 170                 175

Val Asp Leu Glu Arg Ile Val Ile Ala Gly Gly Ser Gln Gly Gly Gly
            180                 185                 190

Ile Ala Leu Ala Val Ser Ala Leu Ser Lys Lys Ala Lys Ala Leu Leu
        195                 200                 205

Cys Asp Val Pro Phe Leu Cys His Phe Arg Arg Ala Val Gln Leu Val
    210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Ile Pro Ala Leu Phe Ser Val Gly Leu
            260                 265                 270
```

```
Met Asp Asn Ile Ser Pro Pro Ser Thr Val Phe Ala Ala Tyr Asn Tyr
            275                 280                 285

Tyr Ala Gly Pro Lys Glu Ile Arg Ile Tyr Pro Tyr Asn Asn His Glu
            290                 295                 300

Gly Gly Gly Ser Phe Gln Ala Val Glu Gln Val Lys Phe Leu Lys Lys
305                 310                 315                 320

Leu Phe Glu Lys Gly
                325

<210> SEQ ID NO 18
<211> LENGTH: 325
<212> TYPE: PRT
<213> ORGANISM: artificial sequence
<220> FEATURE:
<223> OTHER INFORMATION: synthetic construct

<400> SEQUENCE: 18

Met Ala Phe Phe Asp Leu Pro Arg Glu Glu Leu Lys Lys Tyr Arg Pro
1               5                   10                  15

Glu Arg Tyr Glu Glu Lys Asp Phe Asp Glu Phe Trp Glu Glu Thr Leu
            20                  25                  30

Ala Glu Ser Glu Lys Phe Pro Leu Asp Pro Val Phe Glu Arg Met Glu
            35                  40                  45

Ser His Leu Lys Thr Val Glu Ala Tyr Asp Val Thr Phe Ser Gly Tyr
    50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Gln Lys Gly Asp
            115                 120                 125

Thr Pro Asp Tyr Pro Glu Gly Pro Val Asp Pro Gln Tyr Pro Gly Phe
    130                 135                 140

Met Thr Arg Gly Ile Leu Asp Pro Arg Thr Tyr Tyr Arg Arg Val
145                 150                 155                 160

Phe Thr Asp Ala Val Arg Ala Val Glu Ala Ala Ser Phe Pro Leu
                165                 170                 175

Val Asp Gln Glu Arg Ile Asp Ile Ala Gly Gly Ser Gln Gly Gly Gly
            180                 185                 190

Ile Ala Leu Ala Val Ser Ala Leu Ser Lys Lys Ala Lys Ala Leu Leu
        195                 200                 205

Cys Asp Val Pro Phe Leu Cys His Phe Arg Arg Ala Val Gln Leu Val
    210                 215                 220

Asp Thr His Pro Tyr Ala Glu Ile Thr Asn Phe Leu Lys Thr His Arg
225                 230                 235                 240

Asp Lys Glu Glu Ile Val Ile Arg Thr Leu Ser Tyr Phe Asp Gly Val
                245                 250                 255

Asn Phe Ala Ala Arg Ala Lys Ile Pro Ala Leu Phe Ser Val Gly Leu
            260                 265                 270

Met Asp Asn Ile Ser Pro Pro Ser Thr Val Phe Ala Ala Tyr Asn Tyr
            275                 280                 285

Tyr Ala Gly Leu Lys Glu Ile Arg Ile Tyr Pro Tyr Asn Asn His Glu
            290                 295                 300

Gly Gly Gly Ser Phe Gln Ala Val Glu Gln Val Lys Phe Leu Lys Lys
```

Leu Phe Glu Lys Gly
            325

<210> SEQ ID NO 19
<211> LENGTH: 325
<212> TYPE: PRT
<213> ORGANISM: artificial sequence
<220> FEATURE:
<223> OTHER INFORMATION: synthetic construct

<400> SEQUENCE: 19

Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Glu Thr Leu
            20                  25                  30

Ala Glu Ser Glu Lys Phe Pro Leu Asp Pro Val Phe Glu Arg Met Glu
        35                  40                  45

Ser His Leu Lys Thr Val Glu Ala Tyr Asp Val Thr Phe Ser Gly Tyr
    50                  55                  60

Arg Gly Gln Arg Ile Lys Gly Trp Leu Leu Val Pro Glu Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
        115                 120                 125

Thr Pro Asp Tyr Pro Glu Gly Pro Val Asp Pro Gln Tyr Pro Gly Phe
    130                 135                 140

Met Thr Arg Gly Ile Leu Asp Pro Arg Thr Tyr Tyr Arg Arg Val
145                 150                 155                 160

Phe Thr Asp Ala Val Arg Ala Val Glu Ala Ala Ser Phe Pro Gln
                165                 170                 175

Val Asp Gln Glu Arg Ile Val Ile Ala Gly Gly Ser Gln Gly Gly Gly
            180                 185                 190

Ile Ala Leu Ala Val Ser Ala Leu Ser Lys Lys Ala Lys Ala Leu Leu
        195                 200                 205

Cys Asp Val Pro Phe Leu Cys His Phe Arg Arg Ala Val Gln Leu Val
    210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Ile Pro Glu Leu Phe Ser Val Gly Leu
            260                 265                 270

Met Asp Asn Ile Ser Pro Pro Ser Thr Val Phe Ala Ala Tyr Asn Tyr
        275                 280                 285

Tyr Ala Gly Pro Lys Glu Ile Arg Ile Tyr Pro Tyr Asn Asn His Glu
    290                 295                 300

Gly Gly Gly Ser Phe Gln Ala Val Glu Gln Val Lys Phe Leu Lys Lys
305                 310                 315                 320

Leu Phe Glu Lys Gly
            325

<210> SEQ ID NO 20

<211> LENGTH: 325
<212> TYPE: PRT
<213> ORGANISM: artificial sequence
<220> FEATURE:
<223> OTHER INFORMATION: synthetic construct

<400> SEQUENCE: 20

```
Met Ala Phe Phe Asp Leu Pro Leu Glu Glu Leu Lys Lys Tyr Arg Pro
1               5                   10                  15
Glu Arg Tyr Glu Glu Lys Asp Phe Asp Glu Tyr Trp Glu Glu Thr Leu
            20                  25                  30
Ala Glu Ser Glu Lys Phe Pro Leu Asp Pro Val Phe Glu Arg Met Glu
        35                  40                  45
Ser His Leu Lys Thr Val Glu Ala Tyr Asp Val Thr Phe Ser Gly Tyr
    50                  55                  60
Arg Gly Gln Arg Ile Lys Gly Trp Leu Leu Val Pro Lys Leu Glu Glu
65                  70                  75                  80
Glu Lys Leu Pro Cys Val Val Gln Tyr Ile Gly Tyr Asn Gly Gly Arg
                85                  90                  95
Gly Phe Pro His Asp Trp Leu Phe Trp Pro Ser Met Gly Tyr Ile Cys
            100                 105                 110
Phe Val Met Asp Thr Arg Gly Gln Gly Ser Gly Trp Leu Lys Gly Asp
        115                 120                 125
Thr Pro Asp Tyr Pro Glu Gly Pro Val Asp Pro Gln Tyr Pro Gly Phe
    130                 135                 140
Met Thr Arg Gly Val Leu Asp Pro Arg Thr Tyr Tyr Arg Arg Val
145                 150                 155                 160
Phe Thr Asp Ala Val Arg Ala Val Glu Ala Ala Ser Phe Pro Gln
                165                 170                 175
Val Asp Gln Glu Arg Ile Val Ile Ala Gly Ser Gln Gly Gly Gly
            180                 185                 190
Ile Ala Leu Ala Val Ser Ala Leu Ser Lys Ala Lys Ala Leu Leu
        195                 200                 205
Cys Asp Val Pro Phe Leu Cys His Phe Arg Arg Ala Val Gln Leu Val
    210                 215                 220
Asp Thr His Pro Tyr Ala Glu Ile Thr Asn Phe Leu Lys Thr His Arg
225                 230                 235                 240
Asp Lys Glu Glu Ile Val Phe Arg Thr Leu Ser Tyr Phe Asp Gly Val
                245                 250                 255
Asn Phe Ala Ala Arg Ala Lys Ile Pro Val Leu Phe Ser Val Gly Leu
            260                 265                 270
Met Asp Asn Ile Ser Pro Pro Ser Thr Val Phe Ala Ala Tyr Asn Tyr
        275                 280                 285
Tyr Ala Gly Pro Lys Glu Thr Arg Ile Tyr Pro Tyr Asn Ser His Glu
    290                 295                 300
Gly Gly Gly Ser Phe Gln Ala Val Glu Gln Val Lys Phe Leu Lys Lys
305                 310                 315                 320
Leu Phe Glu Lys Gly
            325
```

<210> SEQ ID NO 21
<211> LENGTH: 325
<212> TYPE: PRT
<213> ORGANISM: artificial sequence
<220> FEATURE:
<223> OTHER INFORMATION: synthetic construct

<400> SEQUENCE: 21

```
Met Ala Phe Phe Asp Leu Pro Leu Glu Glu Leu Lys Lys Tyr Arg Pro
1               5                   10                  15
Glu Arg Tyr Glu Glu Lys Asp Phe Asp Glu Phe Trp Glu Glu Thr Leu
            20                  25                  30
Ala Glu Ser Glu Lys Phe Pro Leu Asp Pro Val Phe Glu Arg Met Glu
        35                  40                  45
Ser His Leu Lys Thr Val Glu Ala Tyr Asp Val Thr Phe Ser Gly Tyr
    50                  55                  60
Arg Gly Gln Arg Ile Lys Gly Trp Leu Leu Val Pro Lys Leu Glu Glu
65                  70                  75                  80
Glu Lys Leu Pro Cys Val Val Gln Tyr Ile Gly Tyr Asn Gly Gly Arg
                85                  90                  95
Gly Phe Pro His Asp Trp Leu Phe Trp Pro Ser Met Gly Tyr Ile Cys
            100                 105                 110
Phe Val Met Asp Thr Arg Gly Gln Gly Ser Gly Trp Leu Lys Gly Asp
        115                 120                 125
Thr Pro Asp Tyr Pro Glu Gly Pro Val Asp Pro Gln Tyr Pro Gly Phe
    130                 135                 140
Met Thr Arg Gly Ile Leu Asp Pro Arg Thr Tyr Tyr Arg Arg Val
145                 150                 155                 160
Phe Thr Asp Ala Val Arg Ala Val Glu Ala Ala Ser Phe Pro Gln
                165                 170                 175
Val Asp Gln Glu Arg Ile Val Ile Ala Gly Gly Ser Gln Gly Gly Gly
            180                 185                 190
Ile Ala Gln Ala Val Ser Ala Leu Ser Lys Lys Ala Lys Ala Leu Leu
        195                 200                 205
Cys Asp Val Pro Phe Leu Cys His Phe Arg Arg Ala Val Gln Leu Val
    210                 215                 220
Asp Thr His Pro Tyr Ala Glu Ile Thr Asn Phe Leu Lys Thr His Arg
225                 230                 235                 240
Asp Lys Glu Glu Ile Val Phe Arg Thr Leu Ser Tyr Phe Asp Gly Val
                245                 250                 255
Asn Phe Ala Ala Arg Ala Lys Ile Pro Ala Leu Phe Ser Val Gly Leu
            260                 265                 270
Met Asp Asn Ile Ser Pro Pro Ser Thr Val Phe Ala Ala Tyr Asn Tyr
        275                 280                 285
Tyr Ala Gly Pro Lys Glu Ile Arg Ile Tyr Pro Tyr Asn Asn His Glu
    290                 295                 300
Gly Gly Gly Ser Phe Gln Ala Val Glu Gln Val Lys Phe Leu Lys Lys
305                 310                 315                 320
Leu Phe Glu Lys Gly
                325

<210> SEQ ID NO 22
<211> LENGTH: 325
<212> TYPE: PRT
<213> ORGANISM: artificial sequence
<220> FEATURE:
<223> OTHER INFORMATION: synthetic construct

<400> SEQUENCE: 22

Met Ala Phe Phe Asp Leu Pro Leu Glu Glu Leu Lys Lys Tyr Arg Pro
1               5                   10                  15
Glu Arg Tyr Glu Glu Lys Asp Phe Asp Glu Phe Trp Glu Glu Thr Leu
            20                  25                  30
```

| | | | | | | | | | | | | |
|---|---|---|---|---|---|---|---|---|---|---|---|---|
| Ala | Glu | Ser | Glu | Lys | Phe | Pro | Leu | Asp | Pro | Val | Phe | Glu | Arg | Met | Glu |
| | | 35 | | | | 40 | | | | 45 | | | | | |
| Ser | His | Leu | Lys | Thr | Val | Glu | Ala | Tyr | Asp | Val | Thr | Phe | Ser | Gly | Tyr |
| | 50 | | | | 55 | | | | 60 | | | | | | |
| Arg | Gly | Gln | Arg | Ile | Lys | Gly | Trp | Leu | Leu | Val | Pro | Lys | Leu | Glu | Glu |
| 65 | | | | 70 | | | | 75 | | | | 80 | | | |
| Glu | Lys | Leu | Pro | Cys | Val | Val | Gln | Tyr | Ile | Gly | Tyr | Asn | Gly | Gly | Arg |
| | | | 85 | | | | 90 | | | | 95 | | | | |
| Gly | Phe | Pro | His | Asp | Trp | Leu | Phe | Trp | Pro | Ser | Met | Gly | Phe | Ile | Cys |
| | | 100 | | | | 105 | | | | 110 | | | | | |
| Phe | Val | Met | Asp | Thr | Arg | Gly | Gln | Gly | Ser | Gly | Trp | Leu | Lys | Gly | Asp |
| | 115 | | | | 120 | | | | 125 | | | | | | |
| Thr | Pro | Asp | Tyr | Pro | Glu | Gly | Pro | Val | Asp | Pro | Gln | Tyr | Pro | Gly | Phe |
| | 130 | | | | 135 | | | | 140 | | | | | | |
| Met | Thr | Arg | Gly | Ile | Leu | Asp | Pro | Arg | Thr | Tyr | Tyr | Arg | Arg | Val |
| 145 | | | | 150 | | | | 155 | | | | 160 | | | |
| Phe | Thr | Asp | Ala | Val | Arg | Ala | Val | Glu | Ala | Ala | Ser | Phe | Pro | Gln |
| | | | 165 | | | | 170 | | | | 175 | | | | |
| Val | Asp | Gln | Glu | Arg | Ile | Val | Ile | Ala | Gly | Ser | Gly | Gly | Gly |
| | | 180 | | | | 185 | | | | 190 | | | | | |
| Ile | Ala | Leu | Ala | Val | Ser | Ala | Leu | Ser | Lys | Lys | Ala | Lys | Ala | Leu | Leu |
| | | 195 | | | | 200 | | | | 205 | | | | | |
| Cys | Asp | Val | Pro | Phe | Leu | Cys | His | Phe | Arg | Arg | Ala | Val | Gln | Leu | Val |
| 210 | | | | 215 | | | | 220 | | | | | | | |
| Asp | Thr | His | Pro | Tyr | Ala | Glu | Ile | Thr | Asn | Phe | Leu | Lys | Thr | His | Arg |
| 225 | | | | 230 | | | | 235 | | | | 240 | | | |
| Asp | Lys | Glu | Glu | Ile | Val | Phe | Arg | Thr | Leu | Ser | Tyr | Phe | Asp | Gly | Val |
| | | | 245 | | | | 250 | | | | 255 | | | | |
| Asn | Phe | Ala | Ala | Arg | Ala | Lys | Ile | Pro | Ala | Leu | Phe | Ser | Val | Gly | Leu |
| | | 260 | | | | 265 | | | | 270 | | | | | |
| Met | Asp | Asn | Ile | Ser | Pro | Pro | Ser | Thr | Val | Phe | Ala | Ala | Tyr | Asn | Tyr |
| | 275 | | | | 280 | | | | 285 | | | | | | |
| Tyr | Ala | Gly | Pro | Lys | Glu | Ile | Arg | Ile | Tyr | Pro | Tyr | Asn | Asn | His | Glu |
| | 290 | | | | 295 | | | | 300 | | | | | | |
| Gly | Gly | Gly | Ser | Phe | Gln | Ala | Val | Glu | Gln | Val | Lys | Phe | Leu | Lys | Lys |
| 305 | | | | 310 | | | | 315 | | | | 320 | | | |
| Leu | Phe | Glu | Lys | Gly |
| | | | | 325 |

```
<210> SEQ ID NO 23
<211> LENGTH: 981
<212> TYPE: DNA
<213> ORGANISM: Thermotoga lettingae

<400> SEQUENCE: 23
atggtttact tcgatatgcc actggaagat ctgcgcaaat acctgccgca gcgctacgaa      60
gaaaaagact ttgacgattt ctggaaacag acgattcacg aaacccgtgg ttacttccag     120
gagccgatcc tgaagaaagt tgatttctac ctgcaaaacg ttgaaacgtt cgatgtgacc     180
ttctctggtt accgtggtca gaagatcaaa ggctggctga tcctgcctaa atttcgtaac     240
ggcaaactgc catgcgttgt tgagttcgta ggttacggtg cggccgtgg tttcccgtat      300 gattggctgc tgtggtccgc tgccggctac gctcacttca tcatggatac ccgcggtcag     360
ggttctaact ggatgaaagg cgacacgcca gactatgagg acaaccccgag cgatccgcag     420 tacccgggtt ttctgaccaa aggcgtgctg aacccggaaa cctactatta tcgtcgcgtt     480
```

-continued

```
ttcatggatg ctttcatggc ggttgaaact atctctcagc tggagcagat tgactcccag    540
accatcatcc tgtccggtgc aagccagggt ggcggtatcg ctctggccgt tagcgccctg    600
tctagcaaag tgatggccct gctgtgcgat gtaccgttcc tgtgccatta taaacgcgca    660
gtacagatta ctgattctat gccgtatgca gaaatcaccc gttactgcaa aacgcacatc    720
gacaaaattc agaccgtttt tcgcaccctg tcttactttg atggcgtaaa cttcgcagcc    780
cgcgctaagt gcccggcact gttctccgtt ggcctgatgg atgatatttg cccgccgtct    840
acggtattcg ccgcatacaa ctactatgca ggcgagaaag atattcgtat ttacccgtat    900
aacaaccatg aaggcggtgg ctctttccac actctggaga aactgaagtt cgttaagaaa    960
accatttcta tgcgcgaata a                                              981
```

```
<210> SEQ ID NO 24
<211> LENGTH: 326
<212> TYPE: PRT
<213> ORGANISM: Thermotoga lettingae

<400> SEQUENCE: 24
```

Met Val Tyr Phe Asp Met Pro Leu Glu Asp Leu Arg Lys Tyr Leu Pro
1               5                   10                  15

Gln Arg Tyr Glu Glu Lys Asp Phe Asp Asp Phe Trp Lys Gln Thr Ile
            20                  25                  30

His Glu Thr Arg Gly Tyr Phe Gln Glu Pro Ile Leu Lys Lys Val Asp
        35                  40                  45

Phe Tyr Leu Gln Asn Val Glu Thr Phe Asp Val Thr Phe Ser Gly Tyr
    50                  55                  60

Arg Gly Gln Lys Ile Lys Gly Trp Leu Ile Leu Pro Lys Phe Arg Asn
65                  70                  75                  80

Gly Lys Leu Pro Cys Val Val Glu Phe Val Gly Tyr Gly Gly Gly Arg
                85                  90                  95

Gly Phe Pro Tyr Asp Trp Leu Leu Trp Ser Ala Ala Gly Tyr Ala His
            100                 105                 110

Phe Ile Met Asp Thr Arg Gly Gln Gly Ser Asn Trp Met Lys Gly Asp
        115                 120                 125

Thr Pro Asp Tyr Glu Asp Asn Pro Ser Asp Pro Gln Tyr Pro Gly Phe
    130                 135                 140

Leu Thr Lys Gly Val Leu Asn Pro Glu Thr Tyr Tyr Arg Arg Val
145                 150                 155                 160

Phe Met Asp Ala Phe Met Ala Val Glu Thr Ile Ser Gln Leu Glu Gln
                165                 170                 175

Ile Asp Ser Gln Thr Ile Ile Leu Ser Gly Ala Ser Gln Gly Gly Gly
            180                 185                 190

Ile Ala Leu Ala Val Ser Ala Leu Ser Ser Lys Val Met Ala Leu Leu
        195                 200                 205

Cys Asp Val Pro Phe Leu Cys His Tyr Lys Arg Ala Val Gln Ile Thr
    210                 215                 220

Asp Ser Met Pro Tyr Ala Glu Ile Thr Arg Tyr Cys Lys Thr His Ile
225                 230                 235                 240

Asp Lys Ile Gln Thr Val Phe Arg Thr Leu Ser Tyr Phe Asp Gly Val
                245                 250                 255

Asn Phe Ala Ala Arg Ala Lys Cys Pro Ala Leu Phe Ser Val Gly Leu
            260                 265                 270

Met Asp Asp Ile Cys Pro Pro Ser Thr Val Phe Ala Ala Tyr Asn Tyr
        275                 280                 285

Tyr Ala Gly Glu Lys Asp Ile Arg Ile Tyr Pro Tyr Asn Asn His Glu
    290                 295                 300

Gly Gly Gly Ser Phe His Thr Leu Glu Lys Leu Lys Phe Val Lys Lys
305                 310                 315                 320

Thr Ile Ser Met Arg Glu
                325

<210> SEQ ID NO 25
<211> LENGTH: 326
<212> TYPE: PRT
<213> ORGANISM: artificial sequence
<220> FEATURE:
<223> OTHER INFORMATION: synthetic construct

<400> SEQUENCE: 25

Met Val Tyr Phe Asp Met Pro Leu Glu Asp Leu Arg Lys Tyr Leu Pro
1               5                   10                  15

Gln Arg Tyr Glu Glu Lys Asp Phe Asp Asp Phe Trp Lys Gln Thr Ile
            20                  25                  30

His Glu Thr Arg Gly Tyr Phe Gln Glu Pro Ile Leu Lys Lys Val Asp
        35                  40                  45

Phe Tyr Leu Gln Asn Val Glu Thr Phe Asp Val Thr Phe Ser Gly Tyr
50                  55                  60

Arg Gly Gln Lys Ile Lys Gly Trp Leu Ile Leu Pro Lys Phe Arg Asn
65                  70                  75                  80

Gly Lys Leu Pro Cys Val Val Glu Phe Val Gly Tyr Gly Gly Arg
            85                  90                  95

Gly Phe Pro Tyr Asp Trp Leu Leu Trp Ser Ala Ala Gly Tyr Ala His
            100                 105                 110

Phe Ile Met Asp Thr Arg Gly Gln Gly Ser Asn Trp Met Lys Gly Asp
        115                 120                 125

Thr Pro Asp Tyr Glu Asp Asn Pro Ser Asp Pro Gln Tyr Pro Gly Phe
    130                 135                 140

Leu Thr Lys Gly Val Leu Asn Pro Glu Thr Tyr Tyr Tyr Arg Arg Val
145                 150                 155                 160

Phe Met Asp Ala Phe Met Ala Val Glu Thr Ile Ser Gln Leu Glu Gln
                165                 170                 175

Ile Asp Ser Gln Thr Ile Ile Leu Ser Gly Ala Ser Gln Gly Gly Gly
            180                 185                 190

Ile Ala Leu Ala Val Ser Ala Leu Ser Ser Lys Val Met Ala Leu Leu
        195                 200                 205

Cys Asp Val Pro Phe Leu Cys His Tyr Lys Arg Ala Val Gln Ile Thr
210                 215                 220

Asp Ser Met Pro Tyr Ala Glu Ile Thr Arg Tyr Cys Lys Thr His Ile
225                 230                 235                 240

Asp Lys Ile Gln Thr Val Phe Arg Thr Leu Ser Tyr Phe Asp Gly Val
                245                 250                 255

Asn Phe Ala Ala Arg Ala Lys Cys Pro Ala Leu Phe Ser Val Gly Leu
            260                 265                 270

Met Asp Asp Ile Ala Pro Pro Ser Thr Val Phe Ala Ala Tyr Asn Tyr
        275                 280                 285

Tyr Ala Gly Glu Lys Asp Ile Arg Ile Tyr Pro Tyr Asn Asn His Glu
    290                 295                 300

Gly Gly Gly Ser Phe His Thr Leu Glu Lys Leu Lys Phe Val Lys Lys
305                 310                 315                 320

Thr Ile Ser Met Arg Glu
            325

<210> SEQ ID NO 26
<211> LENGTH: 326
<212> TYPE: PRT
<213> ORGANISM: artificial sequence
<220> FEATURE:
<223> OTHER INFORMATION: synthetic construct

<400> SEQUENCE: 26

Met Val Tyr Phe Asp Met Pro Leu Glu Asp Leu Arg Lys Tyr Leu Pro
1               5                   10                  15

Gln Arg Tyr Glu Glu Lys Asp Phe Asp Asp Phe Trp Lys Gln Thr Ile
            20                  25                  30

His Glu Thr Arg Gly Tyr Phe Gln Glu Pro Ile Leu Lys Lys Val Asp
        35                  40                  45

Phe Tyr Leu Gln Asn Val Glu Thr Phe Asp Val Thr Phe Ser Gly Tyr
    50                  55                  60

Arg Gly Gln Lys Ile Lys Gly Trp Leu Ile Leu Pro Lys Phe Arg Asn
65                  70                  75                  80

Gly Lys Leu Pro Cys Val Val Glu Phe Val Gly Tyr Gly Gly Gly Arg
                85                  90                  95

Gly Phe Pro Tyr Asp Trp Leu Leu Trp Ser Ala Ala Gly Tyr Ala His
            100                 105                 110

Phe Ile Met Asp Thr Arg Gly Gln Gly Ser Asn Trp Met Lys Gly Asp
        115                 120                 125

Thr Pro Asp Tyr Glu Asp Asn Pro Ser Asp Pro Gln Tyr Pro Gly Phe
    130                 135                 140

Leu Thr Lys Gly Val Leu Asn Pro Glu Thr Tyr Tyr Tyr Arg Arg Val
145                 150                 155                 160

Phe Met Asp Ala Phe Met Ala Val Glu Thr Ile Ser Gln Leu Glu Gln
                165                 170                 175

Ile Asp Ser Gln Thr Ile Ile Leu Ser Gly Ala Ser Gln Gly Gly Gly
            180                 185                 190

Ile Ala Leu Ala Val Ser Ala Leu Ser Ser Lys Val Met Ala Leu Leu
        195                 200                 205

Cys Asp Val Pro Phe Leu Cys His Tyr Lys Arg Ala Val Gln Ile Thr
210                 215                 220

Asp Ser Met Pro Tyr Ala Glu Ile Thr Arg Tyr Cys Lys Thr His Ile
225                 230                 235                 240

Asp Lys Ile Gln Thr Val Phe Arg Thr Leu Ser Tyr Phe Asp Gly Val
                245                 250                 255

Asn Phe Ala Ala Arg Ala Lys Cys Pro Ala Leu Phe Ser Val Gly Leu
            260                 265                 270

Met Asp Asp Ile Val Pro Pro Ser Thr Val Phe Ala Ala Tyr Asn Tyr
        275                 280                 285

Tyr Ala Gly Glu Lys Asp Ile Arg Ile Tyr Pro Tyr Asn Asn His Glu
    290                 295                 300

Gly Gly Gly Ser Phe His Thr Leu Glu Lys Leu Lys Phe Val Lys Lys
305                 310                 315                 320

Thr Ile Ser Met Arg Glu
            325

<210> SEQ ID NO 27
<211> LENGTH: 326
<212> TYPE: PRT

<213> ORGANISM: artificial sequence
<220> FEATURE:
<223> OTHER INFORMATION: synthetic construct

<400> SEQUENCE: 27

```
Met Val Tyr Phe Asp Met Pro Leu Glu Asp Leu Arg Lys Tyr Leu Pro
1               5                   10                  15

Gln Arg Tyr Glu Glu Lys Asp Phe Asp Phe Trp Lys Gln Thr Ile
            20                  25                  30

His Glu Thr Arg Gly Tyr Phe Gln Glu Pro Ile Leu Lys Lys Val Asp
                35                  40                  45

Phe Tyr Leu Gln Asn Val Glu Thr Phe Asp Val Thr Phe Ser Gly Tyr
    50                  55                  60

Arg Gly Gln Lys Ile Lys Gly Trp Leu Ile Leu Pro Lys Phe Arg Asn
65                  70                  75                  80

Gly Lys Leu Pro Cys Val Val Glu Phe Val Gly Tyr Gly Gly Arg
                85                  90                  95

Gly Phe Pro Tyr Asp Trp Leu Leu Trp Ser Ala Ala Gly Tyr Ala His
            100                 105                 110

Phe Ile Met Asp Thr Arg Gly Gln Gly Ser Asn Trp Met Lys Gly Asp
        115                 120                 125

Thr Pro Asp Tyr Glu Asp Asn Pro Ser Asp Pro Gln Tyr Pro Gly Phe
    130                 135                 140

Leu Thr Lys Gly Val Leu Asn Pro Glu Thr Tyr Tyr Arg Arg Val
145                 150                 155                 160

Phe Met Asp Ala Phe Met Ala Val Glu Thr Ile Ser Gln Leu Glu Gln
                165                 170                 175

Ile Asp Ser Gln Thr Ile Ile Leu Ser Gly Ala Ser Gln Gly Gly Gly
            180                 185                 190

Ile Ala Leu Ala Val Ser Ala Leu Ser Ser Lys Val Met Ala Leu Leu
        195                 200                 205

Cys Asp Val Pro Phe Leu Cys His Tyr Lys Arg Ala Val Gln Ile Thr
    210                 215                 220

Asp Ser Met Pro Tyr Ala Glu Ile Thr Arg Tyr Cys Lys Thr His Ile
225                 230                 235                 240

Asp Lys Ile Gln Thr Val Phe Arg Thr Leu Ser Tyr Phe Asp Gly Val
                245                 250                 255

Asn Phe Ala Ala Arg Ala Lys Cys Pro Ala Leu Phe Ser Val Gly Leu
            260                 265                 270

Met Asp Asp Ile Ser Pro Pro Ser Thr Val Phe Ala Ala Tyr Asn Tyr
        275                 280                 285

Tyr Ala Gly Glu Lys Asp Ile Arg Ile Tyr Pro Tyr Asn Asn His Glu
    290                 295                 300

Gly Gly Gly Ser Phe His Thr Leu Glu Lys Leu Lys Phe Val Lys Lys
305                 310                 315                 320

Thr Ile Ser Met Arg Glu
            325
```

<210> SEQ ID NO 28
<211> LENGTH: 326
<212> TYPE: PRT
<213> ORGANISM: artificial sequence
<220> FEATURE:
<223> OTHER INFORMATION: synthetic construct

<400> SEQUENCE: 28

Met Val Tyr Phe Asp Met Pro Leu Glu Asp Leu Arg Lys Tyr Leu Pro

```
                   1               5                  10                 15
Gln Arg Tyr Glu Glu Lys Asp Phe Asp Asp Phe Trp Lys Gln Thr Ile
                        20                  25                  30

His Glu Thr Arg Gly Tyr Phe Gln Glu Pro Ile Leu Lys Lys Val Asp
                        35                  40                  45

Phe Tyr Leu Gln Asn Val Glu Thr Phe Asp Val Thr Phe Ser Gly Tyr
             50                  55                  60

Arg Gly Gln Lys Ile Lys Gly Trp Leu Ile Leu Pro Lys Phe Arg Asn
 65                  70                  75                  80

Gly Lys Leu Pro Cys Val Val Glu Phe Val Gly Tyr Gly Gly Arg
                        85                  90                  95

Gly Phe Pro Tyr Asp Trp Leu Leu Trp Ser Ala Ala Gly Tyr Ala His
                       100                 105                 110

Phe Ile Met Asp Thr Arg Gly Gln Gly Ser Asn Trp Met Lys Gly Asp
                       115                 120                 125

Thr Pro Asp Tyr Glu Asp Asn Pro Ser Asp Pro Gln Tyr Pro Gly Phe
            130                 135                 140

Leu Thr Lys Gly Val Leu Asn Pro Glu Thr Tyr Tyr Arg Arg Val
145                 150                 155                 160

Phe Met Asp Ala Phe Met Ala Val Glu Thr Ile Ser Gln Leu Glu Gln
                       165                 170                 175

Ile Asp Ser Gln Thr Ile Ile Leu Ser Gly Ala Ser Gln Gly Gly Gly
                       180                 185                 190

Ile Ala Leu Ala Val Ser Ala Leu Ser Ser Lys Val Met Ala Leu Leu
                       195                 200                 205

Cys Asp Val Pro Phe Leu Cys His Tyr Lys Arg Ala Val Gln Ile Thr
            210                 215                 220

Asp Ser Met Pro Tyr Ala Glu Ile Thr Arg Tyr Cys Lys Thr His Ile
225                 230                 235                 240

Asp Lys Ile Gln Thr Val Phe Arg Thr Leu Ser Tyr Phe Asp Gly Val
                       245                 250                 255

Asn Phe Ala Ala Arg Ala Lys Cys Pro Ala Leu Phe Ser Val Gly Leu
                       260                 265                 270

Met Asp Asp Ile Thr Pro Pro Ser Thr Val Phe Ala Ala Tyr Asn Tyr
            275                 280                 285

Tyr Ala Gly Glu Lys Asp Ile Arg Ile Tyr Pro Tyr Asn Asn His Glu
            290                 295                 300

Gly Gly Gly Ser Phe His Thr Leu Glu Lys Leu Lys Phe Val Lys Lys
305                 310                 315                 320

Thr Ile Ser Met Arg Glu
                325

<210> SEQ ID NO 29
<211> LENGTH: 978
<212> TYPE: DNA
<213> ORGANISM: Thermotoga petrophila

<400> SEQUENCE: 29
atggcattct tcgacctgcc gctggaggaa ctgaaaaagt atcgcccgga gcgttacgaa      60
gaaaaggatt tcgatgagtt ctgggaaggc accctggccg agaacgaaaa attccctctg     120
gatccggtct tcgaacgtat ggaaagccat ctgaaaaccg tagaggctta cgacgtgacc     180
ttcagcggtt acatgggcca gcgtatcaaa ggctggctgc tggtcccgaa actggaggag     240
gagaaactgc cgtgcgttgt tcagtacatc ggctacaacg gcggtcgcgg tttcccgcac     300
```

-continued

```
gattggctgt tctggccgtc tatgggttac atctgctttg ttatggacac ccgtggccag    360
ggtagcggtt ggatgaaggg tgacaccccg gactatccgg aggacccggt agacccgcag    420
tacccaggct ttatgacccg cggcattctg gacccgcgca cttactacta ccgtcgcgtt    480
tttaccgatg ctgttcgcgc agtggaggca gccgcgtcct ttccacgcgt agaccacgaa    540
cgtatcgtaa tcgcaggcgg ctcccagggt ggcggcatcg cgctggcggt tccgcactg     600 agcaaaaagg ccaaagcgct gctgtgcgat gtgccgttcc tgtgtcactt ccgtcgtgcg    660
gttcagctgg tagataccca cccgtacgct gagatcacca actttctgaa gacgcatcgt    720
gataaagagg aaatcgtatt tcgtacgctg tcctatttcg atggtgtgaa ctttgcggta    780
cgtgcaaaga tcccggcccct gttctctgtt ggtctgatgg acaacatttg cccgccgagc    840
actgtctttg cagcgtacaa ccactatgcg ggcccaaaag aaattcgcat ctacccatac    900
aacaaccacg aaggcggcgg ttccttccag gcaatcgaac aggtcaaatt cctgaaacgt    960
ctgttcgaga aaggttaa                                                  978
```

<210> SEQ ID NO 30
<211> LENGTH: 325
<212> TYPE: PRT
<213> ORGANISM: Thermotoga petrophila

<400> SEQUENCE: 30

```
Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Gly Thr Leu
            20                  25                  30

Ala Glu Asn Glu Lys Phe Pro Leu Asp Pro Val Phe Glu Arg Met Glu
        35                  40                  45

Ser His Leu Lys Thr Val Glu Ala Tyr Asp Val Thr Phe Ser Gly Tyr
    50                  55                  60

Met Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Met Lys Gly Asp
        115                 120                 125

Thr Pro Asp Tyr Pro Glu Asp Pro Val Asp Pro Gln Tyr Pro Gly Phe
    130                 135                 140

Met Thr Arg Gly Ile Leu Asp Pro Arg Thr Tyr Tyr Tyr Arg Arg Val
145                 150                 155                 160

Phe Thr Asp Ala Val Arg Ala Val Glu Ala Ala Ser Phe Pro Arg
                165                 170                 175

Val Asp His Glu Arg Ile Val Ile Ala Gly Gly Ser Gln Gly Gly Gly
            180                 185                 190

Ile Ala Leu Ala Val Ser Ala Leu Ser Lys Lys Ala Lys Ala Leu Leu
        195                 200                 205

Cys Asp Val Pro Phe Leu Cys His Phe Arg Arg Ala Val Gln Leu Val
    210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255
```

```
Asn Phe Ala Val Arg Ala Lys Ile Pro Ala Leu Phe Ser Val Gly Leu
            260                 265                 270

Met Asp Asn Ile Cys Pro Pro Ser Thr Val Phe Ala Ala Tyr Asn His
            275                 280                 285

Tyr Ala Gly Pro Lys Glu Ile Arg Ile Tyr Pro Tyr Asn Asn His Glu
            290                 295                 300

Gly Gly Gly Ser Phe Gln Ala Ile Glu Gln Val Lys Phe Leu Lys Arg
305                 310                 315                 320

Leu Phe Glu Lys Gly
            325

<210> SEQ ID NO 31
<211> LENGTH: 325
<212> TYPE: PRT
<213> ORGANISM: artificial sequence
<220> FEATURE:
<223> OTHER INFORMATION: synthetic construct

<400> SEQUENCE: 31

Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Gly Thr Leu
            20                  25                  30

Ala Glu Asn Glu Lys Phe Pro Leu Asp Pro Val Phe Glu Arg Met Glu
            35                  40                  45

Ser His Leu Lys Thr Val Glu Ala Tyr Asp Val Thr Phe Ser Gly Tyr
        50                  55                  60

Met Gly Gln Arg Ile Lys Gly Trp Leu Leu Val Pro Lys Leu Glu Glu
65              70                  75                  80

Glu Lys Leu Pro Cys Val Val Gln Tyr Ile Gly Tyr Asn Gly Gly Arg
            85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Met Lys Gly Asp
            115                 120                 125

Thr Pro Asp Tyr Pro Glu Asp Pro Val Asp Pro Gln Tyr Pro Gly Phe
130                 135                 140

Met Thr Arg Gly Ile Leu Asp Pro Arg Thr Tyr Tyr Tyr Arg Arg Val
145                 150                 155                 160

Phe Thr Asp Ala Val Arg Ala Val Glu Ala Ala Ala Ser Phe Pro Arg
            165                 170                 175

Val Asp His Glu Arg Ile Val Ile Ala Gly Gly Ser Gln Gly Gly Gly
            180                 185                 190

Ile Ala Leu Ala Val Ser Ala Leu Ser Lys Lys Ala Lys Ala Leu Leu
            195                 200                 205

Cys Asp Val Pro Phe Leu Cys His Phe Arg Arg Ala Val Gln Leu Val
            210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
            245                 250                 255

Asn Phe Ala Val Arg Ala Lys Ile Pro Ala Leu Phe Ser Val Gly Leu
            260                 265                 270

Met Asp Asn Ile Ala Pro Pro Ser Thr Val Phe Ala Ala Tyr Asn His
            275                 280                 285

Tyr Ala Gly Pro Lys Glu Ile Arg Ile Tyr Pro Tyr Asn Asn His Glu
```

```
                    290                 295                 300
Gly Gly Gly Ser Phe Gln Ala Ile Glu Gln Val Lys Phe Leu Lys Arg
305                 310                 315                 320

Leu Phe Glu Lys Gly
                325

<210> SEQ ID NO 32
<211> LENGTH: 325
<212> TYPE: PRT
<213> ORGANISM: artificial sequence
<220> FEATURE:
<223> OTHER INFORMATION: synthetic construct

<400> SEQUENCE: 32

Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Gly Thr Leu
                20                  25                  30

Ala Glu Asn Glu Lys Phe Pro Leu Asp Pro Val Phe Glu Arg Met Glu
                35                  40                  45

Ser His Leu Lys Thr Val Glu Ala Tyr Asp Val Thr Phe Ser Gly Tyr
            50                  55                  60

Met Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
                100                 105                 110

Phe Val Met Asp Thr Arg Gly Gln Gly Ser Gly Trp Met Lys Gly Asp
                115                 120                 125

Thr Pro Asp Tyr Pro Glu Asp Pro Val Asp Pro Gln Tyr Pro Gly Phe
            130                 135                 140

Met Thr Arg Gly Ile Leu Asp Pro Arg Thr Tyr Tyr Tyr Arg Arg Val
145                 150                 155                 160

Phe Thr Asp Ala Val Arg Ala Val Glu Ala Ala Ser Phe Pro Arg
                165                 170                 175

Val Asp His Glu Arg Ile Val Ile Ala Gly Gly Ser Gln Gly Gly Gly
                180                 185                 190

Ile Ala Leu Ala Val Ser Ala Leu Ser Lys Lys Ala Lys Ala Leu Leu
            195                 200                 205

Cys Asp Val Pro Phe Leu Cys His Phe Arg Arg Ala Val Gln Leu Val
                210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Val Arg Ala Lys Ile Pro Ala Leu Phe Ser Val Gly Leu
                260                 265                 270

Met Asp Asn Ile Val Pro Pro Ser Thr Val Phe Ala Ala Tyr Asn His
                275                 280                 285

Tyr Ala Gly Pro Lys Glu Ile Arg Ile Tyr Pro Tyr Asn Asn His Glu
                290                 295                 300

Gly Gly Gly Ser Phe Gln Ala Ile Glu Gln Val Lys Phe Leu Lys Arg
305                 310                 315                 320

Leu Phe Glu Lys Gly
                325
```

<210> SEQ ID NO 33
<211> LENGTH: 325
<212> TYPE: PRT
<213> ORGANISM: artificial sequence
<220> FEATURE:
<223> OTHER INFORMATION: synthetic construct

<400> SEQUENCE: 33

```
Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Gly Thr Leu
            20                  25                  30

Ala Glu Asn Glu Lys Phe Pro Leu Asp Pro Val Phe Glu Arg Met Glu
        35                  40                  45

Ser His Leu Lys Thr Val Glu Ala Tyr Asp Val Thr Phe Ser Gly Tyr
    50                  55                  60

Met Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Met Lys Gly Asp
        115                 120                 125

Thr Pro Asp Tyr Pro Glu Asp Pro Val Asp Pro Gln Tyr Pro Gly Phe
    130                 135                 140

Met Thr Arg Gly Ile Leu Asp Pro Arg Thr Tyr Tyr Tyr Arg Arg Val
145                 150                 155                 160

Phe Thr Asp Ala Val Arg Ala Val Glu Ala Ala Ser Phe Pro Arg
                165                 170                 175

Val Asp His Glu Arg Ile Val Ile Ala Gly Gly Ser Gln Gly Gly Gly
            180                 185                 190

Ile Ala Leu Ala Val Ser Ala Leu Ser Lys Lys Ala Lys Ala Leu Leu
        195                 200                 205

Cys Asp Val Pro Phe Leu Cys His Phe Arg Arg Ala Val Gln Leu Val
    210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Val Arg Ala Lys Ile Pro Ala Leu Phe Ser Val Gly Leu
            260                 265                 270

Met Asp Asn Ile Ser Pro Pro Ser Thr Val Phe Ala Ala Tyr Asn His
        275                 280                 285

Tyr Ala Gly Pro Lys Glu Ile Arg Ile Tyr Pro Tyr Asn Asn His Glu
    290                 295                 300

Gly Gly Gly Ser Phe Gln Ala Ile Glu Gln Val Lys Phe Leu Lys Arg
305                 310                 315                 320

Leu Phe Glu Lys Gly
                325
```

<210> SEQ ID NO 34
<211> LENGTH: 325
<212> TYPE: PRT
<213> ORGANISM: artificial sequence
<220> FEATURE:

<223> OTHER INFORMATION: synthetic construct

<400> SEQUENCE: 34

| | | | | | | | | | | | | | | | |
|---|---|---|---|---|---|---|---|---|---|---|---|---|---|---|---|
| Met | Ala | Phe | Phe | Asp | Leu | Pro | Leu | Glu | Glu | Leu | Lys | Lys | Tyr | Arg | Pro |
| 1 | | | | 5 | | | | | 10 | | | | | 15 | |
| Glu | Arg | Tyr | Glu | Glu | Lys | Asp | Phe | Asp | Glu | Phe | Trp | Glu | Gly | Thr | Leu |
| | | | 20 | | | | | 25 | | | | | 30 | | |
| Ala | Glu | Asn | Glu | Lys | Phe | Pro | Leu | Asp | Pro | Val | Phe | Glu | Arg | Met | Glu |
| | | | | 35 | | | | | 40 | | | | | 45 | |
| Ser | His | Leu | Lys | Thr | Val | Glu | Ala | Tyr | Asp | Val | Thr | Phe | Ser | Gly | Tyr |
| | | 50 | | | | | 55 | | | | | 60 | | | |
| Met | Gly | Gln | Arg | Ile | Lys | Gly | Trp | Leu | Leu | Val | Pro | Lys | Leu | Glu | Glu |
| 65 | | | | | 70 | | | | | 75 | | | | | 80 |
| Glu | Lys | Leu | Pro | Cys | Val | Val | Gln | Tyr | Ile | Gly | Tyr | Asn | Gly | Gly | Arg |
| | | | | 85 | | | | | 90 | | | | | 95 | |
| Gly | Phe | Pro | His | Asp | Trp | Leu | Phe | Trp | Pro | Ser | Met | Gly | Tyr | Ile | Cys |
| | | | 100 | | | | | 105 | | | | | 110 | | |
| Phe | Val | Met | Asp | Thr | Arg | Gly | Gln | Gly | Ser | Gly | Trp | Met | Lys | Gly | Asp |
| | | 115 | | | | | 120 | | | | | 125 | | | |
| Thr | Pro | Asp | Tyr | Pro | Glu | Asp | Pro | Val | Asp | Pro | Gln | Tyr | Pro | Gly | Phe |
| 130 | | | | | 135 | | | | | 140 | | | | | |
| Met | Thr | Arg | Gly | Ile | Leu | Asp | Pro | Arg | Thr | Tyr | Tyr | Arg | Arg | Val |
| 145 | | | | | 150 | | | | | 155 | | | | | 160 |
| Phe | Thr | Asp | Ala | Val | Arg | Ala | Val | Glu | Ala | Ala | Ser | Phe | Pro | Arg |
| | | | | 165 | | | | | 170 | | | | | 175 | |
| Val | Asp | His | Glu | Arg | Ile | Val | Ile | Ala | Gly | Ser | Gln | Gly | Gly | Gly |
| | | | 180 | | | | | 185 | | | | | 190 | | |
| Ile | Ala | Leu | Ala | Val | Ser | Ala | Leu | Ser | Lys | Ala | Lys | Ala | Leu | Leu |
| | | 195 | | | | | 200 | | | | | 205 | | | |
| Cys | Asp | Val | Pro | Phe | Leu | Cys | His | Phe | Arg | Arg | Ala | Val | Gln | Leu | Val |
| 210 | | | | | 215 | | | | | 220 | | | | | |
| Asp | Thr | His | Pro | Tyr | Ala | Glu | Ile | Thr | Asn | Phe | Leu | Lys | Thr | His | Arg |
| 225 | | | | | 230 | | | | | 235 | | | | | 240 |
| Asp | Lys | Glu | Glu | Ile | Val | Phe | Arg | Thr | Leu | Ser | Tyr | Phe | Asp | Gly | Val |
| | | | | 245 | | | | | 250 | | | | | 255 | |
| Asn | Phe | Ala | Val | Arg | Ala | Lys | Ile | Pro | Ala | Leu | Phe | Ser | Val | Gly | Leu |
| | | | 260 | | | | | 265 | | | | | 270 | | |
| Met | Asp | Asn | Ile | Thr | Pro | Pro | Ser | Thr | Val | Phe | Ala | Ala | Tyr | Asn | His |
| | | 275 | | | | | 280 | | | | | 285 | | | |
| Tyr | Ala | Gly | Pro | Lys | Glu | Ile | Arg | Ile | Tyr | Pro | Tyr | Asn | Asn | His | Glu |
| | 290 | | | | | 295 | | | | | 300 | | | | |
| Gly | Gly | Gly | Ser | Phe | Gln | Ala | Ile | Glu | Gln | Val | Lys | Phe | Leu | Lys | Arg |
| 305 | | | | | 310 | | | | | 315 | | | | | 320 |
| Leu | Phe | Glu | Lys | Gly |
| | | | | 325 |

<210> SEQ ID NO 35
<211> LENGTH: 978
<212> TYPE: DNA
<213> ORGANISM: Thermotoga sp.

<400> SEQUENCE: 35
atggcctttt tcgatttacc actcgaagaa ctgaagaaat accgtccgga gcggtacgaa    60
gagaaagact cgatgagtt ctggaaagaa acactcgcag agagcgaaaa gtttcccctg   120
gaccccgtct tcgagaggat ggagtctcac ctcaaaacgg tcgaagtgta cgatgtcacc   180

```
ttctccggat acagaggaca gaggatcaag gggtggctcc ttgttccaaa attggaagaa      240
gaaaaacttc cctgcgttgt gcagtacata ggatacaacg gtggaagagg attccctcac      300
gactggctgt tctggccttc tatgggttac atatgtttcg tcatggatac tcgaggacag      360
ggaagcggct ggctgaaagg agatacaccg gattaccctg aggatcccgt tgaccctcag      420
tatccaggat tcatgacaag aggaatactg gatcccagaa cttactacta cagacgagtc      480
ttcacggacg ctgtcagagc cgttgaagcc gctgcttctt tccctcgggt agatcacgaa      540
agaatcgtga tagctggagg cagtcagggt ggcggaatag cccttgcggt gagcgctctc      600
tcaaagaaag caaaggctct tctgtgcgat gtgccgtttc tgtgtcactt cagaagggca      660
gtgcagcttg tggatacgca tccatacgcg gagatcacga actttctaaa gactcacagg      720
gacaaggaag aaatcgtgtt caggactctt tcctatttcg atggagtgaa cttcgcagtc      780
agagcgaaga tccctgcgct gttttctgtg ggtctcatgg acaacatttg tcctccttca      840
acggtttttg ctgcctacaa tcactacgct gggccgaagg aaatcagaat ctatccgtac      900
aacaaccacg agggaggagg ctctttccag gcaattgaac aggtgaaatt cttgaagaga      960
ctatttgaga aaggctag                                                   978
```

<210> SEQ ID NO 36
<211> LENGTH: 325
<212> TYPE: PRT
<213> ORGANISM: Thermotoga sp.

<400> SEQUENCE: 36

Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Lys Glu Thr Leu
            20                  25                  30

Ala Glu Ser Glu Lys Phe Pro Leu Asp Pro Val Phe Glu Arg Met Glu
        35                  40                  45

Ser His Leu Lys Thr Val Glu Val Tyr Asp Val Thr Phe Ser Gly Tyr
    50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
        115                 120                 125

Thr Pro Asp Tyr Pro Glu Asp Pro Val Asp Pro Gln Tyr Pro Gly Phe
    130                 135                 140

Met Thr Arg Gly Ile Leu Asp Pro Arg Thr Tyr Tyr Tyr Arg Arg Val
145                 150                 155                 160

Phe Thr Asp Ala Val Arg Ala Val Glu Ala Ala Ala Ser Phe Pro Arg
                165                 170                 175

Val Asp His Glu Arg Ile Val Ile Ala Gly Gly Ser Gln Gly Gly Gly
            180                 185                 190

Ile Ala Leu Ala Val Ser Ala Leu Ser Lys Ala Lys Ala Leu Leu
        195                 200                 205

Cys Asp Val Pro Phe Leu Cys His Phe Arg Arg Ala Val Gln Leu Val
    210                 215                 220

Asp Thr His Pro Tyr Ala Glu Ile Thr Asn Phe Leu Lys Thr His Arg

```
                    225                 230                 235                 240
Asp Lys Glu Glu Ile Val Phe Arg Thr Leu Ser Tyr Phe Asp Gly Val
                245                 250                 255

Asn Phe Ala Val Arg Ala Lys Ile Pro Ala Leu Phe Ser Val Gly Leu
            260                 265                 270

Met Asp Asn Ile Cys Pro Pro Ser Thr Val Phe Ala Ala Tyr Asn His
        275                 280                 285

Tyr Ala Gly Pro Lys Glu Ile Arg Ile Tyr Pro Tyr Asn Asn His Glu
    290                 295                 300

Gly Gly Gly Ser Phe Gln Ala Ile Glu Gln Val Lys Phe Leu Lys Arg
305                 310                 315                 320

Leu Phe Glu Lys Gly
                325

<210> SEQ ID NO 37
<211> LENGTH: 325
<212> TYPE: PRT
<213> ORGANISM: artificial sequence
<220> FEATURE:
<223> OTHER INFORMATION: synthetic construct

<400> SEQUENCE: 37

Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Lys Glu Thr Leu
            20                  25                  30

Ala Glu Ser Glu Lys Phe Pro Leu Asp Pro Val Phe Glu Arg Met Glu
        35                  40                  45

Ser His Leu Lys Thr Val Glu Val Tyr Asp Val Thr Phe Ser Gly Tyr
    50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
        115                 120                 125

Thr Pro Asp Tyr Pro Glu Asp Pro Val Asp Pro Gln Tyr Pro Gly Phe
    130                 135                 140

Met Thr Arg Gly Ile Leu Asp Pro Arg Thr Tyr Tyr Tyr Arg Arg Val
145                 150                 155                 160

Phe Thr Asp Ala Val Arg Ala Val Glu Ala Ala Ser Phe Pro Arg
                165                 170                 175

Val Asp His Glu Arg Ile Val Ile Ala Gly Gly Ser Gln Gly Gly Gly
            180                 185                 190

Ile Ala Leu Ala Val Ser Ala Leu Ser Lys Lys Ala Lys Ala Leu Leu
        195                 200                 205

Cys Asp Val Pro Phe Leu Cys His Phe Arg Arg Ala Val Gln Leu Val
    210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Val Arg Ala Lys Ile Pro Ala Leu Phe Ser Val Gly Leu
            260                 265                 270
```

```
Met Asp Asn Ile Ala Pro Pro Ser Thr Val Phe Ala Ala Tyr Asn His
        275                 280                 285

Tyr Ala Gly Pro Lys Glu Ile Arg Ile Tyr Pro Tyr Asn Asn His Glu
        290                 295                 300

Gly Gly Gly Ser Phe Gln Ala Ile Glu Gln Val Lys Phe Leu Lys Arg
305                 310                 315                 320

Leu Phe Glu Lys Gly
            325

<210> SEQ ID NO 38
<211> LENGTH: 325
<212> TYPE: PRT
<213> ORGANISM: artificial sequence
<220> FEATURE:
<223> OTHER INFORMATION: synthetic construct

<400> SEQUENCE: 38

Met Ala Phe Phe Asp Leu Pro Leu Glu Glu Lys Lys Tyr Arg Pro
1               5                   10                  15

Glu Arg Tyr Glu Glu Lys Asp Phe Asp Glu Phe Trp Lys Glu Thr Leu
            20                  25                  30

Ala Glu Ser Glu Lys Phe Pro Leu Asp Pro Val Phe Glu Arg Met Glu
        35                  40                  45

Ser His Leu Lys Thr Val Glu Val Tyr Asp Val Thr Phe Ser Gly Tyr
    50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
        115                 120                 125

Thr Pro Asp Tyr Pro Glu Asp Pro Val Asp Pro Gln Tyr Pro Gly Phe
    130                 135                 140

Met Thr Arg Gly Ile Leu Asp Pro Arg Thr Tyr Tyr Arg Arg Val
145                 150                 155                 160

Phe Thr Asp Ala Val Arg Ala Val Glu Ala Ala Ser Phe Pro Arg
                165                 170                 175

Val Asp His Glu Arg Ile Val Ile Ala Gly Gly Ser Gln Gly Gly Gly
            180                 185                 190

Ile Ala Leu Ala Val Ser Ala Leu Ser Lys Lys Ala Lys Ala Leu Leu
        195                 200                 205

Cys Asp Val Pro Phe Leu Cys His Phe Arg Arg Ala Val Gln Leu Val
210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Val Arg Ala Lys Ile Pro Ala Leu Phe Ser Val Gly Leu
            260                 265                 270

Met Asp Asn Ile Val Pro Pro Ser Thr Val Phe Ala Ala Tyr Asn His
        275                 280                 285

Tyr Ala Gly Pro Lys Glu Ile Arg Ile Tyr Pro Tyr Asn Asn His Glu
        290                 295                 300
```

Gly Gly Gly Ser Phe Gln Ala Ile Glu Gln Val Lys Phe Leu Lys Arg
305                 310                 315                 320

Leu Phe Glu Lys Gly
            325

<210> SEQ ID NO 39
<211> LENGTH: 325
<212> TYPE: PRT
<213> ORGANISM: artificial sequence
<220> FEATURE:
<223> OTHER INFORMATION: synthetic construct

<400> SEQUENCE: 39

Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Lys Glu Thr Leu
            20                  25                  30

Ala Glu Ser Glu Lys Phe Pro Leu Asp Pro Val Phe Glu Arg Met Glu
        35                  40                  45

Ser His Leu Lys Thr Val Glu Val Tyr Asp Val Thr Phe Ser Gly Tyr
    50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
        115                 120                 125

Thr Pro Asp Tyr Pro Glu Asp Pro Val Asp Pro Gln Tyr Pro Gly Phe
    130                 135                 140

Met Thr Arg Gly Ile Leu Asp Pro Arg Thr Tyr Tyr Tyr Arg Arg Val
145                 150                 155                 160

Phe Thr Asp Ala Val Arg Ala Val Glu Ala Ala Ser Phe Pro Arg
                165                 170                 175

Val Asp His Glu Arg Ile Val Ile Ala Gly Gly Ser Gln Gly Gly Gly
            180                 185                 190

Ile Ala Leu Ala Val Ser Ala Leu Ser Lys Ala Lys Ala Leu Leu
        195                 200                 205

Cys Asp Val Pro Phe Leu Cys His Phe Arg Arg Ala Val Gln Leu Val
210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Val Arg Ala Lys Ile Pro Ala Leu Phe Ser Val Gly Leu
            260                 265                 270

Met Asp Asn Ile Ser Pro Pro Ser Thr Val Phe Ala Ala Tyr Asn His
        275                 280                 285

Tyr Ala Gly Pro Lys Glu Ile Arg Ile Tyr Pro Tyr Asn Asn His Glu
    290                 295                 300

Gly Gly Gly Ser Phe Gln Ala Ile Glu Gln Val Lys Phe Leu Lys Arg
305                 310                 315                 320

Leu Phe Glu Lys Gly
            325

```
<210> SEQ ID NO 40
<211> LENGTH: 325
<212> TYPE: PRT
<213> ORGANISM: artificial sequence
<220> FEATURE:
<223> OTHER INFORMATION: synthetic construct

<400> SEQUENCE: 40

Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Lys Glu Thr Leu
            20                  25                  30

Ala Glu Ser Glu Lys Phe Pro Leu Asp Pro Val Phe Glu Arg Met Glu
        35                  40                  45

Ser His Leu Lys Thr Val Glu Val Tyr Asp Val Thr Phe Ser Gly Tyr
    50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
        115                 120                 125

Thr Pro Asp Tyr Pro Glu Asp Pro Val Asp Pro Gln Tyr Pro Gly Phe
    130                 135                 140

Met Thr Arg Gly Ile Leu Asp Pro Arg Thr Tyr Tyr Tyr Arg Arg Val
145                 150                 155                 160

Phe Thr Asp Ala Val Arg Ala Val Glu Ala Ala Ser Phe Pro Arg
                165                 170                 175

Val Asp His Glu Arg Ile Val Ile Ala Gly Gly Ser Gln Gly Gly Gly
            180                 185                 190

Ile Ala Leu Ala Val Ser Ala Leu Ser Lys Lys Ala Lys Ala Leu Leu
        195                 200                 205

Cys Asp Val Pro Phe Leu Cys His Phe Arg Arg Ala Val Gln Leu Val
    210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Val Arg Ala Lys Ile Pro Ala Leu Phe Ser Val Gly Leu
            260                 265                 270

Met Asp Asn Ile Thr Pro Pro Ser Thr Val Phe Ala Ala Tyr Asn His
        275                 280                 285

Tyr Ala Gly Pro Lys Glu Ile Arg Ile Tyr Pro Tyr Asn Asn His Glu
    290                 295                 300

Gly Gly Gly Ser Phe Gln Ala Ile Glu Gln Val Lys Phe Leu Lys Arg
305                 310                 315                 320

Leu Phe Glu Lys Gly
                325

<210> SEQ ID NO 41
<211> LENGTH: 990
<212> TYPE: DNA
<213> ORGANISM: Thermotoga sp.

<400> SEQUENCE: 41
```

-continued

```
atggcgctat tgatatgcc tctggaaaag ttaagatcat accttcccga tagatacgag    60
gaggaagatt ttgatctgtt ctggaaagag actcttgagg agtcaagaaa attcccactg   120
gatcctattt ttgaaagagt agattatctg ctggagaacg tggaagtata cgatgtcacc   180
ttctccggtt acaggggtca agaataaaag gcgtggttga ttctaccggt tgttaagaag   240
gaagaaaggc ttccctgcat cgttgaattc ataggttaca ggggaggaag aggttttccc   300
ttcgattggc tcttctggag cagtgcgggg tatgcccatt tcgtgatgga cactcgcggc   360
cagggaacca gtagagtaaa gggtgatact cctgactact gtgatgaacc cataaatcct   420
caattccccg gattcatgac gcggggaata ctggatccca ggacttacta ttacagaaga   480
gttttttaccg atgctgtaag agcagtggaa accgcttcga gtttcccggg aatagatccc   540
gaaaggatag ccgtcgtggg aacaagccag ggtggggaa ttgcattggc ggtgcggcg     600
ctttccgaaa ttccaaaggc tcttgtatcg aatgttccgt ttctgtgtca tttcagaaga   660
gcggttcaga taacagataa cgctccttac agtgagatag tgaattattt gaaagtccac   720
agagacaaag aggaaattgt gttcagaacg ctttcgtact ttgatggagt gaactttgct   780
gcgagggcaa aaataccagc acttttctct gttgctctca tggacaaaac ctgtccacct   840
tctacagttt ttgctgctta caaccattac gctggtccaa agaaatcaa agtgtatcca    900
ttcaacgaac atgaaggtgg agaatctttc cagagaatgg aggaacttcg ctttatgaaa   960
aggattctaa aagggggaatt caaagcatga                                  990
```

<210> SEQ ID NO 42
<211> LENGTH: 329
<212> TYPE: PRT
<213> ORGANISM: Thermotoga sp.

<400> SEQUENCE: 42

```
Met Ala Leu Phe Asp Met Pro Leu Glu Lys Leu Arg Ser Tyr Leu Pro
1               5                   10                  15
Asp Arg Tyr Glu Glu Asp Phe Asp Leu Phe Trp Lys Glu Thr Leu
            20                  25                  30
Glu Glu Ser Arg Lys Phe Pro Leu Asp Pro Ile Phe Glu Arg Val Asp
        35                  40                  45
Tyr Leu Leu Glu Asn Val Glu Val Tyr Asp Val Thr Phe Ser Gly Tyr
    50                  55                  60
Arg Gly Gln Arg Ile Lys Ala Trp Leu Ile Leu Pro Val Val Lys Lys
65                  70                  75                  80
Glu Glu Arg Leu Pro Cys Ile Val Glu Phe Ile Gly Tyr Arg Gly Gly
                85                  90                  95
Arg Gly Phe Pro Phe Asp Trp Leu Phe Trp Ser Ser Ala Gly Tyr Ala
            100                 105                 110
His Phe Val Met Asp Thr Arg Gly Gln Gly Thr Ser Arg Val Lys Gly
        115                 120                 125
Asp Thr Pro Asp Tyr Cys Asp Glu Pro Ile Asn Pro Gln Phe Pro Gly
    130                 135                 140
Phe Met Thr Arg Gly Ile Leu Asp Pro Arg Thr Tyr Tyr Tyr Arg Arg
145                 150                 155                 160
Val Phe Thr Asp Ala Val Arg Ala Val Glu Thr Ala Ser Ser Phe Pro
                165                 170                 175
Gly Ile Asp Pro Glu Arg Ile Ala Val Val Gly Thr Ser Gln Gly Gly
            180                 185                 190
Gly Ile Ala Leu Ala Val Ala Ala Leu Ser Glu Ile Pro Lys Ala Leu
        195                 200                 205
```

Val Ser Asn Val Pro Phe Leu Cys His Phe Arg Arg Ala Val Gln Ile
210                 215                 220

Thr Asp Asn Ala Pro Tyr Ser Glu Ile Val Asn Tyr Leu Lys Val His
225                 230                 235                 240

Arg Asp Lys Glu Glu Ile Val Phe Arg Thr Leu Ser Tyr Phe Asp Gly
                245                 250                 255

Val Asn Phe Ala Ala Arg Ala Lys Ile Pro Ala Leu Phe Ser Val Ala
            260                 265                 270

Leu Met Asp Lys Thr Cys Pro Pro Ser Thr Val Phe Ala Ala Tyr Asn
        275                 280                 285

His Tyr Ala Gly Pro Lys Glu Ile Lys Val Tyr Pro Phe Asn Glu His
    290                 295                 300

Glu Gly Gly Glu Ser Phe Gln Arg Met Glu Glu Leu Arg Phe Met Lys
305                 310                 315                 320

Arg Ile Leu Lys Gly Glu Phe Lys Ala
                325

<210> SEQ ID NO 43
<211> LENGTH: 329
<212> TYPE: PRT
<213> ORGANISM: artificial sequence
<220> FEATURE:
<223> OTHER INFORMATION: synthetic construct

<400> SEQUENCE: 43

Met Ala Leu Phe Asp Met Pro Leu Glu Lys Leu Arg Ser Tyr Leu Pro
1               5                   10                  15

Asp Arg Tyr Glu Glu Glu Asp Phe Asp Leu Phe Trp Lys Glu Thr Leu
                20                  25                  30

Glu Glu Ser Arg Lys Phe Pro Leu Asp Pro Ile Phe Glu Arg Val Asp
            35                  40                  45

Tyr Leu Leu Glu Asn Val Glu Val Tyr Asp Val Thr Phe Ser Gly Tyr
50                  55                  60

Arg Gly Gln Arg Ile Lys Ala Trp Leu Ile Leu Pro Val Val Lys Lys
65                  70                  75                  80

Glu Glu Arg Leu Pro Cys Ile Val Glu Phe Ile Gly Tyr Arg Gly Gly
                85                  90                  95

Arg Gly Phe Pro Phe Asp Trp Leu Phe Trp Ser Ser Ala Gly Tyr Ala
            100                 105                 110

His Phe Val Met Asp Thr Arg Gly Gln Gly Thr Ser Arg Val Lys Gly
        115                 120                 125

Asp Thr Pro Asp Tyr Cys Asp Glu Pro Ile Asn Pro Gln Phe Pro Gly
130                 135                 140

Phe Met Thr Arg Gly Ile Leu Asp Pro Arg Thr Tyr Tyr Tyr Arg Arg
145                 150                 155                 160

Val Phe Thr Asp Ala Val Arg Ala Val Glu Thr Ala Ser Ser Phe Pro
                165                 170                 175

Gly Ile Asp Pro Glu Arg Ile Ala Val Val Gly Thr Ser Gln Gly Gly
            180                 185                 190

Gly Ile Ala Leu Ala Val Ala Ala Leu Ser Glu Ile Pro Lys Ala Leu
        195                 200                 205

Val Ser Asn Val Pro Phe Leu Cys His Phe Arg Arg Ala Val Gln Ile
210                 215                 220

Thr Asp Asn Ala Pro Tyr Ser Glu Ile Val Asn Tyr Leu Lys Val His
225                 230                 235                 240

```
Arg Asp Lys Glu Glu Ile Val Phe Arg Thr Leu Ser Tyr Phe Asp Gly
            245                 250                 255

Val Asn Phe Ala Ala Arg Ala Lys Ile Pro Ala Leu Phe Ser Val Ala
            260                 265                 270

Leu Met Asp Lys Thr Ala Pro Pro Ser Thr Val Phe Ala Ala Tyr Asn
            275                 280                 285

His Tyr Ala Gly Pro Lys Glu Ile Lys Val Tyr Pro Phe Asn Glu His
            290                 295                 300

Glu Gly Gly Glu Ser Phe Gln Arg Met Glu Glu Leu Arg Phe Met Lys
305                 310                 315                 320

Arg Ile Leu Lys Gly Glu Phe Lys Ala
            325

<210> SEQ ID NO 44
<211> LENGTH: 329
<212> TYPE: PRT
<213> ORGANISM: artificial sequence
<220> FEATURE:
<223> OTHER INFORMATION: synthetic construct

<400> SEQUENCE: 44

Met Ala Leu Phe Asp Met Pro Leu Glu Lys Leu Arg Ser Tyr Leu Pro
1               5                   10                  15

Asp Arg Tyr Glu Glu Glu Asp Phe Asp Leu Phe Trp Lys Glu Thr Leu
            20                  25                  30

Glu Glu Ser Arg Lys Phe Pro Leu Asp Pro Ile Phe Glu Arg Val Asp
        35                  40                  45

Tyr Leu Leu Glu Asn Val Glu Val Tyr Asp Val Thr Phe Ser Gly Tyr
50                  55                  60

Arg Gly Gln Arg Ile Lys Ala Trp Leu Ile Leu Pro Val Val Lys Lys
65                  70                  75                  80

Glu Glu Arg Leu Pro Cys Ile Val Glu Phe Ile Gly Tyr Arg Gly Gly
            85                  90                  95

Arg Gly Phe Pro Phe Asp Trp Leu Phe Trp Ser Ser Ala Gly Tyr Ala
            100                 105                 110

His Phe Val Met Asp Thr Arg Gly Gln Gly Thr Ser Arg Val Lys Gly
            115                 120                 125

Asp Thr Pro Asp Tyr Cys Asp Glu Pro Ile Asn Pro Gln Phe Pro Gly
        130                 135                 140

Phe Met Thr Arg Gly Ile Leu Asp Pro Arg Thr Tyr Tyr Tyr Arg Arg
145                 150                 155                 160

Val Phe Thr Asp Ala Val Arg Ala Val Glu Thr Ala Ser Ser Phe Pro
            165                 170                 175

Gly Ile Asp Pro Glu Arg Ile Ala Val Val Gly Thr Ser Gln Gly Gly
            180                 185                 190

Gly Ile Ala Leu Ala Val Ala Ala Leu Ser Glu Ile Pro Lys Ala Leu
            195                 200                 205

Val Ser Asn Val Pro Phe Leu Cys His Phe Arg Arg Ala Val Gln Ile
        210                 215                 220

Thr Asp Asn Ala Pro Tyr Ser Glu Ile Val Asn Tyr Leu Lys Val His
225                 230                 235                 240

Arg Asp Lys Glu Glu Ile Val Phe Arg Thr Leu Ser Tyr Phe Asp Gly
            245                 250                 255

Val Asn Phe Ala Ala Arg Ala Lys Ile Pro Ala Leu Phe Ser Val Ala
            260                 265                 270

Leu Met Asp Lys Thr Val Pro Pro Ser Thr Val Phe Ala Ala Tyr Asn
```

```
            275                 280                 285
His Tyr Ala Gly Pro Lys Glu Ile Lys Val Tyr Pro Phe Asn Glu His
290                 295                 300

Glu Gly Gly Glu Ser Phe Gln Arg Met Glu Glu Leu Arg Phe Met Lys
305                 310                 315                 320

Arg Ile Leu Lys Gly Glu Phe Lys Ala
                325

<210> SEQ ID NO 45
<211> LENGTH: 329
<212> TYPE: PRT
<213> ORGANISM: artificial sequence
<220> FEATURE:
<223> OTHER INFORMATION: synthetic construct

<400> SEQUENCE: 45

Met Ala Leu Phe Asp Met Pro Leu Glu Lys Leu Arg Ser Tyr Leu Pro
1               5                   10                  15

Asp Arg Tyr Glu Glu Asp Phe Asp Leu Phe Trp Lys Glu Thr Leu
            20                  25                  30

Glu Glu Ser Arg Lys Phe Pro Leu Asp Pro Ile Phe Glu Arg Val Asp
        35                  40                  45

Tyr Leu Leu Glu Asn Val Glu Val Tyr Asp Val Thr Phe Ser Gly Tyr
50                  55                  60

Arg Gly Gln Arg Ile Lys Ala Trp Leu Ile Leu Pro Val Val Lys Lys
65                  70                  75                  80

Glu Glu Arg Leu Pro Cys Ile Val Glu Phe Ile Gly Tyr Arg Gly Gly
                85                  90                  95

Arg Gly Phe Pro Phe Asp Trp Leu Phe Trp Ser Ser Ala Gly Tyr Ala
            100                 105                 110

His Phe Val Met Asp Thr Arg Gly Gln Gly Thr Ser Arg Val Lys Gly
        115                 120                 125

Asp Thr Pro Asp Tyr Cys Asp Glu Pro Ile Asn Pro Gln Phe Pro Gly
130                 135                 140

Phe Met Thr Arg Gly Ile Leu Asp Pro Arg Thr Tyr Tyr Tyr Arg Arg
145                 150                 155                 160

Val Phe Thr Asp Ala Val Arg Ala Val Glu Thr Ala Ser Ser Phe Pro
                165                 170                 175

Gly Ile Asp Pro Glu Arg Ile Ala Val Val Gly Thr Ser Gln Gly Gly
            180                 185                 190

Gly Ile Ala Leu Ala Val Ala Ala Leu Ser Glu Ile Pro Lys Ala Leu
        195                 200                 205

Val Ser Asn Val Pro Phe Leu Cys His Phe Arg Arg Ala Val Gln Ile
210                 215                 220

Thr Asp Asn Ala Pro Tyr Ser Glu Ile Val Asn Tyr Leu Lys Val His
225                 230                 235                 240

Arg Asp Lys Glu Glu Ile Val Phe Arg Thr Leu Ser Tyr Phe Asp Gly
                245                 250                 255

Val Asn Phe Ala Ala Arg Ala Lys Ile Pro Ala Leu Phe Ser Val Ala
            260                 265                 270

Leu Met Asp Lys Thr Ser Pro Pro Ser Thr Val Phe Ala Ala Tyr Asn
        275                 280                 285

His Tyr Ala Gly Pro Lys Glu Ile Lys Val Tyr Pro Phe Asn Glu His
290                 295                 300

Glu Gly Gly Glu Ser Phe Gln Arg Met Glu Glu Leu Arg Phe Met Lys
305                 310                 315                 320
```

Arg Ile Leu Lys Gly Glu Phe Lys Ala
            325

<210> SEQ ID NO 46
<211> LENGTH: 329
<212> TYPE: PRT
<213> ORGANISM: artificial sequence
<220> FEATURE:
<223> OTHER INFORMATION: synthetic construct

<400> SEQUENCE: 46

Met Ala Leu Phe Asp Met Pro Leu Glu Lys Leu Arg Ser Tyr Leu Pro
1               5                   10                  15

Asp Arg Tyr Glu Glu Glu Asp Phe Asp Leu Phe Trp Lys Glu Thr Leu
            20                  25                  30

Glu Glu Ser Arg Lys Phe Pro Leu Asp Pro Ile Phe Glu Arg Val Asp
        35                  40                  45

Tyr Leu Leu Glu Asn Val Glu Val Tyr Asp Val Thr Phe Ser Gly Tyr
    50                  55                  60

Arg Gly Gln Arg Ile Lys Ala Trp Leu Ile Leu Pro Val Val Lys Lys
65                  70                  75                  80

Glu Glu Arg Leu Pro Cys Ile Val Gly Phe Ile Gly Tyr Arg Gly Gly
                85                  90                  95

Arg Gly Phe Pro Phe Asp Trp Leu Phe Trp Ser Ser Ala Gly Tyr Ala
            100                 105                 110

His Phe Val Met Asp Thr Arg Gly Gln Gly Thr Ser Arg Val Lys Gly
        115                 120                 125

Asp Thr Pro Asp Tyr Cys Asp Glu Pro Ile Asn Pro Gln Phe Pro Gly
    130                 135                 140

Phe Met Thr Arg Gly Ile Leu Asp Pro Arg Thr Tyr Tyr Tyr Arg Arg
145                 150                 155                 160

Val Phe Thr Asp Ala Val Arg Ala Val Glu Thr Ala Ser Ser Phe Pro
                165                 170                 175

Gly Ile Asp Pro Glu Arg Ile Ala Val Val Gly Thr Ser Gln Gly Gly
            180                 185                 190

Gly Ile Ala Leu Ala Val Ala Ala Leu Ser Glu Ile Pro Lys Ala Leu
        195                 200                 205

Val Ser Asn Val Pro Phe Leu Cys His Phe Arg Arg Ala Val Gln Ile
    210                 215                 220

Thr Asp Asn Ala Pro Tyr Ser Glu Ile Val Asn Tyr Leu Lys Val His
225                 230                 235                 240

Arg Asp Lys Glu Glu Ile Val Phe Arg Thr Leu Ser Tyr Phe Asp Gly
                245                 250                 255

Val Asn Phe Ala Ala Arg Ala Lys Ile Pro Ala Leu Phe Ser Val Ala
            260                 265                 270

Leu Met Asp Lys Thr Thr Pro Pro Ser Thr Val Phe Ala Ala Tyr Asn
        275                 280                 285

His Tyr Ala Gly Pro Lys Glu Ile Lys Val Tyr Pro Phe Asn Glu His
    290                 295                 300

Glu Gly Gly Glu Ser Phe Gln Arg Met Glu Glu Leu Arg Phe Met Lys
305                 310                 315                 320

Arg Ile Leu Lys Gly Glu Phe Lys Ala
            325

<210> SEQ ID NO 47
<211> LENGTH: 50

```
<212> TYPE: DNA
<213> ORGANISM: artificial sequence
<220> FEATURE:
<223> OTHER INFORMATION: synthetic construct

<400> SEQUENCE: 47
taactgcagt aaggaggaat aggacatggc cttcttcgat ttacccactc            50

<210> SEQ ID NO 48
<211> LENGTH: 38
<212> TYPE: DNA
<213> ORGANISM: artificial sequence
<220> FEATURE:
<223> OTHER INFORMATION: synthetic construct

<400> SEQUENCE: 48
tgatctagat tagcctttct caaatagttt tttcaaga                         38

<210> SEQ ID NO 49
<211> LENGTH: 1012
<212> TYPE: DNA
<213> ORGANISM: artificial sequence
<220> FEATURE:
<223> OTHER INFORMATION: synthetic construct

<400> SEQUENCE: 49
taactgcagt aaggaggaat aggacatggc cttcttcgat ttaccactcg aagaactgaa    60
gaaatatcgt ccagagcggt acgaagagaa agacttcgat gagttctggg aagagacact   120
cgcagagagc gaaaagttcc ccttagaccc cgtcttcgag aggatggagt ctcacctcaa   180
aacagtcgaa gcgtacgatg tcaccttctc cggatacagg ggacagagga tcaaagggtg   240
gctccttgtt ccaaaactgg aagaagaaaa acttccctgc gttgtgcagt acataggata   300
caacggtgga agaggattcc ctcacgactg gctgttctgg ccttctatgg gttacatatg   360
tttcgtcatg gatactcgag gtcagggaag cggctggctg aaaggagaca caccggatta   420
ccctgagggt cccgttgacc ctcagtatcc aggattcatg acaagaggaa tactggatcc   480
cagaacttac tactacagac gagtcttcac ggacgctgtc agagccgttg aagctgctgc   540
ttcttttcct caggtagatc aagaaagaat cgtgatagct ggaggcagtc agggtggcgg   600
aatagccctt gcggtgagcg ctctctcaaa gaaagcaaag gctcttctgt gcgatgtgcc   660
gtttctgtgt cacttcagaa gagcagtaca gcttgtggat acgcatccat acgcggagat   720
cacgaacttt ctaaagaccc acagagacaa ggaagaaatc gtgttcagga ctctttccta   780
tttcgatgga gtgaacttcg cagccagagc gaagatccct gcgctgtttt ctgtgggtct   840
catggacaac atttgtcctc cttcaacggt tttcgctgcc tacaattact acgctggacc   900
gaaggaaatc agaatctatc cgtacaacaa ccacgaggga ggaggctctt tccaagcggt  960
tgaacaggtg aaattcttga aaaaactatt tgagaaaggc taatctagat ca          1012

<210> SEQ ID NO 50
<211> LENGTH: 47
<212> TYPE: DNA
<213> ORGANISM: artificial sequence
<220> FEATURE:
<223> OTHER INFORMATION: synthetic construct

<400> SEQUENCE: 50
taagaattct aaggaatagg acatggcgtt tcttcgacct gcctctg                47

<210> SEQ ID NO 51
<211> LENGTH: 36
```

```
<212> TYPE: DNA
<213> ORGANISM: artificial sequence
<220> FEATURE:
<223> OTHER INFORMATION: synthetic construct

<400> SEQUENCE: 51
aaactgcagt tagcccttct caaacagttt cttcag                                36

<210> SEQ ID NO 52
<211> LENGTH: 978
<212> TYPE: DNA
<213> ORGANISM: artificial sequence
<220> FEATURE:
<223> OTHER INFORMATION: synthetic construct

<400> SEQUENCE: 52
atggccttct tcgatttacc actcgaagaa ctgaagaaat atcgtccaga gcggtacgaa        60
gagaaagact tcgatgagtt ctgggaagag acactcgcag agagcgaaaa gttcccctta       120
gaccccgtct tcgagaggat ggagtctcac ctcaaaacag tcgaagcgta cgatgtcacc       180
ttctccggat acaggggaca gaggatcaaa gggtggctcc ttgttccaaa actggaagaa       240
gaaaaacttc cctgcgttgt gcagtacata ggatacaacg tggaagagg attccctcac        300 gactggctgt tctggccttc tatgggttac atatgtttcg tcatggatac tcgaggtcag       360
ggaagcggct ggctgaaagg agacacaccg gattaccctg agggtcccgt tgaccctcag       420
tatccaggat tcatgacaag aggaatactg gatcccagaa cttactacta cagacgagtc       480
ttcacggacg ctgtcagagc cgttgaagct gctgcttctt tcctcaggt agatcaagaa        540 agaatcgtga tagctggagg cagtcagggt ggcggaatag cccttgcggt gagcgctctc       600
tcaaagaaag caaaggctct tctgtgcgat gtgccgtttc tgtgtcactt cagaagagca       660
gtacagcttg tggatacgca tccatacgcg gagatcacga actttctaaa gacccacaga       720
gacaaggaag aaatcgtgtt caggactctt tcctatttcg atggagtgaa cttcgcagcc       780
agagcgaaga tccctgcgct gttttctgtg ggtctcatgg acaacatttg tcctccttca       840
acggttttcg ctgcctacaa ttactacgct ggaccgaagg aaatcagaat ctatccgtac       900
aacaaccacg agggaggagg ctctttccaa gcggttgaac aggtgaaatt cttgaaaaaa       960
ctatttgaga aaggctaa                                                    978

<210> SEQ ID NO 53
<211> LENGTH: 23
<212> TYPE: DNA
<213> ORGANISM: artificial sequence
<220> FEATURE:
<223> OTHER INFORMATION: synthetic construct

<400> SEQUENCE: 53
ggacaacatc gtgcctcctt cta                                               23

<210> SEQ ID NO 54
<211> LENGTH: 23
<212> TYPE: DNA
<213> ORGANISM: artificial sequence
<220> FEATURE:
<223> OTHER INFORMATION: synthetic construct

<400> SEQUENCE: 54
tagaaggagg cacgatgttg tcc                                               23

<210> SEQ ID NO 55
<211> LENGTH: 23
```

```
<212> TYPE: DNA
<213> ORGANISM: artificial sequence
<220> FEATURE:
<223> OTHER INFORMATION: synthetic construct

<400> SEQUENCE: 55
ggacaacatc gcgcctcctt cta                                          23

<210> SEQ ID NO 56
<211> LENGTH: 23
<212> TYPE: DNA
<213> ORGANISM: artificial sequence
<220> FEATURE:
<223> OTHER INFORMATION: synthetic construct

<400> SEQUENCE: 56
tagaaggagg cgcgatgttg tcc                                          23

<210> SEQ ID NO 57
<211> LENGTH: 23
<212> TYPE: DNA
<213> ORGANISM: artificial sequence
<220> FEATURE:
<223> OTHER INFORMATION: synthetic construct

<400> SEQUENCE: 57
ggacaacatc tcacctcctt cta                                          23

<210> SEQ ID NO 58
<211> LENGTH: 23
<212> TYPE: DNA
<213> ORGANISM: artificial sequence
<220> FEATURE:
<223> OTHER INFORMATION: synthetic construct

<400> SEQUENCE: 58
tagaaggagg tgagatgttg tcc                                          23

<210> SEQ ID NO 59
<211> LENGTH: 23
<212> TYPE: DNA
<213> ORGANISM: artificial sequence
<220> FEATURE:
<223> OTHER INFORMATION: synthetic construct

<400> SEQUENCE: 59
ggacaacatc acccctcctt cta                                          23

<210> SEQ ID NO 60
<211> LENGTH: 23
<212> TYPE: DNA
<213> ORGANISM: artificial sequence
<220> FEATURE:
<223> OTHER INFORMATION: synthetic construct

<400> SEQUENCE: 60
tagaaggagg ggtgatgttg tcc                                          23
```